US009895259B2

(12) United States Patent
Lerner

(10) Patent No.: US 9,895,259 B2
(45) Date of Patent: Feb. 20, 2018

(54) INTRAOCULAR DELIVERY DEVICES AND METHODS THEREFOR

(71) Applicant: OcuJect, LLC, Newport Beach, CA (US)

(72) Inventor: Leonid E. Lerner, Corona Del Mar, CA (US)

(73) Assignee: OcuJect, LLC, Newport Beach, CA (US)

( * ) Notice: Subject to any disclaimer, the term of this patent is extended or adjusted under 35 U.S.C. 154(b) by 0 days.

(21) Appl. No.: 15/442,054

(22) Filed: Feb. 24, 2017

(65) Prior Publication Data

US 2017/0165113 A1 Jun. 15, 2017

Related U.S. Application Data

(63) Continuation of application No. 15/240,949, filed on Aug. 18, 2016, which is a continuation of application
(Continued)

(51) Int. Cl.
*A61F 9/00* (2006.01)
*A61M 5/32* (2006.01)
*A61M 5/46* (2006.01)

(52) U.S. Cl.
CPC .......... *A61F 9/0017* (2013.01); *A61F 9/0026* (2013.01); *A61M 5/3243* (2013.01); *A61M 5/46* (2013.01); *A61M 2210/0612* (2013.01)

(58) Field of Classification Search
CPC .. A61M 5/3243; A61M 5/3257; A61M 5/321; A61M 2005/3217;
(Continued)

(56) References Cited

U.S. PATENT DOCUMENTS 2,674,246 A * 4/1954 Bower .................... A61M 5/32
604/198
3,134,380 A 5/1964 Armao
(Continued)

FOREIGN PATENT DOCUMENTS

JP 5-43663 2/1993
JP 6-157672 6/1994
(Continued)

OTHER PUBLICATIONS

Foreign Office Action and translation received in Chinese Application No. 201180026683.2 dated Aug. 25, 2014 in 23 pages.
(Continued)

*Primary Examiner* — Andrew Gilbert
(74) *Attorney, Agent, or Firm* — Knobbe, Martens, Olson & Bear, LLP

(57) ABSTRACT

Injection devices for delivering pharmaceutical compositions into the eye are described. Some devices include a resistance component for controllably deploying an injection needle through the eye wall. The resistance component may be disposed on a removable injector attachment or on a portion of the injection device housing. Other devices may include a filter for the removal of air, infectious agents, and/or other particulate matter from the composition before the composition is injected into the eye. Related methods and systems comprising the devices are also described.

9 Claims, 49 Drawing Sheets

Related U.S. Application Data

No. 13/841,144, filed on Mar. 15, 2013, now Pat. No. 9,421,129.

(60) Provisional application No. 61/619,308, filed on Apr. 2, 2012, provisional application No. 61/668,588, filed on Jul. 6, 2012.

(58) Field of Classification Search
CPC .......... A61M 2210/0612; A61M 2009/00844; A61M 2009/00851; A61F 9/007; A61F 9/00736
See application file for complete search history.

(56) References Cited

U.S. PATENT DOCUMENTS

| | | | |
|---|---|---|---|
| 3,403,679 A | 10/1968 | Sinclair et al. | |
| 3,406,687 A | 10/1968 | James | |
| 4,127,131 A | 11/1978 | Vaillancourt | |
| 4,416,663 A | 11/1983 | Hall | |
| 4,553,962 A | 11/1985 | Brunet | |
| 4,695,274 A | 9/1987 | Fox | |
| 4,929,241 A * | 5/1990 | Kulli | A61M 5/3243 604/110 |
| 4,998,922 A * | 3/1991 | Kuracina | A61M 5/3275 604/192 |
| 5,041,088 A | 8/1991 | Ritson et al. | |
| 5,059,184 A * | 10/1991 | Dyke | A61M 5/3257 604/198 |
| 5,088,986 A | 2/1992 | Nusbaum | |
| 5,137,516 A | 8/1992 | Rand et al. | |
| 5,300,084 A | 4/1994 | Johnson | |
| 5,304,138 A | 4/1994 | Mercado | |
| 5,304,151 A | 4/1994 | Kuracina | |
| 5,328,482 A | 7/1994 | Sircom et al. | |
| 5,334,163 A | 8/1994 | Sinnett | |
| 5,415,645 A | 5/1995 | Friend et al. | |
| 5,429,612 A | 7/1995 | Berthier | |
| 5,462,995 A | 10/1995 | Hosaka et al. | |
| 5,466,261 A | 11/1995 | Richelsoph et al. | |
| 5,472,430 A | 12/1995 | Vaillancourt et al. | |
| 5,487,733 A | 1/1996 | Caizza et al. | |
| 5,549,568 A | 8/1996 | Shields | |
| 5,584,818 A * | 12/1996 | Morrison | A61M 5/3275 604/110 |
| 5,688,253 A | 11/1997 | Paradis | |
| 5,725,493 A | 3/1998 | Avery et al. | |
| 5,830,152 A | 11/1998 | Tao | |
| 5,873,856 A | 2/1999 | Hjertman et al. | |
| 6,099,504 A | 8/2000 | Gross et al. | |
| 6,251,090 B1 | 6/2001 | Avery et al. | |
| 6,299,603 B1 | 10/2001 | Hecker et al. | |
| 6,309,374 B1 | 10/2001 | Hecker et al. | |
| 6,368,308 B1 | 4/2002 | Nerny | |
| 6,443,929 B1 * | 9/2002 | Kuracina | A61B 5/15003 604/192 |
| 6,447,482 B1 | 9/2002 | Ronborg et al. | |
| 7,314,464 B2 | 1/2008 | Giambattista et al. | |
| 7,364,570 B2 | 4/2008 | Gerondale et al. | |
| 7,374,558 B2 | 5/2008 | Kirchhofer | |
| 7,396,343 B2 | 7/2008 | Brown | |
| 7,416,540 B2 | 8/2008 | Edwards et al. | |
| 7,674,243 B2 | 3/2010 | Dacquay et al. | |
| 7,678,078 B1 * | 3/2010 | Peyman | A61F 9/0017 604/116 |
| 7,749,194 B2 | 7/2010 | Edwards et al. | |
| 7,871,399 B2 | 1/2011 | Dacquay et al. | |
| 7,901,382 B2 | 3/2011 | Daily et al. | |
| 7,918,814 B2 | 4/2011 | Prausnitz et al. | |
| 8,043,268 B1 | 10/2011 | Marks | |
| 8,221,353 B2 * | 7/2012 | Cormier | A61F 9/0017 604/116 |
| 8,287,494 B2 | 10/2012 | Ma | |
| 8,556,861 B2 | 10/2013 | Tsals | |
| 9,320,647 B2 * | 4/2016 | Lerner | A61F 9/0017 |
| 9,408,746 B2 * | 8/2016 | Lerner | |
| 9,421,129 B2 * | 8/2016 | Lerner | A61M 5/3145 |
| 9,504,603 B2 * | 11/2016 | Lerner | A61M 5/427 |
| 9,603,739 B2 | 3/2017 | Lerner | |
| 2001/0008961 A1 | 7/2001 | Hecker et al. | |
| 2002/0004648 A1 | 1/2002 | Larsen et al. | |
| 2002/0004650 A1 * | 1/2002 | Kuracina | A61M 5/3243 604/198 |
| 2002/0123721 A1 | 9/2002 | Payne et al. | |
| 2002/0133122 A1 | 9/2002 | Giambattista et al. | |
| 2002/0169421 A1 * | 11/2002 | McWethy | A61B 17/00491 604/164.12 |
| 2002/0198553 A1 | 12/2002 | Schumer et al. | |
| 2003/0040706 A1 | 2/2003 | Kuracina et al. | |
| 2003/0060763 A1 | 3/2003 | Penfold et al. | |
| 2003/0078546 A1 * | 4/2003 | Jensen | A61M 5/3202 604/232 |
| 2005/0113806 A1 | 5/2005 | De Carvalho et al. | |
| 2006/0047250 A1 | 3/2006 | Hickingbotham et al. | |
| 2006/0089607 A1 | 4/2006 | Chen | |
| 2007/0005016 A1 | 1/2007 | Williams | |
| 2007/0027452 A1 * | 2/2007 | Varner | A61F 9/0017 606/107 |
| 2007/0244442 A1 | 10/2007 | Chowhan | |
| 2007/0270767 A1 | 11/2007 | Khieu et al. | |
| 2007/0270768 A1 | 11/2007 | Dacquay et al. | |
| 2008/0097390 A1 | 4/2008 | Dacquay et al. | |
| 2008/0271277 A1 * | 11/2008 | Mizote | B60S 1/38 15/250.48 |
| 2009/0269356 A1 | 10/2009 | Epstein et al. | |
| 2010/0010452 A1 | 1/2010 | Paques et al. | |
| 2010/0020150 A1 | 1/2010 | Love | |
| 2010/0030150 A1 * | 2/2010 | Paques | A61F 9/0017 604/116 |
| 2010/0100054 A1 * | 4/2010 | Cormier | A61F 9/0017 604/239 |
| 2010/0137831 A1 * | 6/2010 | Tsals | A61M 5/3243 604/506 |
| 2010/0152646 A1 * | 6/2010 | Girijavallabhan | A61F 9/0017 604/22 |
| 2010/0152676 A1 | 6/2010 | Clements et al. | |
| 2010/0241102 A1 * | 9/2010 | Ma | A61F 9/0017 604/506 |
| 2010/0318034 A1 | 12/2010 | Goncalves | |
| 2011/0054441 A1 | 3/2011 | Erickson et al. | |
| 2012/0123353 A1 | 5/2012 | Veckeneer et al. | |
| 2013/0023824 A1 | 1/2013 | Coroneo | |
| 2013/0267910 A1 | 10/2013 | Hemmann et al. | |
| 2013/0296797 A1 | 11/2013 | Liversidge | |
| 2016/0074211 A1 | 3/2016 | Ko | |
| 2016/0310318 A1 | 10/2016 | Lerner | |
| 2016/0338877 A1 | 11/2016 | Lerner | |
| 2017/0100284 A1 | 4/2017 | Lerner | |
| 2017/0172795 A1 | 6/2017 | Lerner | |

FOREIGN PATENT DOCUMENTS

| | | |
|---|---|---|
| JP | 2003-518987 | 6/2003 |
| JP | 2008-062088 | 3/2008 |
| WO | WO 2006/082350 | 8/2006 |
| WO | WO 2007/058966 | 5/2007 |
| WO | WO 2008/084064 | 7/2008 |
| WO | WO 2011/123722 | 10/2011 |
| WO | WO 2012/019136 | 2/2012 |
| WO | WO 2012/134528 | 10/2012 |

OTHER PUBLICATIONS

Translation of Foreign Office Action received in Japanese Application No. 2013-502871 dated Jan. 23, 2015 in 7 pages.
International Search Report/Written Opinion dated Feb. 15, 2012, for PCT Application No. PCT/US11/53944 filed on Sep. 29, 2011, 7 pages.
International Search Report/ Written Opinion dated May 27, 2011, for PCT Application No. PCT/US11/30840 filed on Mar. 31, 2011, 5 pages.

(56) References Cited

OTHER PUBLICATIONS

PCT Search Report and Written Opinion dated Mar. 3, 2015 in International application No. PCT/US2014/059124 in 22 pages.
European Search Report dated Aug. 6, 2015, for EP Application No. 11862044.2 in 6 pages.
Australian Office Action dated Aug. 19, 2015 for AU Patent Application No. 2011235002 in 3 pages.
European Search Report dated Oct. 21, 2015, for EP Application No. 13772386.2 in 5 pages.
PCT Search Report and Written Opinion dated Jun. 17, 2013 in International application No. PCT/US2013/034693 in 10 pages.
Notice of Allowance dated Mar. 3, 2016 in Japanese patent application No. 2013-502871 in 3 pages.
English Translation of Foreign Office Action received in Chinese Application No. 201180026683.2 dated Nov. 30, 2015 in 2 pages.
English Translation of Foreign Office Action received in Chinese Application No. 201180026683.2 dated May 11, 2015 in 4 pages.

\* cited by examiner

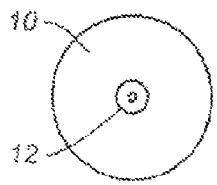
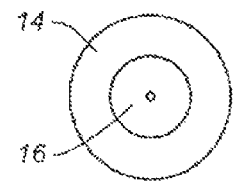
FIG. 1A  FIG. 1B
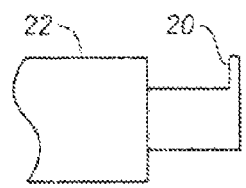
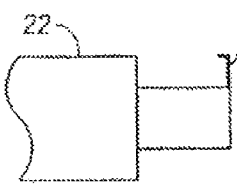
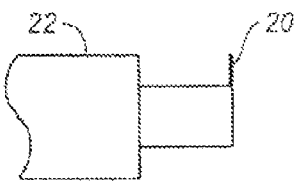
FIG. 2A  FIG. 2B  FIG. 2C
FIG. 3A1 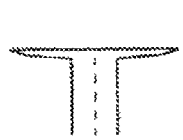 FIG. 3B1
FIG. 3A2 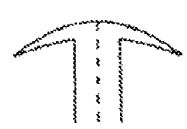 FIG. 3B2
FIG. 3A3 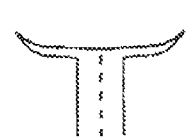 FIG. 3B3

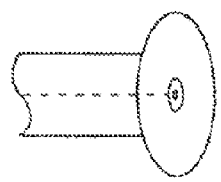  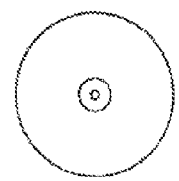
FIG. 4A        FIG. 4B1        FIG. 4B2
FIG. 5A1 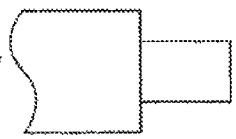      FIG. 5B1
FIG. 5A2 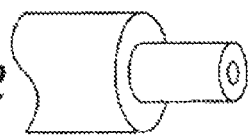     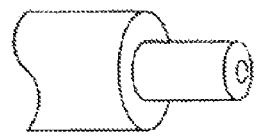 FIG. 5B2
FIG. 6A1        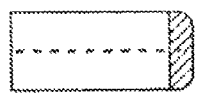    FIG. 6A2
FIG. 6B1    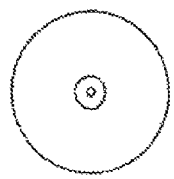    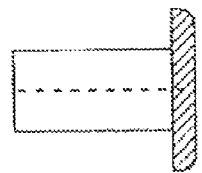    FIG. 6B2

FIG. 7A1 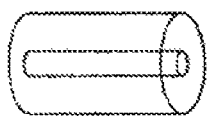 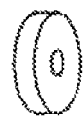 FIG. 7A2
FIG. 7B1 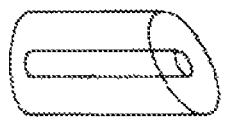  FIG. 7B2
FIG. 7C1 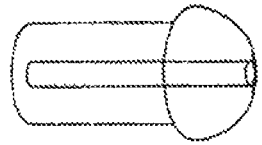  FIG. 7C2

FIG. 15A1 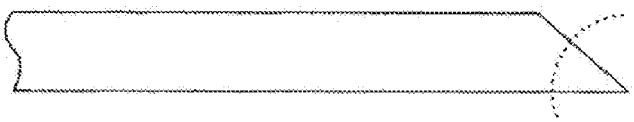
FIG. 15A2 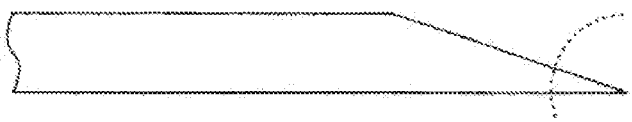
FIG. 16A 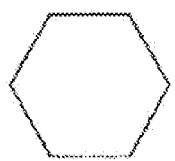 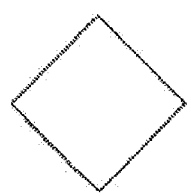 FIG. 16C
FIG. 16B 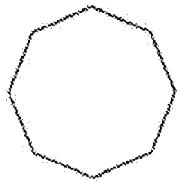 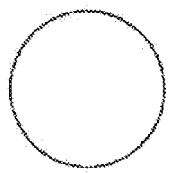 FIG. 16D
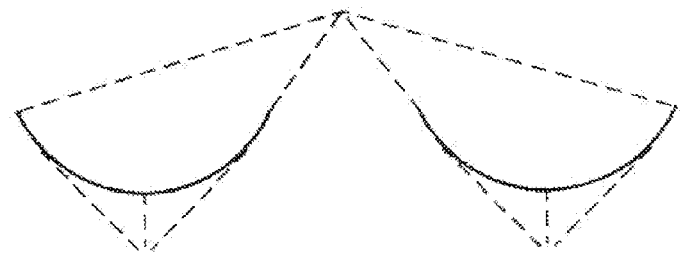
FIG. 17

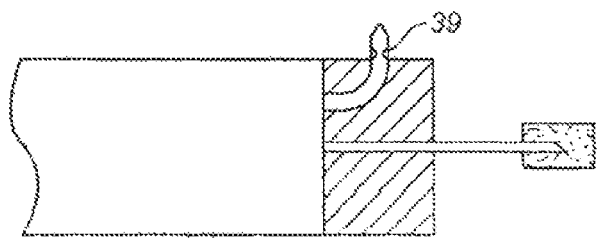
FIG. 23A
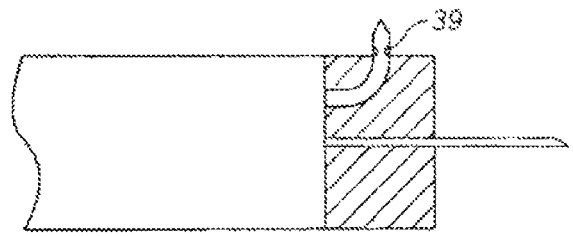
FIG. 23B
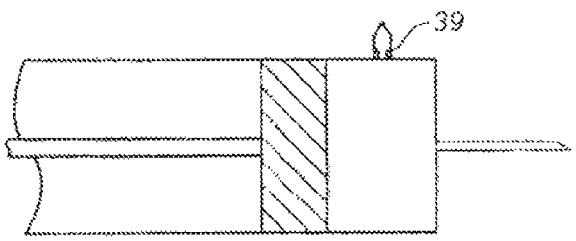
FIG. 23C
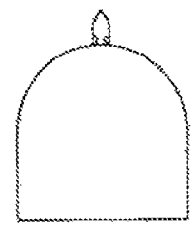 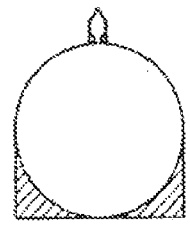 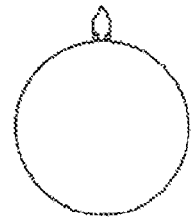
FIG. 24A    FIG. 24B    FIG. 24C
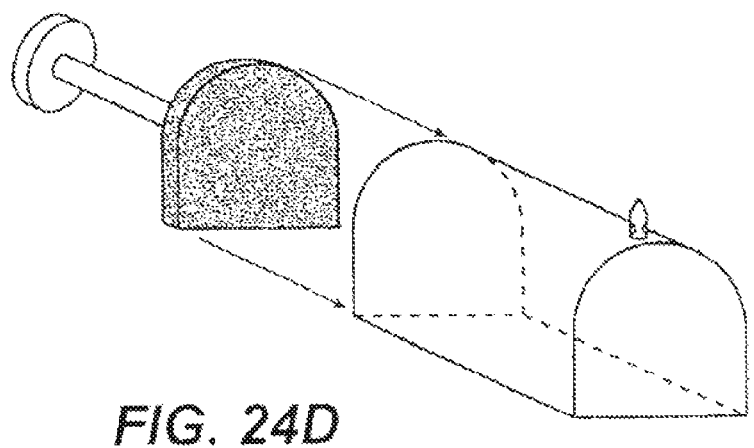
FIG. 24D

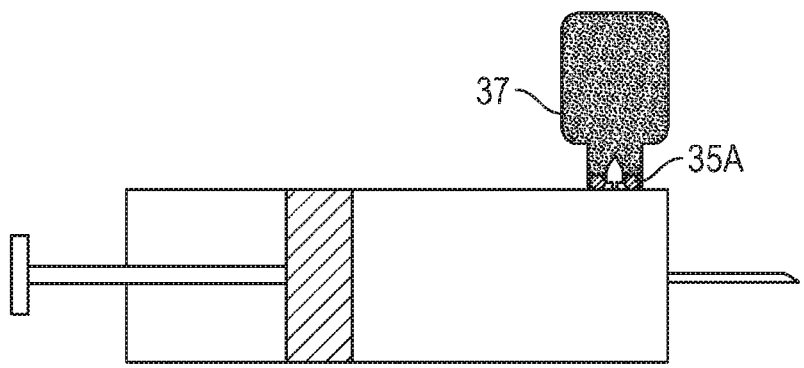
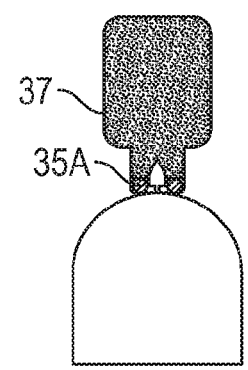
FIG. 25A   FIG. 25B
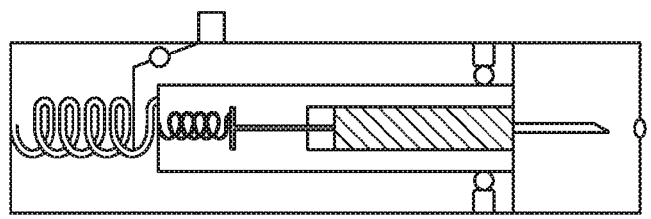
FIG. 26A
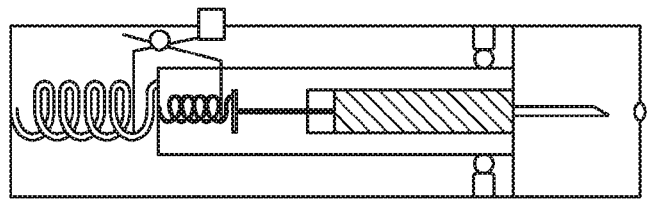
FIG. 26B
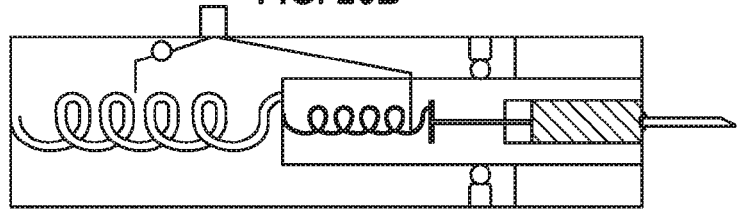
FIG. 26C
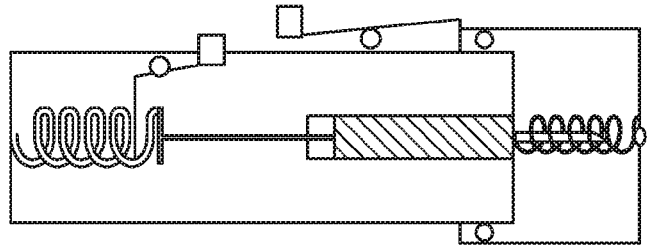
FIG. 27

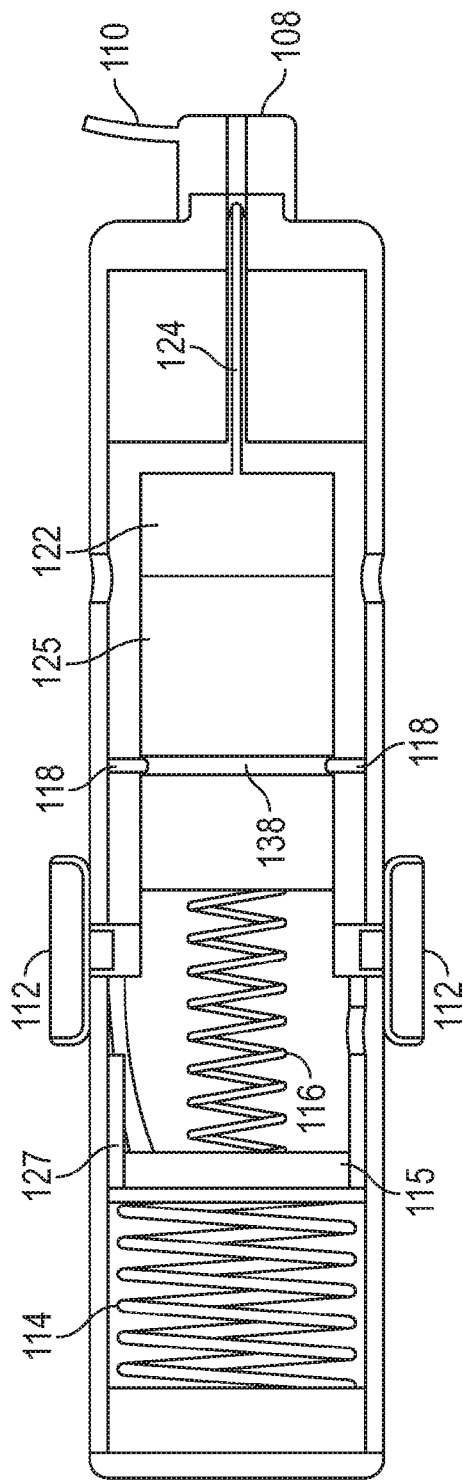
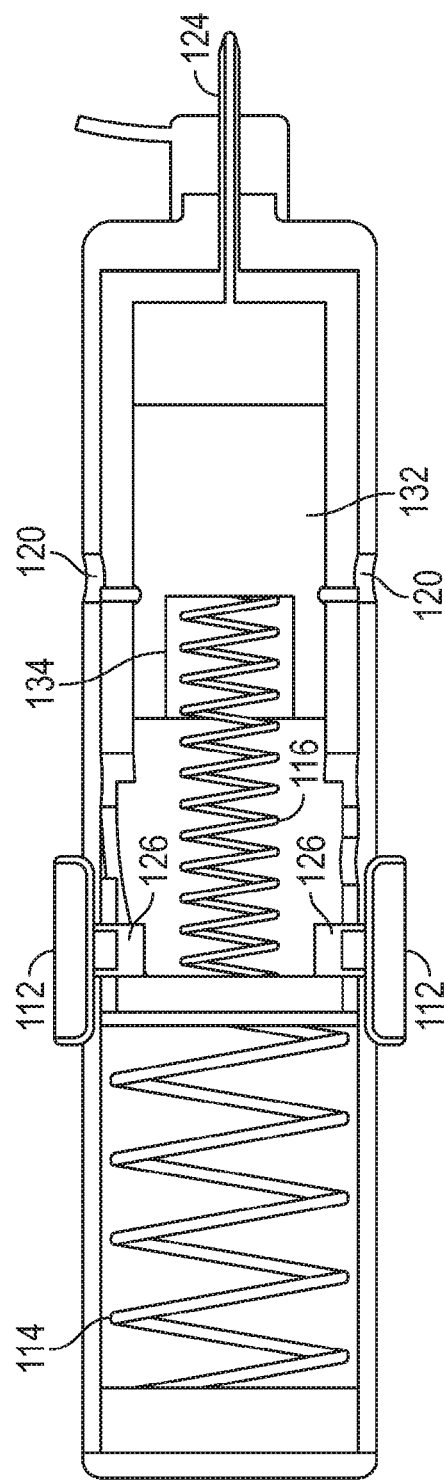
FIG. 29
FIG. 30

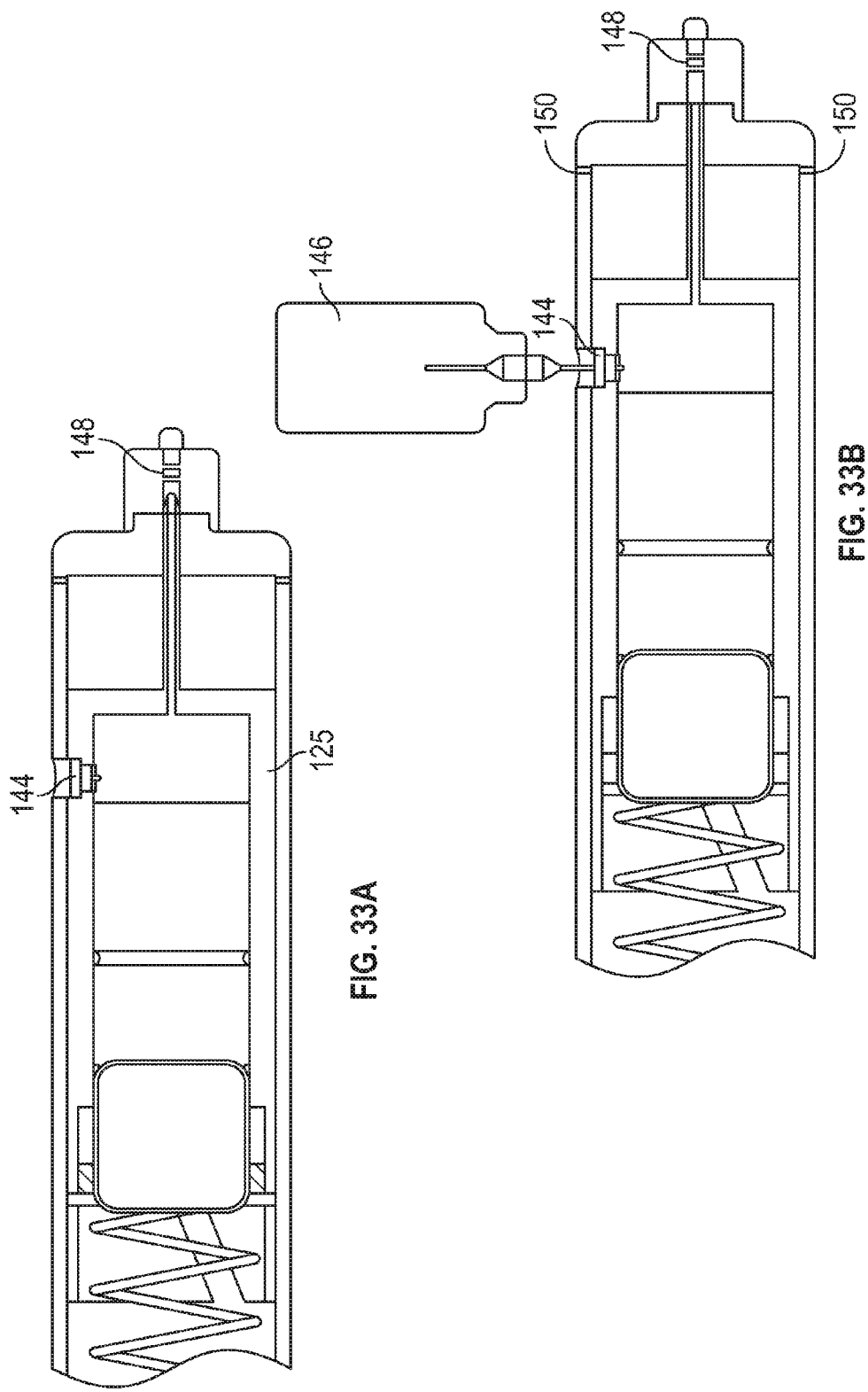

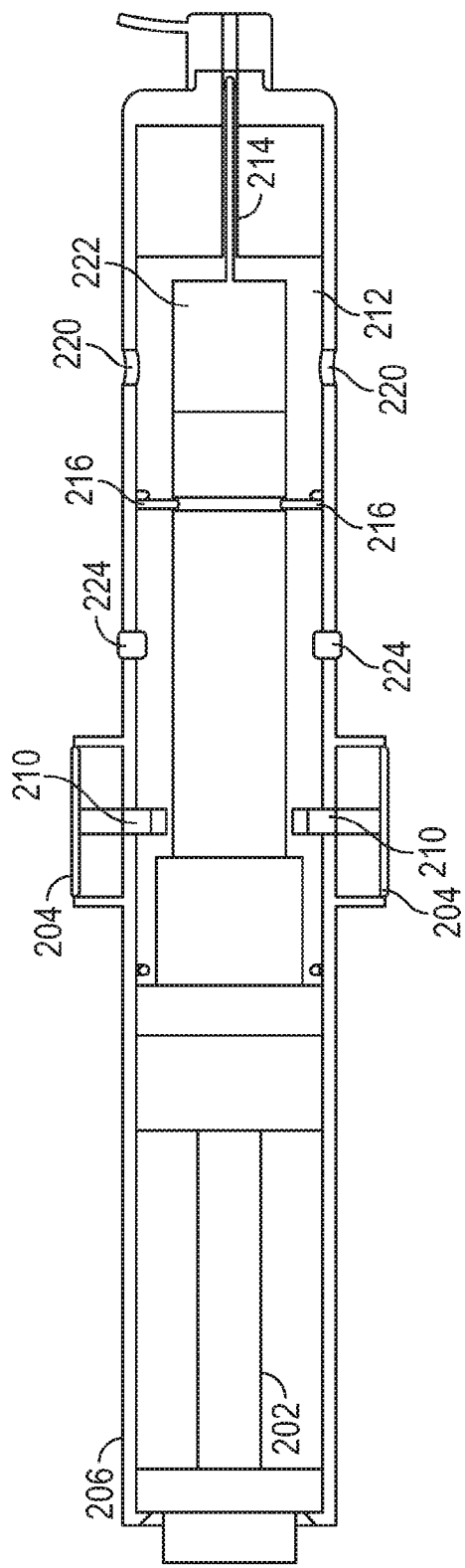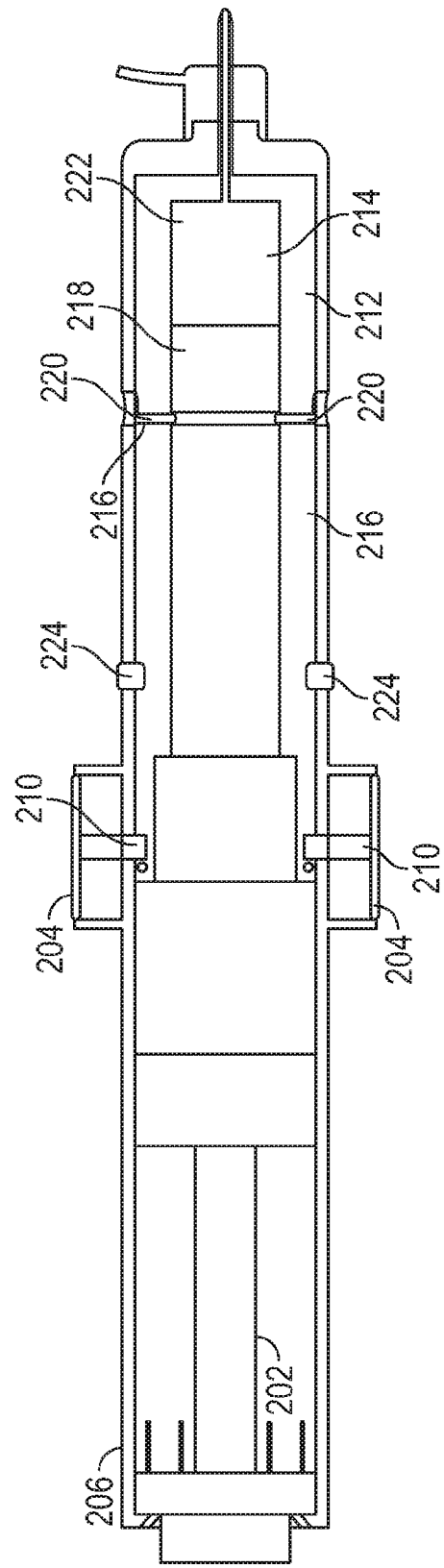

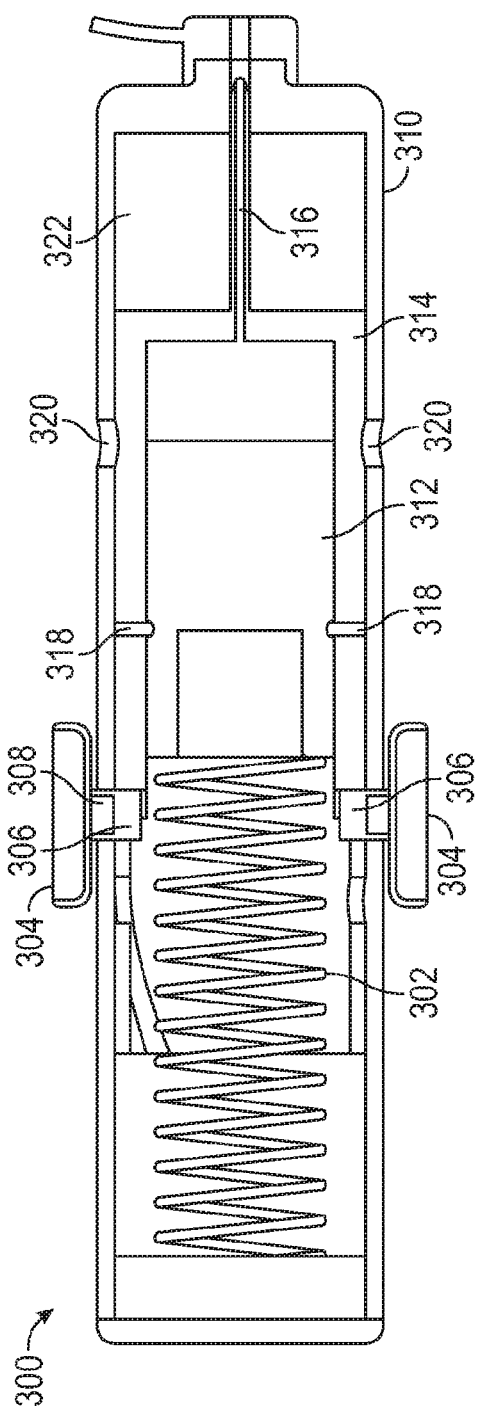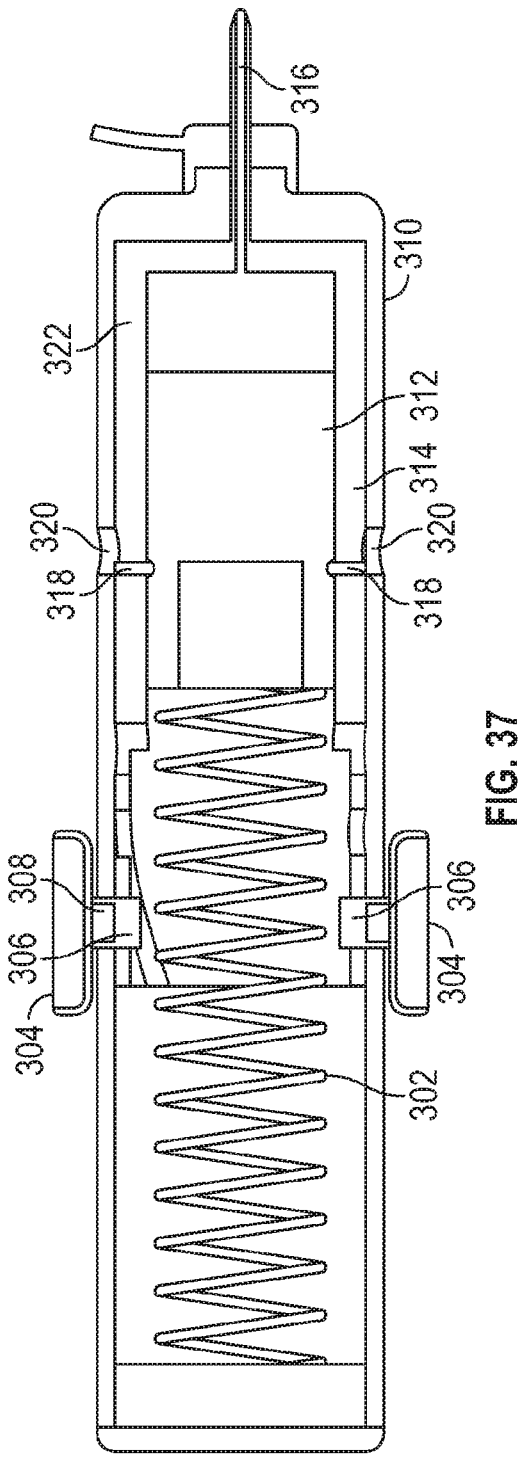
FIG. 36
FIG. 37

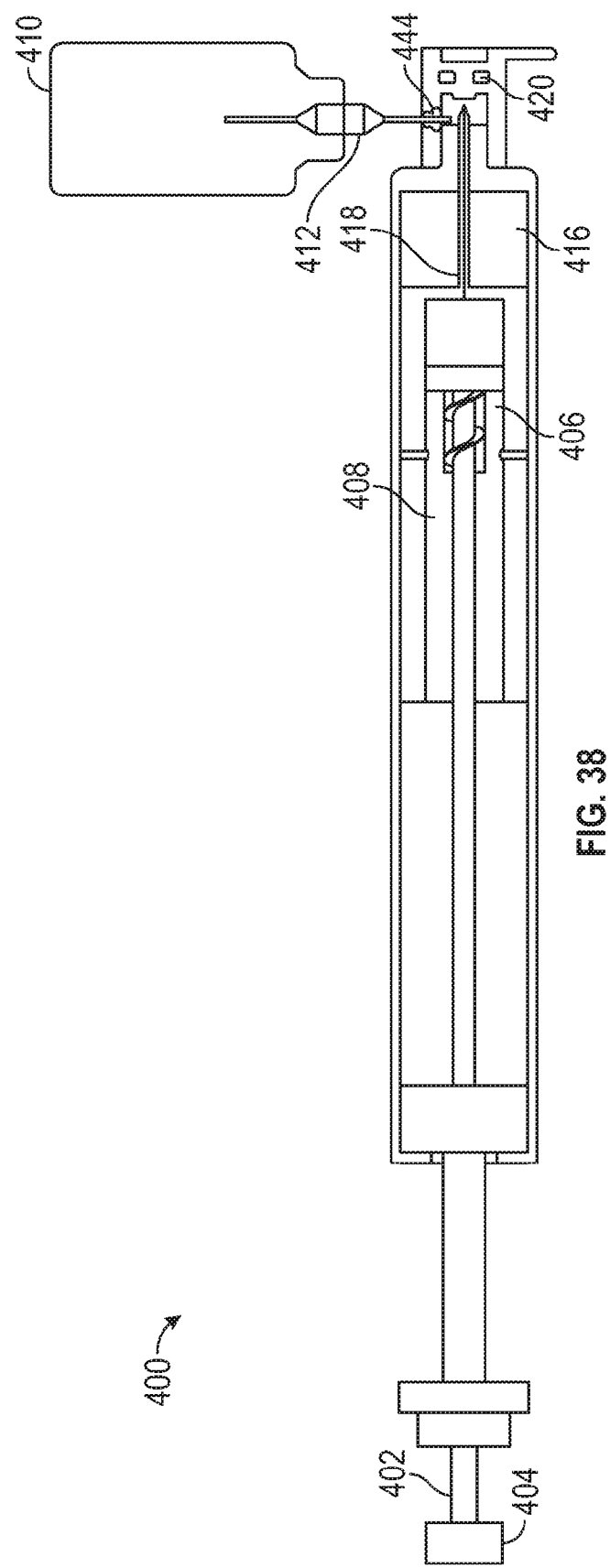

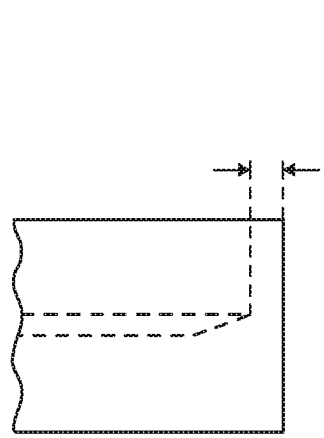
FIG. 39A
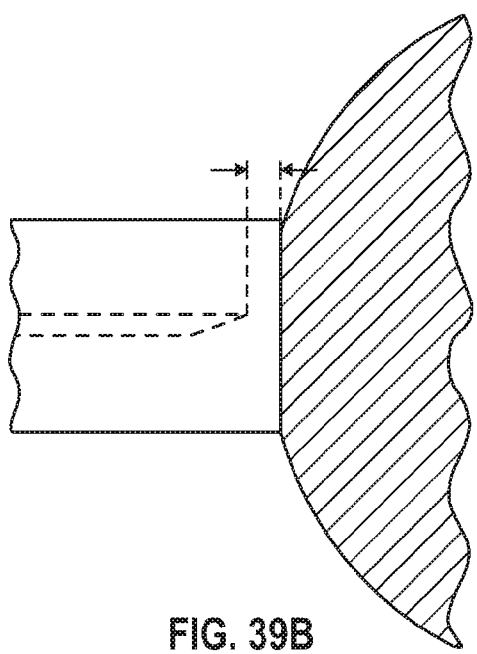
FIG. 39B
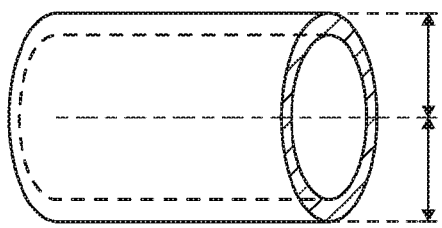
FIG. 39C
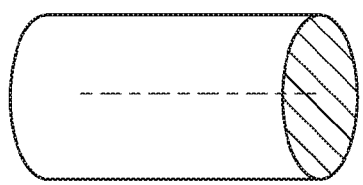
FIG. 39D
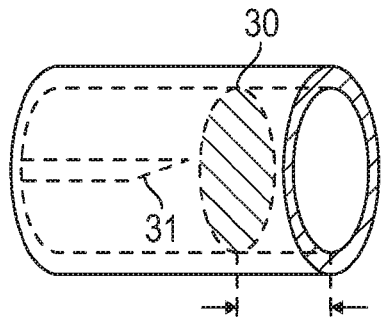
FIG. 39E
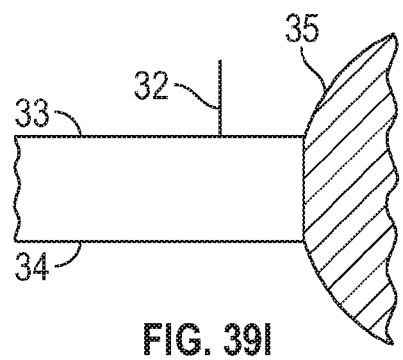
FIG. 39I
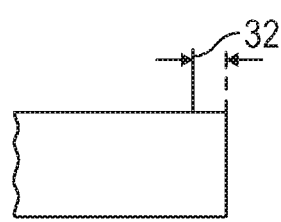
FIG. 39F
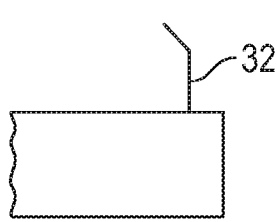
FIG. 39G
FIG. 39H

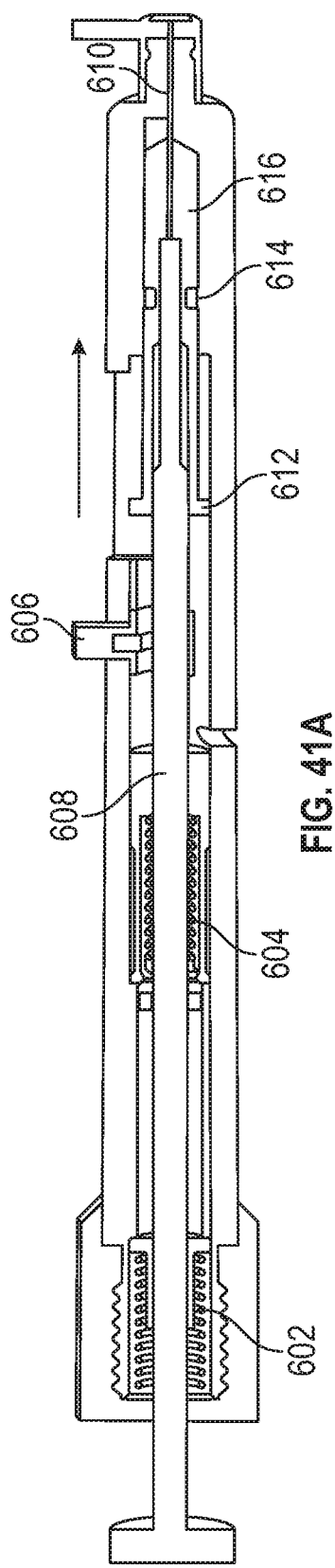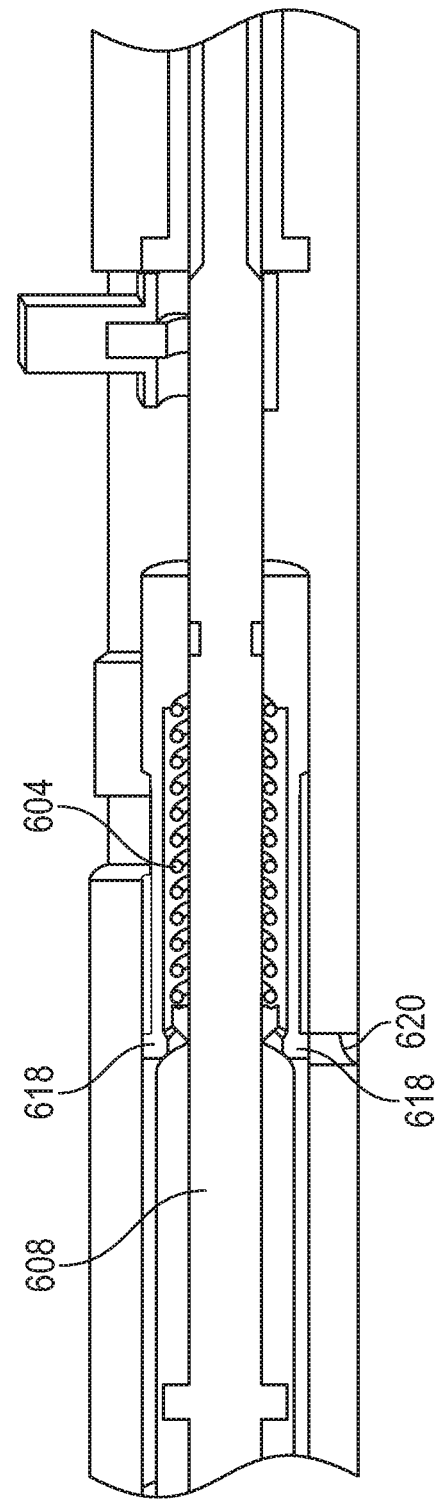
FIG. 41A
FIG. 41B

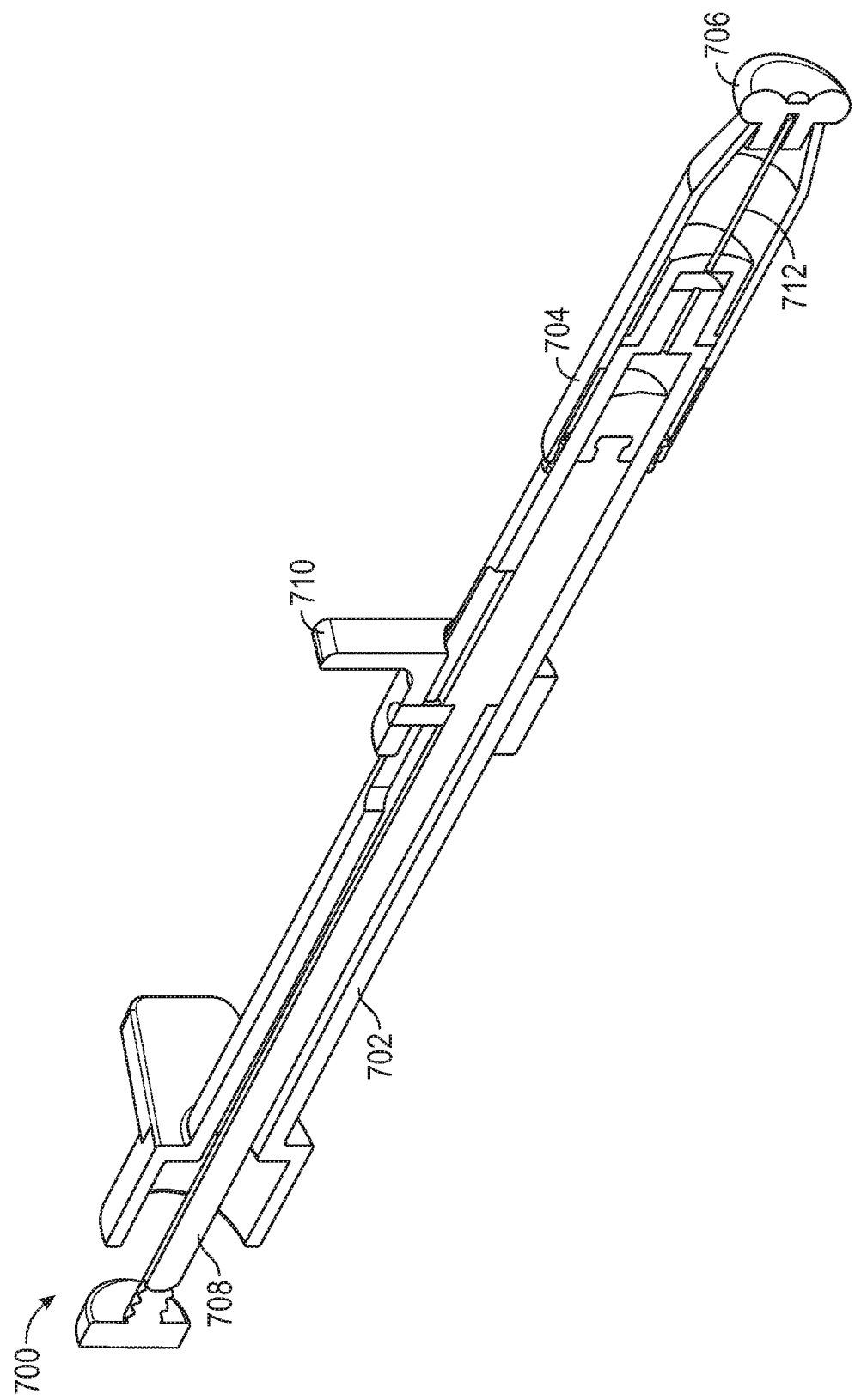

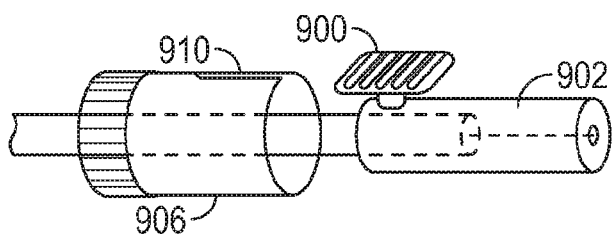 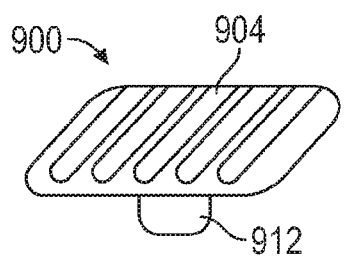
FIG. 45A  FIG. 45B
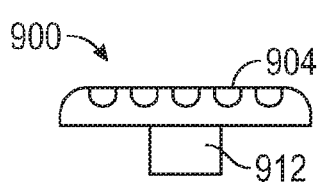 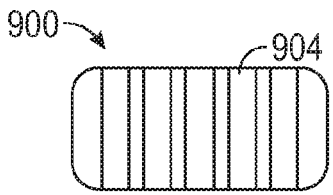
FIG. 45C  FIG. 45D
 
FIG. 45E  FIG. 45F
  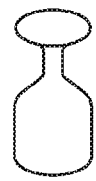
FIG. 45G  FIG. 45H  FIG. 45I
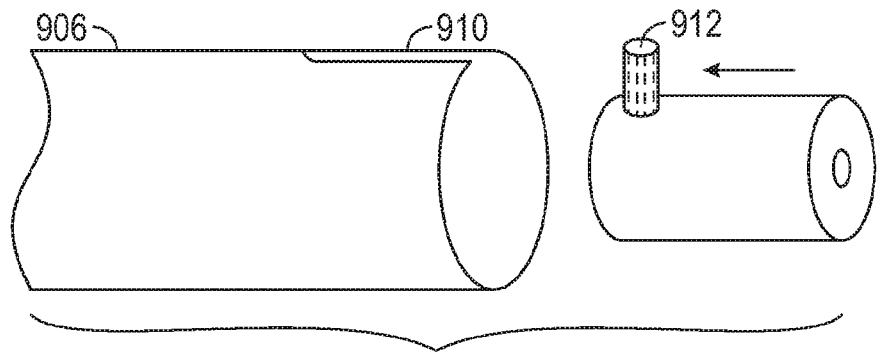
FIG. 45J

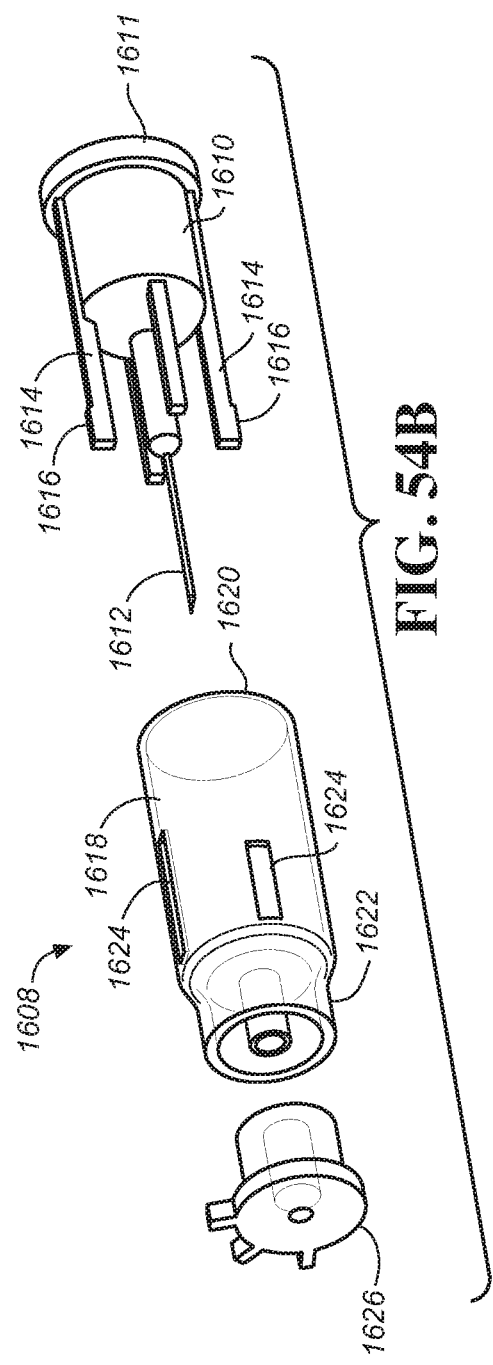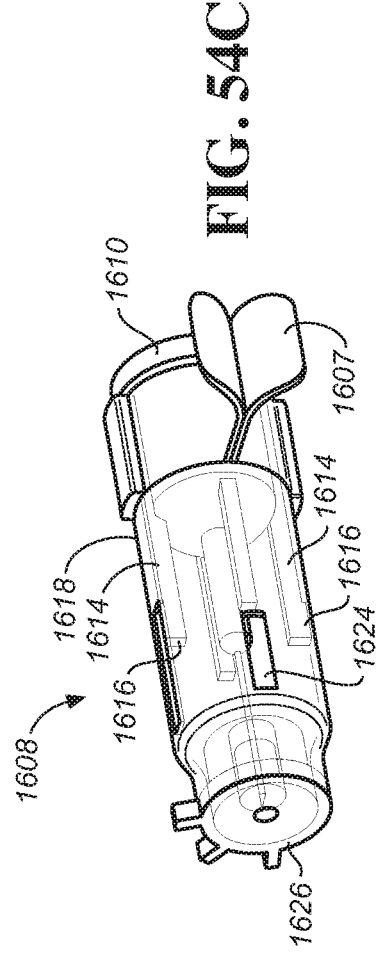

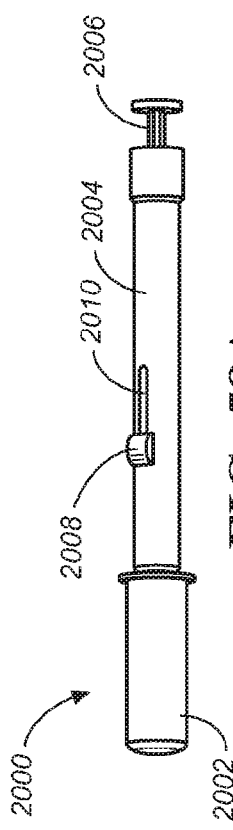
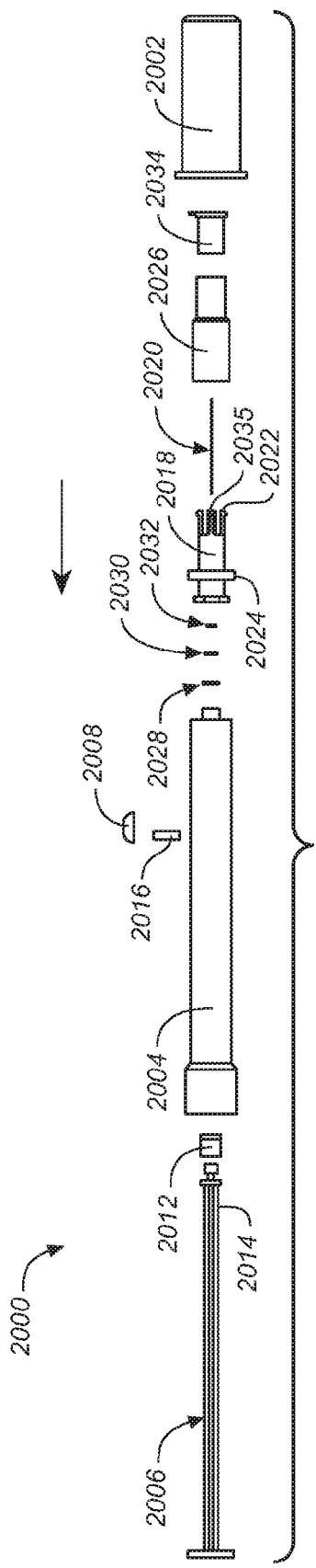
FIG. 58A
FIG. 58B

INTRAOCULAR DELIVERY DEVICES AND METHODS THEREFOR

CROSS-REFERENCE TO RELATED APPLICATIONS

This application claims priority as a continuation application of U.S. patent application Ser. No. 15/240,949 filed on Aug. 18, 2016, which is in turn a continuation application of U.S. patent application Ser. No. 13/841,144 filed on Mar. 15, 2013 now U.S. Pat. No. 9,421,129, which in turn is a nonprovisional application of U.S. Provisional Application Ser. No. 61/619,308 filed Apr. 2, 2012, and U.S. Provisional Application Ser. No. 61/668,588 filed Jul. 6, 2012. The disclosures of each of the foregoing priority applications are hereby incorporated by reference in their entireties.

FIELD

Described here are devices that are configured to safely and accurately deliver pharmaceutical formulations into the eye. Specifically, the devices may integrate various features that allow easy manipulation of the devices, and which may be beneficial for positioning of the devices on the ocular surface. Some devices include features that filter pharmaceutical formulations injected into the eye. Systems and methods for intraocularly delivering the pharmaceutical formulations using the devices are also described.

BACKGROUND

The eye is a complex organ comprised of many parts that enable the process of sight. Vision quality depends on the condition of each individual part and the ability of these parts to work together. For example, vision may be affected by conditions that affect the lens (e.g., cataracts), retina (e.g., CMV retinitis), or the macula (e.g., macular degeneration). Topical and systemic drug formulations have been developed to treat these and other ocular conditions, but each has its drawbacks. For example, topical therapies that are applied on the surface of the eye typically possess short residence times due to tear flow that washes them out of the eye. Furthermore, delivery of drugs into the eye is limited due to the natural barrier presented by the cornea and sclera, and additional structures if the intended target resides within the posterior chamber. With respect to systemic treatments, high doses of drug are often required in order to obtain therapeutic levels within the eye, which increases the risk of adverse side-effects.

Alternatively, intravitreal injections have been performed to locally deliver pharmaceutical formulations into the eye. The use of intravitreal injections has become more common due to the increased availability of anti-vascular endothelial growth factor agents for the treatment of acute macular degeneration (AMO). Agents approved by the FDA for intravitreal injection to treat AMD include ranibizumab (Lucentis®: Genentech, South San Francisco, Calif.) and pegaptanib sodium (Macugen®: Eyetech Pharmaceuticals, New York, N.Y.). In addition, intravitreal bevacizumab (Avastin®: Genentech, South San Francisco, Calif.) has been widely used in an off-label application to treat choroidal neovascularization. Increased interest in developing new drugs for delivery directly into the vitreous for the treatment of macular edema, retinal vein occlusion, and vitreous hemorrhage also exists.

Currently, commercially available intravitreal injection devices lack many features that are useful in exposing the site of injection, stabilizing the device against the sclera, and/or controlling the angle and depth of injection. Many of the devices described in the patent literature, e.g., WO 2008/084064 and U.S. 2007/0005016, are also part of multi-component systems that are generally time consuming to set up and use. The increased procedure time associated with these devices may in turn increase the risk of complications. Further, having to manipulate many components by itself may increase the risk of complications due to user error. A serious complication of intraocular injection is intraocular infection, termed endophthalmitis that occurs due to the introduction of pathogenic organisms such as bacteria from the ocular surface into the intraocular environment, or trauma to the ocular surface tissues such as corneal or conjunctival abrasion.

Accordingly, new devices for performing intravitreal injections would be desirable. Ergonomic devices that simplify the injection procedure and reduce the risk of complications would be useful. Devices that accurately and atraumatically inject drugs, e.g., liquid, semisolid, or suspension-based drugs, into the eye would also be useful.

SUMMARY

Described here are devices, methods, and systems for delivering pharmaceutical formulations into the eye. The devices may be integrated. By "integrated" it is meant that various features that may be beneficial in delivering the pharmaceutical formulations into the eye, e.g., in a safe, sterile, and accurate manner, are combined into a single device. For example, features that may aid appropriate placement on the desired eye surface site, help position the device so that the intraocular space is accessed at the proper angle, help to keep the device tip stable without moving or slicing on the ocular surface once it has been positioned during the entire chug injection, adjust or control intraocular pressure, and/or help to minimize trauma, e.g., from the force of drug injection or contact or penetration of the eye wall itself, may be integrated into a single device. More specifically, the integrated devices may be used in minimizing trauma due to direct contact with the target tissue or indirectly through force transmission through another tissue or tissues such as the eye wall or vitreous gel, as well as minimizing trauma to the cornea, conjunctiva, episclera, sclera, and intraocular structures including, but not limited to, the retina, the choroid, the ciliary body, and the lens, as well as the blood vessels and nerves associated with these structures. Features that may be beneficial in reducing the risk of intraocular infectious inflammation such as endophthalmitis and those that may reduce pain may also be included. It should be understood that the pharmaceutical formulations may be delivered to any suitable target location within the eye, e.g., the anterior chamber or posterior chamber. Furthermore, the pharmaceutical formulations may include any suitable active agent and may take any suitable form. For example, the pharmaceutical formulations may be a solid, semisolid, liquid, etc. The pharmaceutical formulations may also be adapted for any suitable type of release. For example, they may be adapted to release an active agent in an immediate release, controlled release, delayed release, sustained release, or bolus release fashion.

In general, the devices described here include a housing sized and shaped for manipulation with one hand. The housing typically has a proximal end and a distal end, and an ocular contact surface at the housing distal end. A conduit in its pre-deployed state will usually reside within the housing. The conduit will be at least partially within the housing in its deployed state. In some instances, the conduit is slidably attached to the housing. The conduit will generally have a proximal end, a distal end, and a lumen extending therethrough. An actuation mechanism may be contained within the housing that is operably connected to the conduit and a reservoir for holding an active agent. A trigger may also be coupled to the housing and configured to activate the actuation mechanism. In one variation, a trigger is located on the side of the device housing in proximity to the device tip at the ocular contact surface (the distance between the trigger and device tip ranging between 5 mm to 50 mm, between 10 mm to 25 mm, or between 15 mm to 20 mm), so that the trigger can be easily activated by a fingertip while the device is positioned over the desired ocular surface site with the fingers of the same hand. In another variation, a trigger is located on the side of the device housing at 90 degrees to a measuring component, so that when the device tip is placed on the eye surface perpendicular to the limbus, the trigger can be activated with the tip of the second or third finger of the same hand that positions the device on the ocular surface. In one variation, a measuring component is attached to the ocular contact surface. In some variations, a drug loading mechanism is also included.

The actuation mechanism may be manual, automated, or partially automated. In one variation, the actuation mechanism is a spring-loaded actuation mechanism. Here the mechanism may include either a single spring or two springs. In another variation, the actuation mechanism is a pneumatic actuation mechanism.

The application of pressure to the surface of the eye may be accomplished and further refined by including a resistance component, e.g., a dynamic resistance component to the injection device. The dynamic resistance component may include a slidable element coupled to the housing. In some variations, the slidable element comprises a dynamic sleeve configured to adjust the amount of pressure applied to the eye surface. In other variations, the dynamic resistance component is configured as an ocular wall tension control mechanism.

In one variation, the injection device includes a housing sized and shaped for manipulation with one hand, the housing having a proximal end and a distal end, a resistance band at least partially surrounding the housing having a thickness between about 0.01 mm to about 5 mm, a dynamic resistance component having proximal end and a distal end, an ocular contact surface at the housing or device distal end; a conduit at least partially within the housing, the conduit having a proximal end, a distal end, and a lumen extending therethrough, and an actuation mechanism coupled to the housing and operably connected to the conduit and a reservoir for holding an active agent.

In another variation, the injection device includes integrated components and includes a housing sized and shaped for manipulation with one hand, the housing having a proximal end and a distal end, and a sectoral measuring component coupled to a distal end of the housing or device. The sectoral measuring component may have a circumference or periphery, or have a central (core) member having a proximal end, a distal end, and a circumference, and comprising a plurality of radially extending members. The injection device may also include a conduit at least partially within the housing, the conduit having a proximal end, a distal end, and a lumen extending therethrough, an actuation mechanism coupled to the housing and operably connected to the conduit and a reservoir for holding an active agent, and a dynamic resistance component.

In yet a further variation, the injection device may include a housing sized and shaped for manipulation with one hand, the housing having a wall, a proximal end and a distal end, an ocular contact surface at the housing or device distal end, a conduit at least partially within the housing, the conduit having a proximal end, a distal end, and a lumen extending therethrough, an actuation mechanism coupled to the housing and operably connected to a reservoir for holding an agent, a dynamic resistance component, and a filter coupled to the device.

Described here are also systems for delivering compositions into the eye. The systems may include a housing sized and shaped for manipulation with one hand, the housing having a proximal end and a distal end; and an ocular contact surface at the housing distal end. The conduit may at least be partially disposed within the housing, and have a proximal end, a distal end, and a lumen extending therethrough. Typically a reservoir is disposed within the housing for holding the composition that comprises an active agent. Here the systems may also include a variable resistance component coupled to the housing distal end and an air removal mechanism, where the air removal mechanism is configured to remove air from the composition before the composition is delivered into the eye.

Alternatively, the systems for delivering a composition into the eye may include a syringe body having a proximal end and a distal end, and a reservoir for containing a composition therein, and an injector attachment removably coupled to the distal end of the syringe comprising a variable resistance component. The system may further include an air removal mechanism disposed within the injector attachment, where the air removal mechanism is configured to remove air from the composition before the composition is delivered into the eye.

The systems described herein may further comprise a terminal sterilization mechanism and/or a jet control mechanism in addition to an air removal mechanism. The air removal mechanism may comprise a hydrophobic filter material having a pore size. The pore size may range from about 0.05 μm to about 50 μm, from about 0.1 μm to about 10 μm, or from about 0.2 μm to about 5 μm. In some variations the air removal mechanism comprises a plurality of hydrophobic filters. The inclusion of an air removal mechanism may be particularly beneficial when a composition comprising ranibizumab or other viscous compositions are injected into the eye.

The drug delivery systems may specifically be provided with an air or gas-resistance component (e.g., a hydrophilic filter) and a vent (e.g., a hydrophobic filter). A hydrophilic filter membrane may increase the resistance to air or gas flow and prevent it from passing through a drug conduit while also diverting it through a hydrophobic filter vent and out of the device to facilitate air or gas removal from the drug composition. The vent and gas-resistance resistance components may be adjacent to each other. The vent and gas-resistance components may also be integrally formed with the drug conduit or needle hub, or provided as separate, attachable/detachable components (with the needle hub or any part of the injection device). The gas-resistance component may be at least partially air-impermeable under any condition, or at least partially air-impermeable under certain conditions, e.g., when wetted. The gas-resistance component may prevent air in the drug composition from entering a drug conduit. The vent may provide an anti-airlock mechanism, or a gas (air)-removal mechanism. For example, the vent may comprise an air-release valve or a hydrophobic membrane.

In use, the devices deliver drug into the intraocular space by positioning an ocular contact surface of the integrated device on the surface of an eye, where the device further comprises a reservoir for holding an active agent and an actuation mechanism, and applying pressure against the surface of the eye at a target injection site using the ocular contact surface, and then delivering an active agent from the reservoir into the eye by activating the actuation mechanism. The steps of positioning, applying, and delivering are completed with one hand. In some instances, a topical anesthetic is applied to the surface of the eye before placement of the device on the eye. An antiseptic may also be applied to the surface of the eye before placement of the device on the eye.

The application of pressure against the surface of the eye using the ocular contact surface may also generate an intraocular pressure ranging between 15 mm Hg to 120 mm Hg, between 20 mm Hg to 90 mm Hg, or between 25 mm Hg to 60 mm Hg. As further described below, the generation of intraocular pressure before deployment of the dispensing member (conduit) may reduce scleral pliability, which in turn may facilitate the penetration of the conduit through the sclera, decrease unpleasant sensation associated with the conduit penetration through the eye wall during an injection procedure and/or prevent backlash of the device.

The methods may also include placing an ocular contact surface of an injection device against the eye wall, generating variable resistance to conduit advancement as the conduit is deployed through the eye wall, removing air from the composition before the composition is delivered into the eye by passing the composition through an air removal mechanism, and injecting the composition into the eye. The force required to initiate movement against the generated resistance may be about 5 gm to about 100 gm of force or about 10 gm to about 30 gm of force. In some variations, it may take about 20 gm to about 25 gm of force to initiate movement of the resistance component.

In some instances, the method may include coupling an injector attachment to a syringe body, the injector attachment comprising a variable resistance component, an air removal mechanism, an ocular contact surface, and a needle, and the syringe body having a proximal end and a distal end, and a reservoir for containing a composition therein; placing the ocular contact surface of the injector attachment against the eye wall; generating variable resistance to needle advancement as the needle is deployed through the eye wall; removing air from the composition before the composition is delivered into the eye by passing the composition through the air removal mechanism; and injecting the composition into the eye.

The drug delivery devices, components thereof, and/or various active agents may be provided in systems or kits as separately packaged components. The systems or kits may include one or more injection devices and/or injector attachments, as well as one or more active agents. The devices may be preloaded or configured for manual drug loading. When a plurality of active agents is included, the same or different active agents may be used. The same or different doses of the active agent may be used as well. The systems or kits will generally include instructions for use. They may also include anesthetic agents and/or antiseptic agents.

BRIEF DESCRIPTION OF THE DRAWINGS

FIGS. 1A-1B depict front views of exemplary ocular contact surfaces.

FIGS. 2A-2C show side views of additional exemplary ocular contact surfaces that include measuring components.

FIGS. 3A1-3A3 and FIGS. 3B1-3B3 show side views of other exemplary ocular contact surfaces.

FIG. 4A and FIGS. 4B1-4B2 depict perspective and front views of an exemplary flanged ocular contact surface.

FIGS. 5A1-5A2 and FIGS. 5B1-5B2 depict side and perspective views of exemplary flat and convex ocular contact surfaces.

FIGS. 6A1-6A2 and FIGS. 6B1-6B2 show side and front views of exemplary soft or semi-solid ocular contact surfaces.

FIGS. 7A1-7 A2, FIGS. 7B1-7B2, FIGS. 7C1-7C2, and FIGS. 7D-7E show additional exemplary ocular contact surfaces, including ocular contact surfaces having a high-traction interface.

FIGS. 15A1-15A2 show side views of exemplary bevel angles.

FIGS. 16A-16D depict cross-sectional views of exemplary conduit geometries.

FIG. 17 depicts a cross-sectional view of additional exemplary conduit geometries.

FIGS. 23A-23C depict other examples of drug loading members.

FIGS. 24A-24D show an exemplary fenestrated drug loading member.

FIGS. 25A-25B show an exemplary fenestrated drug loading member interfaced with a drug source.

FIGS. 26A-26C depicts a side, cross-sectional view of an exemplary two-spring actuation mechanism.

FIG. 27 is a side, cross-sectional view of another exemplary two-spring actuation mechanism.

FIG. 29 is a cross-sectional view of the device and two-spring actuation mechanism shown in FIG. 28.

FIG. 30 is a cross-sectional view of the device shown in FIG. 28 after the two-spring actuation mechanism has been activated.

FIGS. 33A-33B depict the device of FIG. 28 with an exemplary loading port.

FIGS. 35A-35B provide cross-sectional views of the device shown in FIG. 34. FIG. 35A show the pneumatic actuation mechanism in a pre-activated state. FIG. 35B shows the pneumatic actuation mechanism after deployment of the conduit.

FIG. 36 is a cross-sectional view of an exemplary device including a single spring actuation mechanism.

FIG. 37 is a cross-sectional view of the device shown in FIG. 36 that showing the single spring actuation mechanism after deployment of the conduit.

FIG. 38 is a side, cross-sectional view of an exemplary drug-loading piston.

FIGS. 39A-39I depict various views of exemplary device tips.

FIGS. 41A-41B provide cross-sectional views of another exemplary device having a two-spring actuation mechanism.

FIGS. 43A-43D illustrate an exemplary method of advancement of a dispensing member and drug injection.

FIGS. 45A-45J show various aspects of exemplary fine sleeve mobility control components.

FIG. 49A depicts a side view of the sleeve. FIG. 49B is a cross-sectional view of the sleeve shown in FIG. 49A taken along line B-B.

FIGS. 54A-54C show various views of another exemplary injector attachment.

FIGS. 58A-58C show an exemplary injection device. FIG. 58A is a perspective assembled view of the device, FIG. 58B is a side view of the device in FIG. 58A with components shown in more detail, and FIG. 58C is an expanded view of the domed actuator shown in FIGS. 58B and 58C.

FIG. 62A is a side view that shows some internal features of the device. FIG. 62B is an expanded cross-sectional view of the device tip.

DETAILED DESCRIPTION

Figure 7D:
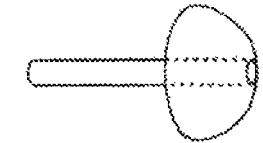

Described here are hand-held devices, methods, and systems for delivering, e.g., by injection, pharmaceutical formulations into the eye. The devices may integrate (combine) various features that may be beneficial in delivering the pharmaceutical formulations into the eye, e.g., in a safe, sterile, and accurate manner, into a single device. That is, the devices may have a modular design. As used herein, the term "modular" refers to a device formed from a combination of various components that are capable of being attached to, and detached from, the device housing. For example, e.g., various resistance components, filters (e.g., a hydrophilic and/or hydrophobic filter combination), ocular measuring components, etc., may be configured as attachable/detachable components that can be combined with a syringe housing. Thus, features that may aid appropriate placement on the eye, help positioning so that the intraocular space is accessed at the proper angle and/or depth, adjust or control ocular wall tension, and/or help to minimize trauma to the sclera and intraocular structures, e.g., from the force of injection or penetration of the sclera itself, may be integrated into a single device. The devices, in whole or in part, may be configured to be disposable. The devices may also be configured to remove air, infectious agents, and/or particulate matter from formulations or compositions prior to their injection into the eye. For example, it may be advantageous to remove air from compositions comprising ranibizumab or other viscous compositions prior to injection of these compositions into the eye. This is so that the risk of the patient developing visual disturbances such as floaters can be eliminated or minimized.

I. DEVICES

In general, the integrated or modular devices described here include a housing sized and shaped for manipulation with one hand. The housing typically has a proximal end and a distal end, and an ocular contact surface at the housing distal end. A conduit in its pre-deployed state may reside within the housing. The conduit will be at least partially within the housing in its deployed state. In some variations, the conduit is slidably attached to the housing. Additionally, the conduit will generally have a proximal end, a distal end, and a lumen extending therethrough. An actuation mechanism may be contained within the housing that is operably connected to the conduit and a reservoir for holding an active agent.

The devices or portions thereof may be formed from any suitable biocompatible material or combination of biocompatible materials. For example, one or more biocompatible polymers may be used to make, e.g., the device housing, ocular contact surface, measuring component, needle bub, slidable shield, safety clip, plunger, plunger seal, side plunger trigger actuator, etc. Exemplary biocompatible materials include without limitation, methylmethacrylate (MMA), polymethylmethacrylate (PMMA), polyethylmethacrylate (PEM), and other acrylic-based polymers; polyolefins such as polypropylene and polyethylene; vinyl acetates; polyvinylchlorides; polyurethanes; polyvinylpyrollidones; 2-pyrrolidones; polyacrylonitrile butadiene; polycarbonates (e.g., polished polycarbonate and glass filled polycarbonate); polyamides; fluoropolymers such as polytetrafluoroethylene (e.g., TEFLON™ polymer); polystyrenes; styrene acrylonitriles; cellulose acetate; acrylonitrile butadiene styrene; polymethylpentene; polysulfones; polyesters; polyimides; natural rubber; polyisobutylene rubber; polymethylstyrene; silicone; thermoplastic elastomers (e.g., Medalist® MD-145 thermoplastic elastomer (50 A durometer) and Medalist® MD-555 thermoplastic elastomer (55 A durometer), and other thermoplastic elastomers having a durometer between about 40 A and 70 A, or between about 50 A and 60 A); and copolymers and blends thereof.

In some variations, the device or a portion of the device such as the drug reservoir, plunger, housing, ocular contact surface, or measuring component, is made of a material that includes a cyclic olefin series resin. Exemplary cyclic olefin resins include without limitation, commercially available products such as Zeonex® cycle olefin polymer (ZEON Corporation, Tokyo, Japan) or Crystal Zenith® olefinic polymer (Daikyo Seiko, Ltd., Tokyo, Japan) and APEL™ cycle olefin copolymer (COC) (Mitsui Chemicals, Inc., Tokyo, Japan), a cyclic olefin ethylene copolymer, a polyethylene terephthalate series resin, a polystyrene resin, a polybutylene terephthalate resin, and combinations thereof. In one variation, it may be beneficial to use a cyclic olefin series resin and a cyclic olefin ethylene copolymer that have high transparency, high heat resistance, and minimal to no chemical interaction with a pharmacological product such as a protein, a protein fragment, a polypeptide, or a chimeric molecule including an antibody, a receptor or a binding protein.

The cyclic olefin polymers or the hydrogenation products thereof can be ring-opened homopolymers of cyclic olefin monomers, ring-opened copolymers of cyclic olefin monomers and other monomers, addition homopolymers of cyclic olefin monomers, addition copolymers of cyclic olefin monomers and other monomers, and hydrogenation products of such homopolymers or copolymers. The above cyclic olefin monomers may include monocyclic olefin monomers, and polycyclic olefin monomers including bicyclic and higher cyclic compounds. Examples of the monocyclic olefin monomers suitable for the production of the homopolymers or copolymers of the cyclic olefin monomers are monocyclic olefin monomers such as cyclopentene, cyclopentadiene, cyclohexene, methylcyclohexene and cyclooctene; lower-alkyl derivatives thereof containing, as substituent groups, 1 to 3 lower alkyl groups such as methyl and/or ethyl groups; and acrylate derivatives thereof.

Examples of the polycyclic olefin monomers are dicyclopentadiene, 2,3-dihydrocyclopentadiene, bicyclo[2,2,1]-hepto-2-ene and derivatives thereof, tricycle[4,3,0,1$^{2,5}$]-3-decene and derivatives thereof, tricyclo[4,4,0,1$^{2,5}$]-3-undecene and derivatives thereof, tetracyclo[4,4,0,1$^{2,5}$, 0$^{7,10}$]-3-dodecene and derivatives thereof, pentacyclo[6,5,1,1$^{3,6}$,0$^{2,7}$,0$^{9,13}$ 4-pentadecene and derivatives thereof, pentacyclo[7,4,0,1$^{2,5,0}$,0$^{8,13}$,1$^{9,12}$]-3-pentadecene and derivatives thereof, and hexacyclo[6,6,1,1$^{3,6}$,1$^{10,13}$,0$^{2,7}$,0$^{9,14}$]-4-heptadecene and derivatives thereof. Examples of bicyclo[2,2,1]-hepto-2-ene derivatives include 5-methyl-bicyclo[2,2,1]hepto-2-ene, 5-methoxy-bicyclo[2,2,1]-hepto-2-ene, 5-ethylidene-bicyclo[2,2,1]-hepto-2-ene, 5-phenyl-bicyclo[2,2,1]-hepto-2-ene, and 6-methoxycarbonyl-bicyclo[2,2,1-]-hepto-2-ene. Examples of tricyclo[4,3,0,1$^{2,5}$]-3-decene derivatives include 2-methyl-tricyclo[4,3,0,1$^{2,5}$]-3-decene and 5-methyl-tricyclo[4,3,0,1$^{2,5}$]-3-decene. Examples of tetracyclo[4,4,0,1$^{2,5}$]-3-undecene derivatives include 10-methyl-tetracyclo[4,4,0,1$^{2,5}$]-3-undecene, and examples of tricycle[4,3,0,1$^{2,5}$]-3-decene derivatives include 5-methyl-tricyclo[4,3,0,1$^{2,5}$]-3-decene.

Examples of tetracyclo[4,4,0,1$^{2,5}$,0$^{7,10}$]-3-dodecene derivatives include 8-ethylidenetetracyclo-[4,4,0,1$^{2,5}$,0$^{7,10}$]-3-dodecene, 8-methyl-tetracyclo-[4,4,0,1$^{2,5}$,0$^{7,10}$]-3-dodecene, 9-methyl-8-methoxy-carbonyl-tetracyclo[4,4,0,125, 07.10]-3-dodecene, 5,10-dimethyl-tetracyclo[4,4,0,1$^{2,5}$, 0$^{7,10}$]-3-dodecene. Examples of hexacyclo[6,6,1,1$^{3,6}$,1$^{10,13}$, 0$^{2,7}$,0$^{9,14}$]-4-heptadecene derivatives include 12-methyl-hexacyclo[6,6,1,1$^{3,6}$,1$^{10,13}$,0$^{2,7}$,0$^{9,14}$]-4-heptadecene and 1,6-dimethyl-hexacyclo[6,6,1,1$^{3,6}$,1$^{10,13}$,0$^{2,7}$,0$^{9,14}$]-4-heptadecene. One example of the cyclic olefin polymer is an addition homopolymer of at least one cyclic olefin monomer or an addition copolymer of at least one cyclic olefin monomer and at least one other olefin monomer (for example, ethylene, propylene, 4-methylpentene-1, cyclopentene, cyclooctene, butadiene, isoprene, styrene, or the like). This homopolymer or copolymer can be obtained by polymerizing the above monomer or monomers, for example, while using as a catalyst a known catalyst which is soluble in a hydrocarbon solvent and is composed of a vanadium compound or the like and an organoaluminum compound or the like (Japanese Patent Application Laid-Open (Kokai) No. HEI 6-157672, Japanese Patent Application Laid-Open (Kokai) No. HEI 5-43663).

Another example of the cyclic olefin polymer is a ring-opened homo polymer of the above monomer or a ring-opened copolymer of the above monomers. It can be obtained by homopolymerizing the above monomer or copolymerizing the above monomers, for example, while using as a catalyst a known catalyst such as (1) a catalyst composed of a halide or the nitrate of a platinum group metal such as ruthenium, rhodium, palladium, osmium or platinum and a reducing agent or (2) a catalyst composed of a compound of a transition metal such as titanium, molybdenum or tungsten and an organometal compound of a metal in one of Groups I to IV of the periodic table such as an organoaluminum compound or organotin compound (Japanese Patent Application Laid-Open (Kokai) No. HEI 6-157672, Japanese Patent Application Laid-Open (Kokai) No. HEI 5-43663).

The homopolymer or copolymer may contain unsaturated bonds. The homopolymer or copolymer may be hydrogenated using a known hydrogenation catalyst. Examples of the hydrogenation catalyst include (1) Ziegler-type homogeneous catalysts which are each composed of an organic acid salt of titanium, cobalt, nickel or the like and an organometal compound of lithium, aluminum or the like, (2)

supported catalysts which are each composed of a carrier such as carbon or alumina and a platinum metal such as palladium or ruthenium supported on the carrier, and (3) catalysts which are each composed of a complex of one of the above-described platinum group metal (Japanese Patent Application Laid-Open (Kokai) No. HEI 6-157672).

In variations where the injection device includes a plunger, the plunger seal (plunger tip) may be made from a thermoplastic elastomer as previously described and coated with a silicone fluid such as a Dow Corning® 360 Medical Fluid, e.g., polydimethylsiloxane. Some variations of the plunger seal may be coated with a fluoropolymer instead of a silicone polymer. Exemplary fluoropolymer coatings may comprise polytetrafluoroethylene, fluorolene, fluoroglide, and combinations thereof. Other silicone-free coatings may also be used. When the plunger seal is uncoated, it may be made from polypropylene, polyethylene, or a cyclic olefin resin, or any modifications thereof. In other variations, the inner surface of the barrel is coated. The coatings here may be the same as the ones mentioned for the plunger seal. It may be useful to include a coating on the plunger seal, inner surface of the barrel, or both, because it may impart a predictable and constant plunger release (from a resting position) and travel/glide force (force required to advance the plunger through the barrel). Employment of a coating may result in a zero or near-zero break force (force required to strut advancement of the plunger from a resting position). For example, when a coating is used, the break force may be equal to the travel force, or may be up to about 10 gm more than the travel force. Having a break force of zero, near-zero, or any one of the values mentioned above, may prevent an initial burst of fluid being injected into the eye that could potentially cause fluid waves and injure intraocular structures such as the retina. The coatings may help to prevent high, variable, and/or unpredictable initial plunger resistance, especially after prolonged storage.

In some variations, the device or a portion of the device such as the drug reservoir is made of a material that comprises polypropylene, polyethylene, or a rubber. Examples of suitable rubber materials include butyl rubbers such as butyl rubber, chlorinated butyl rubber, brominated butyl rubber, and divinylbenzene-copolymerized butyl rubber; conjugated diene rubbers such as polyisoprene rubber (high to low cis-1,4 bond), polybutadiene rubber (high to low cis-1,4 bond), and styrene-butadiene copolymer rubber; and ethylene-propylene-diene terpolymer rubber (EPDM). Crosslinkable rubber materials may also be used, and may be made by kneading the above-described rubber materials together with additives such as a crosslinking agent, a filler and/or reinforcement, a colorant, or an age resister.

In some variations, the biocompatible material is a biodegradable polymer. Nonlimiting examples of suitable biodegradable polymers include cellulose and ester, polyacrylates (L-tyrosine-derived or free acid), poly(β-hydroxyesters), polyamides, poly(amino acid), polyalkanotes, polyalkylene alkylates, polyalkylene oxylates, polyalkylene succinates, polyanhydrides, polyanhydride esters, polyasprutimic acid, polylactic acid, polybutylene digloclate, poly(caprolactone), poly(caprolactone)/poly (ethylene glycol) copolymers, polycarbone, L-tyrosin-derived polycarbonates, polycyanoacrylates, polydihydropyrans, poly(dioxanone), poly-p-dioxanone, poly(ε-caprolactone-dimethyl trimethylene carbonate), poly (esteramide), polyesters, aliphatic polyesters, poly(ether-ester), polyethylene glycol/poly(orthoester) copolymers, poly(glutarunic acid), poly(glycolic acid), poly(glycolide), poly(glycolide)/poly(ethylene glycol) copolymers, poly(lactide), poly(lactide-co-caprolactone), poly(DL-lactide-co-glycolide), poly(lactide-co-glycolide)/poly(ethylene glycol) copolymers, poly(lactide)poly(ethylene glycol) copolymers, polyphosphazenes, polyphosphesters, polyphophoester urethanes, poly(propylene fumarate-co-ethylene glycol), poly (trimethylene carbone), polytyrosine carbonate, polyurethane, terpolymer (copolymers of glycolide lactide or dimethyltrimethylene carbonate), and combinations, mixtures or copolymers thereof.

Additives may be added to polymers and polymer blends to adjust their properties as desired. For example, a biocompatible plasticizer may be added to a polymer formulation used in at least a portion of a device to increase its flexibility and/or mechanical strength, or to provide color contrast with respect to the surface of the eye. In other instances, a biocompatible filler such as a particulate filler, fiber and/or mesh may be added to impart mechanical strength and or rigidity to a portion of a device.

The devices described here can be manufactured, at least in part, by injection or compression molding the above-described materials.

In some instances, it may be beneficial to include a removably attached or integrated viewing and/or magnifying element on the device. For example, a magnifying glass and/or illumination source such as a LED light may be removably attached to the device to facilitate the visualization of the tip of the device and the injection site. The improved visualization may help to more precisely and safely position the device at a target location, e.g., about 3.5 mm to 4 mm posterior to the corneo-scleral limbus, so that complications of intraocular injection such as retinal detachment, ciliary body bleeding, or trauma to the intraocular lens can be potentially avoided. The magnifying glass may be made from any suitable material, e.g., it may be made from any suitable non-resorbable (biodegradable) material previously described, but will typically be light-weight so that it does not affect the balance of the injection device. The magnifying glass and/or illumination source, e.g., the LED, may be disposable.

Housing

The housing of the device generally contains the drug reservoir and actuation mechanism. In its first, non-deployed state (pre-deployed state), the conduit may reside within the housing. The housing may be of any suitable shape, so long as it allows grasping and manipulation of the housing with one hand. For example, the housing may be tubular or cylindrical, rectangular, square, circular, or ovoid in shape. In some variations, the housing is tubular or cylindrical, similar to the barrel of a syringe. In this instance, the housing bas a length between about 1 cm and about 15 cm, between about 2.5 cm and about 10 cm, or about 4 cm and about 7.5 cm. For example, the housing may have a length of about 1 cm, about 2 cm, about 3 cm, about 4 cm, about 5 cm, about 6 cm, about 7 cm, about 8 cm, about 9 cm, about 10 cm, about 11 cm, about 12 cm, about 13 cm, about 14 cm, or about 15 cm. The surface of the housing may also be texturized, roughened, or otherwise modified in certain areas, e.g., with protrusions, ridges, etc., to aid the gap and or manipulation of the housing by the user. Grips may be associated with any one of the actuation mechanisms further described below. The grips are generally configured to help the operator maintain a steady grip on the device using, e.g., two, three or four fingers. The plunger actuation lever may be located on the device housing in the close proximity of the grip, for example, integrated with the grip, or between about 1.0 mm and 10 mm of the grip, so that the operator is able to easily use the fingers holding the device to actuate, e.g., slide, the actuation lever while maintaining a steady grip and without compromising the hold/control of the device. The distance that the actuation lever may travel may be between about 2.0 mm and about 8.0 mm, or between about 1.0 mm and about 15 mm). Maintaining a steady grip while actuating the drug injection mechanism is useful because it helps to localize the injection site on the eye surface with about a 0.5 mm precision accuracy.

In some variations, the housing comprises a syringe barrel having a distal end that includes a luer. The luer may be of any suitable type, e.g., slip-tip, luer-lock, or luer-snap type. When the luer is of the luer lock type, it may interface with a drug conduit by twisting the drug conduit on/off. When the luer is of the luer-snap type, it may comprise a raised edge on the outside surface of the luer tip that may interlock with a raised ridge located on the inside surface of the hub of a drug conduit to form a male-female type of connection. The luer-snap connection may enhance the connection strength between the housing (having a reservoir disposed within) and a drug conduit as compared to the slip-tip type of connection, but without the rigid lock that is achieved with a luer-lock type of connection.

Some variations of the luer-snap connector may provide tactile feedback to ensure that the drug conduit has been appropriately positioned and stably interfaced with the housing (e.g., that the hub of the drug conduit has been placed far enough onto the luer to prevent its accidental detachment during the drug injection procedure.

The luer-snap connector may further comprise a self-positioning mechanism to ensure the hub of the drug conduit has been stably positioned in the right location on the luer. The self-positioning mechanism may be a combination of interlocking raised ridges, where one ridge is located on the external surface of the luer and the other ridge is located on the internal surface of the drug conduit hub, but at least one of the ridges has a shallow leading slope and a steep trailing slope that may allow the drug conduit to self-position and snap into place once the ridges have been advanced past each other.

The housing may be made from any suitable material. For example, and as previously stated, the components of the device may be made from any suitable biocompatible material or combination of biocompatible materials. Materials that may be beneficial in making the housing include, without limitation, a cyclic olefin series resin, a cyclic olefin ethylene copolymer, a polyethylene terephthalate series resin, a polystyrene resin, and a polyethylene terephthalate resin. In one variation, it may be beneficial to use a cyclic olefin series resin and a cyclic olefin ethylene copolymer that have a high transparency, a high heat resistance, and minimal to no chemical interaction with a pharmacological product such as a protein, a protein fragment, a polypeptide, or a chimeric molecule including an antibody, a receptor or a binding protein. Additional materials that may be beneficial in making the housing include, without limitation, fluoropolymers; thermoplastics such as polyetheretherketone, polyethylene, polyethylene terephthalate, polymethane, nylon, and the like; and silicone. In some variations, the housing may be made from a transparent material to aid conformation of conduit deployment and/or drug delivery. Materials with suitable transparency are typically polymers such as acrylic copolymers, acrylonitrile butadiene styrene (ABS), polycarbonate, polystyrene, polyvinyl chloride (PVC), polyethylene terephthalate glycol (PETG), and styrene acrylonitrile (SAN). Acrylic copolymers that may be useful include, but are not limited to, polymethyl methacrylate (PMMA) copolymer and styrene methyl methacrylate (SMMA) copolymer (e.g., Zylar 631® acrylic copolymer).

Ocular Contact Surfaces

The devices described herein generally include an atraumatic ocular contact surface at the distal end of the housing. In some variations, the ocular contact surface is fixedly attached to the housing proximal end. In other variations, the ocular contact surface is removably attached to the housing proximal end. The ocular contact surface will typically be sterile. In some instances, the ocular contact surface is disposable. In use, the ocular contact surface of the device is placed on the surface of the eye.

The ocular contact surface may be of any suitable configuration, e.g., size, shape, geometry, etc., as long as it allows atraumatic placement of the device on the ocular surface. In some variations, the ocular contact surface is ring-shaped (e.g., FIGS. 1A-1B). When the ocular contact surface takes the shape of a ring, it may have a diameter of about 0.3 mm to about 8 mm, about 1 mm to about 6 mm, or about 2 mm to about 4 mm. In other variations, the ocular contact surface is oval or circular in shape.

More specifically, as shown in the front views of FIGS. 1A-1B, the device tip comprises a ring-shaped ocular contact surface where the distance between the inner diameter and outer diameter of the ring forms a rim. In this instance, the ring-shaped ocular contact surface may be configured as having a wider ocular contact surface (10) (rim) and smaller internal opening (12) (FIG. 1A), or narrower ocular contact surface (14) (rim) with larger internal opening (16) (FIG. 1B). The dispensing member (conduit) may be an injection needle that is hidden inside and protected by the device tip. A membrane may also be provided that extends across the internal opening, and which may be flush with the ocular contact surface or recessed within the lumen of the device tip where the injection needle resides.

As shown in FIGS. 39A-39B, the tip of the dispensing member may be recessed relative to end of the device housing tip comprising the ocular contact surface in the resting state, so that when the device tip is placed in contact with any surface such as the skin or the eye wall, the tip of the dispensing member is separated from the surface by a distance marked with arrows in FIG. 39B. This distance may ensure that the dispensing member tip does not come in direct contact with any surface prior to the injection procedure, which prevents accidental bacterial contamination of the dispensing member from sources such as skin secretions, ocular secretions or tears, and minimizes the risk of introducing intraocular infectious agents during the intraocular injection procedure that may cause endophthalmitis.

In some variations, the tip of the dispensing member is recessed relative to, and is separated from the closest end of the device housing by a distance ranging from about 0.01 mm to about 10 mm, from about 0.1 mm to about 5 mm, or from about 0.5 mm to about 2 mm.

An enclosure may be provided on the distal end of the device that completely covers the dispensing member to prevent it from contacting eye lashes or eye lids, and to prevent it from being exposed to potentially contaminated surfaces at all times. Here the dispensing member may extend from the enclosure and penetrate the eye wall and into an eye cavity without being exposed to ocular appendages such as eyelids or eye lashes that harbor bacteria. The eye is an immune-privileged organ and, thus, any bacterial contamination has the propensity to result in intraocular infection. Enclosure of the dispensing member may protect it from contacting ocular appendages harboring bacteria, thereby minimizing the risk of sight-threatening intraocular infection. In one variation, the dynamic sleeve (further described below) is configured as the sterile enclosure. The dynamic sleeve may also be covered by a membrane that prevents ocular surface tears from entering the orifice of the device tip and potentially contaminating the dispensing member before it is deployed.

In other variations, the outer surface of the device tip may be configured to include a raised surface that forms a seal around the exit site of the dispensing member from the device tip. The seal may function to prevent ocular tears from circulating through the potential injection site once the device tip has been positioned on the eye surface. The raised surface may be configured to be annular, oval, square, rectangular, triangular, or any other suitable shape or geometry.

In another variation, the ocular contact surface of the device tip that comes in direct contact with the eye surface is ring-shaped, where there is a clearing between the internal wall of the device housing and the dispensing member of about 360 degrees, which is marked by arrows in FIG. 39C. Here, if the ring-shaped ocular interface surface becomes contaminated with an infectious agent and is placed onto the eye surface, the dispensing member will come in contact and penetrate through the eye surface that is separated from the contaminated device tip by the area of dealing, which prevents accidental bacterial contamination of the dispensing member and minimizes the risk of introducing intraocular infection that may cause endophthalmitis. In contrast, the lack of such clearing around the dispensing member, as shown in FIG. 39D, may allow accidental infectious contamination of the device tip at the site of injection.

In some variations, there is a clearing between the internal wall of the device housing and the dispensing member ranging from about 0.1 mm to about 5 mm, from about 0.3 mm to 3 mm, or from about 0.5 mm to about 2 mm.

In other variations, there is a solid membrane or partition (105) that separates the tip of the dispensing member (107) from the external environment, as shown in FIG. 39E, where the membrane or partition may be water-impermeable and/or be air-impermeable. The membrane or partition may ensure that there is no air movement in or out of the device creating an air seal and maintaining a certain constant air pressure inside the device.

Furthermore, the membrane or partition may ensure that the dispensing member tip does not come in contact with any source of accidental bacterial contamination such as tears and ocular secretions prior to the injection procedure, which prevents accidental bacterial contamination of the dispensing member and minimizes the risk of introducing intraocular infection during the intraocular injection procedure that may cause endophthalmitis.

The membrane or partition that separates the tip of the dispensing member from the end of the device housing may comprise a material selected from the group consisting of biocompatible and non-biodegradable materials including without limitation, methylmethacrylate (MMA), polymethylmethacrylate (PMMA), polyethylmethacrylate (PEM), and other acrylic-based polymers; polyolefins such as polypropylene and polyethylene; vinyl acetates; polyvinylchlorides; polyurethanes; polyvinylpyrollidones; 2-pyrrolidones; polyacrylonitrile butadiene; polycarbonates; polyamides; fluoropolymers such as polytetrafluoroethylene (e.g., TEFLON™ polymer); or fluorinated ethylene propylene (FEP); polystyrenes; styrene acrylonitriles; cellulose acetate; acrylonitrile butadiene styrene; polymethylpentene; polysulfones; polyesters; polyimides; natural rubber; polyisobutylene rubber; polymethylstyrene; silicone; derivatives and copolymers and blends thereof.

In some variations, the membrane or partition (30) may be recessed inside the device tip so that when the device tip is placed in contact with any surface such as the skin or the eye surface, the said membrane or partition is separated from the said surface by a distance marked with arrows, as depicted in FIG. 39E. The distance may ensure that the dispensing member tip (31) does not come in direct contact with any surface prior to the injection procedure, which prevents accidental bacterial contamination of the dispensing member from sources such as skin secretions, ocular secretions or tears, and minimizes the risk of introducing intraocular infection during the intraocular injection procedure that may cause endophthalmitis.

The membrane or partition may be recessed relative to and separated from the end of the device housing at the ocular interface by a distance ranging from about 0.01 mm to about 10 mm, from about 0.1 mm to about 5 mm, or from about 0.5 mm to about 2 mm.

In further variations, a measuring component (32) (further described below) may be recessed relative to the end of the device housing (33) at the ocular contact surface (FIGS. 39F-39H), so that when the device tip (34) comes in contact with the eye surface (35) (FIG. 39I), the measuring component (32) does not come in contact with the eye surface (35). This configuration may minimize the risk of trauma to the delicate tissue covering the eye surface such as the non-keratinizing epithelia of the cornea and conjunctiva. Avoiding direct contact between the measuring member and the ocular surface may be beneficial in minimizing the risk of ocular surface trauma such as corneal or conjunctival abrasion, which prevents further serious complications such as bacterial injection including corneal ulcer. In alternative variations, the tip of the measuring member (32) may be angled away or towards the eye (FIGS. 39G and 39H, respectively). The measuring component may be recessed relative to the end of the device housing by a distance ranging from about 0.01 mm to about 5 mm, from about 0.01 mm to about 3 mm, or from about 0.5 mm to about 2 mm.

In some variations, as shown in FIGS. 2A-2C, the device tip may also comprise a ring-shaped ocular contact surface and a measuring means that helps to determine the proper location of the injection site at a certain distance relative to and perpendicular to the corneo-scleral limbus. In one variation, the measuring component (20) is located on one side of the device tip (22). In another variation, more than one measuring component is located on more than one side of the device tip. Here the tip of the measuring component is flat (FIG. 2C) and does not substantially protrude above the ocular contact surface. In other variations, the tip of the measuring component is raised (FIGS. 2A-2B) above the ocular contact surface, which enables it to prevent the eyelid from sliding over and on top of the measuring component, thus preventing the eyelid from coming into contact with the sterile ocular contact surface of the device tip or the dispensing member. This in turn may reduce the risk of accidental contamination and intraocular infection during the injection procedure.

In other variations, the ocular contact surface comprises a flange (e.g., FIGS. 3A1-3A3, FIGS. 3B1-3B3, FIG. 4A, and FIGS. 4B1-4B2). The flange may provide an expanded contact surface between the device tip and the eye surface, thus increasing the stability of the device when it is positioned on the ocular surface, and decreasing the pressure force per unit area of the device-ocular interface. Reducing the pressure force per unit area of the device-ocular interface in turn may reduce the potential for conjunctival damage by the device tip when it is pressed against the eye wall. Avoiding such conjunctival damage is desirable because the conjunctiva is covered by delicate non-keratinizing epithelium containing multiple sensory nerve endings and pain receptors.

In some variations, the flange may have thin edges that come in contact with the ocular surface, and which allows the eye lid to travel over and on top of the flange, but prevents the eye lid from coming in contact with the sterile ocular contact surface of the device tip. The ocular contact surface may also be a ring-shaped flange (e.g., FIGS. 4A and 4B1-4B2). Such a ring-shaped flange may also prevent the eye lid from coming in contact with the sterile ocular contact surface of the device tip.

More specifically, as shown in FIG. 3, the flange may have a thin edge (FIG. 3A1), which allows the eye lid to slide over the said flange and come in contact with the shaft of the device tip. In an alternative variation, the said flange may be thick (FIG. 3B1) in order to prevent the eye lid from sliding over it and keeping it from coming in contact with the device shaft, thus preventing inadvertent contamination of the injection site. When the flange at the ocular contact surface of the device tip is thick, its edges, such as those at its ocular surface may be rounded in order to prevent accidental damage to the ocular surface tissues such as the conjunctiva that is covered with delicate non-keratinizing epithelium rich in nerve endings and pain receptors. In alternative variations of the device tip, the ocular contact interface may be flat (FIGS. 3A1 and 3B1), convex (FIGS. 3A2 and 3B2), or concave (FIGS. 3A3 and 3B3) to reduce the chance of accidental damage to ocular surface tissues such as the conjunctiva while providing a means of applying a force onto the eye wall and increasing intraocular pressure in order to facilitate the needle penetration through the eye wall, as well as to partially immobilize the eye during the injection procedure by providing the traction interface of the ocular contact surface. FIGS. 4A and 4B1-4B2 illustrate perspective and front views of a flanged ocular contact surface.

In yet further variations, the ocular contact surface may be configured to be flat, convex, concave, or slanted (e.g., FIGS. 5 and 7). In FIGS. 5A1-5A2, the device tip has a flat ocular contact surface. In an alternative variation, the device tip has a protruding or convex ocular contact surface (FIGS. 5B1-5B2), which may improve contact between the internal opening of the device tip and the ocular surface when the device tip is pressed against the eye wall resulting in eye wall indentation. In yet another variation, the ocular contact surface of the device tip is indented or concave, which reduces the risk of accidental damage to the ocular surface tissue such as the conjunctiva. Such configurations of the ocular contact surface of the device tip may reduce the chance of accidental damage to ocular surface tissues, such as the conjunctiva, while providing a means of applying a pressure force onto the eye wall and increasing the intraocular pressure in order to facilitate the needle penetration through the eye wall, as well as to partially immobilize the eye during the injection procedure by providing the device-ocular surface traction interface.

Figure 7E:
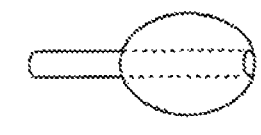

More specifically, as shown in FIG. 7, the ocular contact surface may be flat and perpendicular to the long axis of the said device (FIGS. 7A1-7A2), or is flat and slanted relative to the long axis of the said device (7B1-7B2) (e.g., oriented at an angle other than 90 degrees, such as from about 45 degrees to about 89 degrees relative to the long axis of the device), or is convex and perpendicular to the long axis of the device (FIG. 7C1), or is convex and slanted relative to the long axis of the device (FIG. 7C2), or is rounded (FIG. 7D), or is oval (FIG. 7E). In one variation, the ocular interface is rounded or oval (e.g., similar to the tip of a Q-tip). The thickness of the ocular contact surface may be from about 0.01 mm to about 10 mm, from about 0.05 mm to about 5 mm, or from about 0.1 mm to about 2 mm.

The ocular contact surface may include one or more features (e.g., slip-reducing features) that help to stabilize it on the eye surface (e.g., prevent slippage on the eye surface). For example, in one variation, the ocular contact surface comprises one or a plurality of traction elements, e.g., bumps, ridges, raised details above the plane of the ocular contact surface, etc., that increase surface traction of the ocular contact surface on the eye surface without being abrasive. Such an ocular contact surface may provide a mild-, medium-, or high-traction interface to stabilize the device tip on the surface of the eye and prevent it from moving during intraocular drug delivery. In another variation, the ocular contact surface includes an adherent interface such as a suction mechanism. Varying the type of material used to make the ocular contact surface may also help prevent its slippage on the ocular surface.

The materials used to make the ocular contact surface may also help to prevent abrasion, scratching, or irritation of the eye surface. Exemplary non-abrasive materials that may be employed include without limitation, nylon fiber, cotton fiber, hydrogels, spongiform materials, Styrofoam materials, other foam-like materials, silicone, plastics, PMMA, polypropylene, polyethylene, fluorinated ethylene propylene (FEP), and polytetrafluoroethylene (PTFE). Thermoplastic elastomers, e.g., silicone, may be beneficial to use when making the ocular contact surface. The materials may be smooth-hard, semi-hard, or soft, and may be beneficial in preventing conjunctival abrasion, subconjunctival hemorrhage during transcleral needle deployment, or other accidental trauma to the ocular surface tissues (FIG. 6). For example, the material of the ocular contact surface may have a durometer ranging between about 30 A and about 60 A. Materials typically used in contact lens manufacturing may also be employed.

In some variations, the edges of the ocular contact surface are also rounded to prevent accidental damage to the ocular surface tissues such as the conjunctiva that is covered with delicate non-keratinizing epithelium rich in nerve endings and pain receptors. In this instance, as shown in FIG. 6, the ocular contact surface may have a circumference corresponding to the circumference of the device tip (FIGS. 6A1-6A2). In other variations, the circumference of the ocular contact surface may protrude beyond the circumference of the shaft of the device tip, thus forming a flange (FIGS. 6B1-6B2). The flange may increase the ocular contact surface of the device tip while maintaining the slim profile of the shaft of the tip, enabling its easy insertion into the interpalprebral fissure of the eye.

The ocular contact surface may also provide an interface surface that is pliable or deformable, and which conforms to the surface of the eye when placed against the said eye surface during the intraocular drug delivery procedure. The surface of the eye that comes in direct contact with the said interface surface of the disclosed device includes, but is not limited to, the surface of the eye over the pars plana region defined as the circumferential area between about 2 mm and 7 mm posterior to and surrounding the limbus, or the corneo-scleral limbal area between about 2 mm anterior and about 2 mm posterior to and circumferential to the limbus. The interface surface that conforms to the curvature of the surface of the eye may enable the formation of an optimal contact interface between the device and the eye, and may ensure sterility of the intraocular drug delivery process and immobilization of the eye, which in turn may enhance the safety of the injection procedure. Examples of ocular interface materials for the device are those that are generally able to conform to the surface of the eye (that is deformable or pliable) particularly to the curvature of the external surface of the eye in the area of pars plana about 2-5 mm posterior to the corneo-scleral limbus for intravitreal drug application, as well as to the area of the corneo-scleral limbus for anterior chamber drug applications. As previously stated, materials that are non-abrasive to the non-keratinizing conjunctival and corneal epithelium of the ocular surface may be used. Specifically, the materials and their configurations (e.g., foam, braid, knit, weave, fiber bundle, etc.), may include those capable of forming medium- or high-traction surfaces (e.g., hydro gels or cotton) that enable immobilization of the eye globe during the injection procedure.

In some variations, the material of the ocular contact surface changes its properties upon contact with fluid, e.g., by reducing its traction coefficient such as in cotton fiber, which may reduce the risk of conjunctival abrasion upon contact of the ocular contact surface with the eye surface. In other variations, the material comprising ocular contact surface does not change its physical and chemical properties when exposed to fluid that covers the surface of the eye such as tears.

The ocular contact surfaces described here may be beneficial in preventing conjunctival and/or episcleral bleeding during intraocular needle injection. For example, a device comprising a ring-shaped ocular interface may be pressed against the eye wall, which in turn applies pressure to the conjunctival and episcleral vessels, thereby reducing blood flow therethrough. Given the reduced blood flow through these vessels, the risk of subconjunctival bleeding during intraocular injection procedure may be reduced. Following the completion of intraocular drug application, the needle is withdrawn, but the ring-shaped tip may remain pressed against the eye wall, thus applying continuous pressure onto the conjunctival and episcleral vessels and further reducing the risk of bleeding and/or minimizing the extent of bleeding.

In some variations, the device comprises an ocular contact surface that functions as a drug reservoir. Here a drug may be incorporated into, or coated on, the material of the ocular contact surface. The drug may then diffuse, leech, etc., from the ocular contact surface onto the surface of the eye. Exemplary materials for inclusion of drugs are hydro gels and their derivatives.

The ocular contact surface may also cover the dispensing member (conduit) such as an injection needle (e.g., it may be a cap that entirely covers the needle), which may enable the injector to apply pressure onto the eye by pressing the tip (e.g., the distal end of the cap) against the eye wall. This in turn may increase the intraocular pressure before the needle comes in contact with the eye wall and, thus, may facilitate needle penetration because the eye wall is more taut ill comparison to an eye wall being penetrated by a needle on a conventional syringe. Needle penetration is typically more difficult with a conventional syringe because the lower intraocular pressure that is generated makes the eye wall more deformable and mobile. In addition, the device tip that covers the dispensing member (conduit), such as an injection needle, may also protect the said dispensing member from being contaminated by its accidental contact with eye lids. The cover may be made from any suitable material. Exemplary materials include without limitation, polyethylene, polycarbonate, polypropylene, acrylonitrile butadiene styrene polymers, Delrin® acetal homopolymers, polyurethane, acrylic polymers, polyether ether ketone, and combinations thereof. In one variation, the cover is made from polycarbonate.

Intraocular Pressure Control Mechanisms (Ocular Wall Tension Control Mechanisms)

The control of intraocular pressure (IOP) during the drug delivery procedure, e.g., intraocular injection or intravitreal injection, may be beneficial. The application of limited intraocular pressure before deployment of the dispensing member (conduit) may reduce scleral pliability, which in turn may decrease any unpleasant sensation on the eye surface during an injection procedure and/or prevent backlash of the device. The term "backlash" typically refers to the inability of the conduit to smoothly penetrate the eye wall due to scleral pliability and elasticity, which makes the sclera indent to a certain point and push the conduit and device backwards before the conduit penetrates into and through the sclera. Accordingly, the devices described here may include one or more IOP control mechanisms, also referred to herein as ocular wall tension control mechanisms. This is because ocular wall tension is proportionally related to, and determined in part, by intraocular pressure. Other factors that may effect wall tension are scleral thickness and rigidity, which can be variable due to patient age, gender, and individual variations.

The IOP mechanisms may control IOP during the placement and positioning of the device tip at the target location on the ocular surface, and/or intraocular or intravitreal positioning of the dispensing member (conduit) during intraocular or intravitreal injection of a drug. For example, the IOP mechanisms may control IOP prior to and during the intraocular or intravitreal positioning of a dispensing member being used for trans-scleral or trans-corneal penetration. Once penetration of the ocular surface by the dispensing member occurs, IOP will typically decrease. This decrease in IOP may occur immediately after penetration of the ocular surface by the dispensing member.

In some variations, the IOP control mechanisms allow (enable) the devices to generate an IOP between 15 and 120 mm Hg during the placement and positioning of the device tip at a target location on the ocular surface, and/or intraocular positioning of the dispensing member. In other variations, the IOP control mechanisms allow (enable) the devices to generate an IOP between 20 and 90 mm Hg during the placement and positioning of the device tip at a target location on the ocular surface, and/or intraocular positioning of the dispensing member. In yet further variations, the IOP control mechanisms allow (enable) the devices to generate an IOP between 25 and 60 mm Hg during the placement and positioning of the device tip at a target location on the ocular surface, and/or intraocular positioning of the dispensing member.

The IOP control mechanisms may also allow (enable) the devices to maintain the IOP between 10 and 120 mm Hg, or between 15 and 90 mm Hg, or between 20 and 60 mmHg during any duration of time of the intraocular injection procedure. In some variations, the drug injection rate is slowed or completely aborted by the device if the intraocular pressure exceeds a certain predetermined value, for example 120 mm Hg, or 60 mm Hg, or 40 mm Hg. Here the IOP control mechanism may be configured to detect a IOP level during the intraocular drug injection of, e.g., 90 mmHg, or 60 mm Hg, or 40 mm Hg.

The IOP control mechanism may include a spring, or it may comprise a mechanical or an electrical control mechanism. In general, the IOP control mechanism will be configured to balance the frictional forces of the injection plunger and fluid injection resistance pressure (force required to push fluid through the needle into the pressurized eye fluids). The IOP control mechanisms may be coupled to the device housing and actuation mechanism in a manner that allows automatic adjustment of the force of dispensing member deployment and plunger advancement. That is, the IOP control mechanism may be configured to affect a predetermined level of force of the dispensing member and a predetermined intraocular pressure level. Again, use of the IOP control mechanisms may generate higher than the resting IOP prior to dispensing member deployment so that scleral elasticity and the potential for device backlash is decreased, and to facilitate scleral penetration by the dispensing member.

Figure 40:
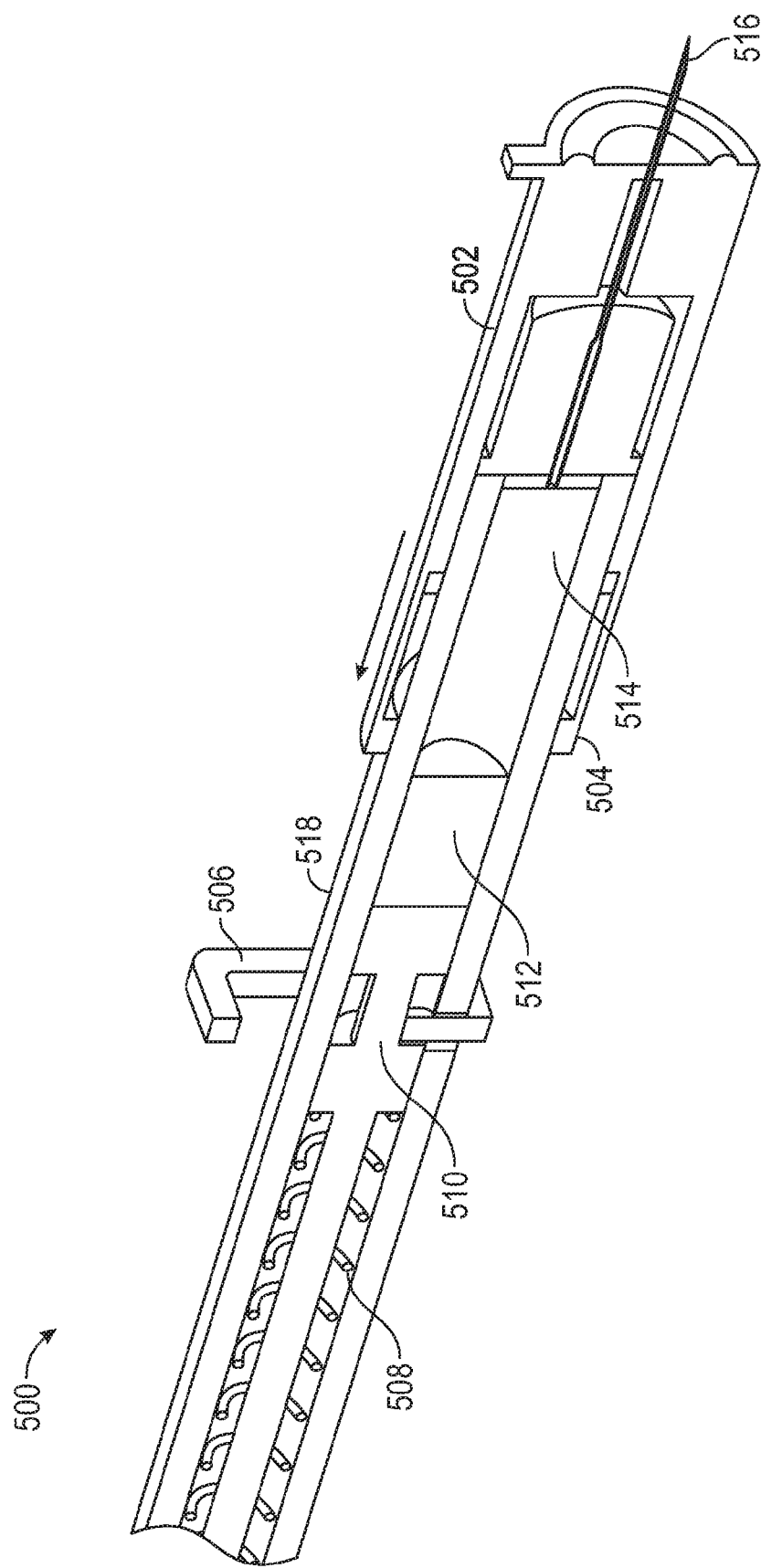
FIG. 40 shows an exemplary device with a sliding cap.

In one variation, the IOP control mechanism is a pressure relief valve that bypasses the injection stream once a maximum pressure is reached. In another variation, the IOP mechanism is a pressure accumulator that dampens the IOP within a specified range. Some variations of the IOP control mechanism may include a pressure sensor. In yet another variation, the IOP control mechanism includes a slidable cap or shield that covers the dispensing member prior to its deployment, but which may slide or retract along the surface of the device housing to expose, deploy, or advance the dispensing member e.g., upon attainment of a predetermined IOP level. Sliding of the cap may be manually adjustable, e.g., using a dial, or automatically adjustable, step-wise, or incremental in nature. For example, as shown in FIG. 40, integrated injection device (500) includes, among other elements, a cap (502), a stop (504), a trigger (506), a spring (508), a plunger (510), a seal (512), a drug reservoir (514), a needle (516), and a syringe (518). In use, when cap (502) is placed against the ocular surface and pressure applied against the ocular surface, cap (502) slidably retracts proximally (in the direction of the arrow) to stop (504) as the syringe (518) and needle (516) are advanced. The trigger (506), e.g., a lever, may then be depressed to release spring (508), which advances plunger (510) and seal (512) to inject drug from the drug reservoir (514) through needle (516). Once the drug is injected, cap (502) slides back over the needle (516).

A locking mechanism may also be used to prevent sliding of the cap, cover or ocular contact surface, or prevent deployment of the dispensing member until a predetermined IOP is reached. The locking mechanism may also be used to prevent sliding of the cap, cover, or ocular contact surface if a predetermined IOP is not reached. For instance, the locking mechanisms included on the devices described here that include a slidable cover, cap, etc., may be released manually or automatically when the IOP reaches a predetermined level, such as between 20 mm Hg and 80 mm Hg. Such locking mechanisms may include without limitation, high traction surfaces, locking pins, interlocking raised ridges, or any other type of locking mechanism that prevents the tip of the device, e.g., the cap or cover of the device, from sliding and thus exposing the needle.

In yet further variations, the IOP control mechanism includes a high-traction surface or raised ridges on the cap, cover, shield, or ocular contact surface situated over the dispensing member. Such features may be disposed on the inner surface of the cap, cover, shield, or ocular contact surface and configured so that upon sliding in the proximal direction, the high-traction surface or raised ridges mate with corresponding structures (e.g., crimps, dimples, protrusions, other raised ridges) on the surface of the device housing or other appropriate device component to provide resistance of the cap, cover, shield, or ocular contact surface against the eye wall (thus increasing ocular wall tension and IOP). In this instance, the IOP control mechanism comprises a resistance component, as further described below. As stated above, the cap, cover, shield, or ocular contact surface may be configured so that sliding is manually or automatically adjustable, step-wise, or incremental in nature. When raised ridges are employed, any suitable number may be used, and they may be of any suitable size, shape, and geometry. For example, the raised ridges may be circumferentially disposed within the cap, cover, or ocular contact surface. In some instances, the raised ridges are configured with surfaces of differing slope. For example, the distal surface may be configured to be steeper than the proximal surface. With this design, incremental sliding and incremental increases in IOP may be generated when the cap, cover, shield, or ocular contact surface is slid proximally, but sliding of the cap, cover, shield, or ocular contact surface back over the dispensing member may also be accomplished due to the decreased slope of the proximal ridge surface.

IOP control mechanisms that provide resistance may slide and expose a needle secured to the housing, e.g., a syringe, when the force exerted on the shield is transmitted onto the eye wall. The exerted force may create an intraocular pressure of between about 10 mm Hg to about 150 mm Hg, between about 12 mm Hg and about 120 mm Hg, between about 15 mm Hg and about 60 mm Hg, or between about 15 mm Hg and about 40 mm Hg.

Resistance Component

The application of pressure to the surface of the eye may be accomplished and further refined by including a resistance component, e.g., a dynamic resistance component to the injection device. The dynamic resistance component may be configured to detach from the injection device. The dynamic resistance component may include a slidable element and/or a fully rotatable (e.g., rotate 360 degrees) or partially rotatable (e.g., rotate less than 360 degrees) element coupled to the housing. The dynamic resistance component may be configured so that it can be fully or partially rotated about the long axis of the device using only one finger (e.g., the middle finger) while holding the device with the thumb and the index finger of the same hand. In some variations, the slidable element comprises a dynamic sleeve configured to adjust the amount of pressure applied to the eye surface, as further described below. As previously stated, certain variations of the ocular wall tension control mechanism function as dynamic resistance components. A force between about 5 gm to about 100 gm or about 10 gm to about 30 gm may be needed to initiate movement of the slidable elements against resistance that is generated by the slidable elements. In some variations, it may take about 20 gm to about 25 gm of force to initiate movement of the slidable elements. In other variations, it may take about 3 gm to about 30 gm of force to initiate movement of the slidable resistance component.

The dynamic resistance component may also be configured as a dynamic sleeve. Similar to the slidable cap previously described, the dynamic sleeve may be configured to increase intraocular pressure and tension of the eye wall prior to needle injection. However, the dynamic sleeve is capable of being manually manipulated to thereby adjust the amount of pressure applied on surface of the eye (and thus, the amount of eye wall tension). Having the ability to manually adjust the applied pressure may allow the injector (user) to have improved control of the injection site placement and the injection angle, and also enhances the user's ability to stably position the device on the ocular surface prior to needle deployment. In general, the dynamic sleeve is designed to enable the user to precisely position the device tip at the targeted site on the eye surface and to firmly press the device tip against the eye wall to increase wall tension and intraocular pressure. The dynamic sleeve may be used to raise intraocular pressure to a predetermined level, as described above, prior to the initiation of sleeve movement and needle deployment. It should be understood that the terms "dynamic sleeve," "sleeve," "slidable sleeve," "dynamic sleeve resistance control mechanism," and "sleeve resistance mechanism" are used interchangeably throughout. In some variations, the dynamic sleeve is removable or detachable from the drug conduit, rendering the drug conduit completely uncovered. In other variations, the dynamic sleeve is fixedly attached to the drug conduit and at least partially covers the conduit. In yet further variations, the dynamic sleeve may be rigid or non-deformable. The dynamic sleeve may be configured such that when a pulling force (e.g., retraction away from the eye) is exerted on the sleeve, this movement may facilitate needle exposure and reduce the amount of pressure force (down to 0 Newton) ("N" refers to the unit of force "Newton") needed to be applied to the eye wall in order to slide the sleeve back and expose the needle. The dynamic sleeve may also be configured such that when a pushing force (e.g., advancement) is exerted on the sleeve, this movement may counteract and impede needle exposure, which may allow the device tip to apply increased pressure to the eye wall prior to the initiation of sleeve movement and needle exposure.

Figure 42:
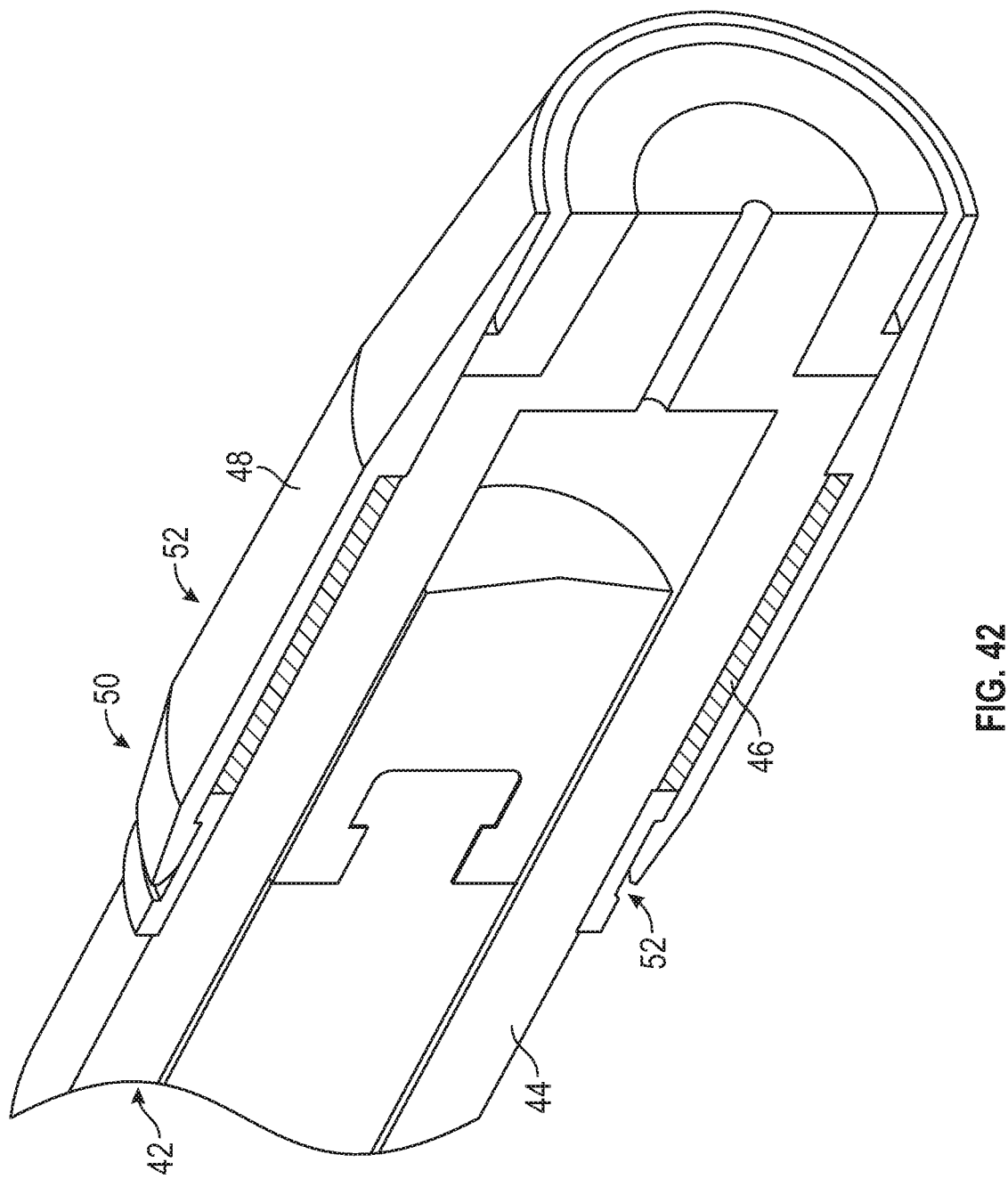
FIG. 42 depicts an enlarged sectional view an exemplary dynamic sleeve.
Figure 46:
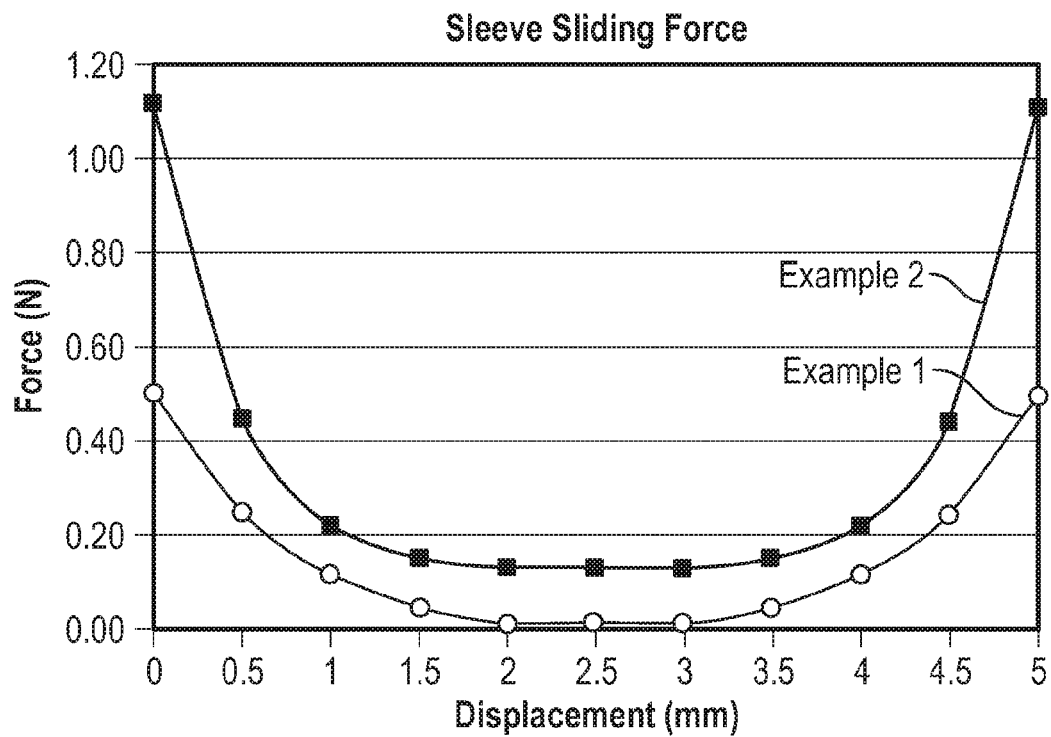
FIG. 46 is a graphic depiction of the amount of resistance force generated by a dynamic sleeve according to one variation.

Some variations of the dynamic sleeve provide a variable force that follows a U-shaped curve, as described further in Example 1 and FIG. 46. Here the biggest resistance is encountered at the beginning and the end of dynamic sleeve movement along the housing with decreased resistance between the start and end points of dynamic sleeve travel. In use, this translates to having an initial high-resistance phase (upon initial placement on the eye wall) followed by a decrease in resistance to sleeve movement during needle advancement into the eye cavity. When the needle is fully deployed, the dynamic sleeve will typically be at the end of its travel path, and increased resistance would again be encountered. This increase in resistive force allows the sleeve to come to a smooth, gradual stop (instead of an abrupt hard stop at the end point) to minimize the risk of transmitting damaging amounts of force to the inert eye wall (which in turn minimizes the risk of causing discomfort or injury to the eye). Here an exemplary dynamic sleeve may be configured to be tapered at the proximal end and distal end. Referring to the sectional view in FIG. 42, integrated injection device (42) includes a housing (44), a resistance band (46) wholly or partially surrounding the housing, and a dynamic sleeve (48) that can be slidably advanced and retracted upon the housing (44). When partially surrounding the housing, the resistance band may be referred to as a resistance strip. The dynamic sleeve (48) has a proximal end (50) and a distal end (not shown) that are tapered. The tapered ends may provide higher traction at the beginning and the end of the dynamic sleeve travel path along the device housing (44) (that is at the beginning and end of needle deployment). The taper at the proximal end (50) provides higher traction and resistance at the beginning of dynamic sleeve movement when it contacts resistance band (46). The thickness of the resistance band (46) may be varied to adjust the amount of resistance desired. For example, the thickness of the resistance band may range from about 0.01 mm to about 5 mm, or range from about 0.1 mm to about 1 mm. Specifically, the thickness of the resistance band may be about 0.05 mm, about 0.1 mm, about 0.2 mm, about 0.3 nun, about 0.4 mm, about 0.5 mm, about 0.6 mm, about 0.7 mm, about 0.75 mm, about 0.8 mm, about 0.9 mm, about 1.0 mm, about 1.5 mm, about 2.0 mm, about 2.5 mm, about 3.0 mm, about 3.5 mm, about 4.0 mm, about 4.5 mm, or about 5.0 mm. The width of the resistance band may also vary and be about 1.0 mm, about 1.5 mm, about 2.0 mm, about 2.5 mm, about 3.0 mm, about 3.5 mm, about 4.0 mm, about 4.5 mm, or about 5.0 mm. Upon reaching the wider middle segment (52), lower-traction and lower resistance movement is encountered, followed by higher traction and higher resistance at the end of needle deployment as the taper at the distal end of the dynamic sleeve is reached. As the dynamic sleeve becomes progressively more tapered at the distal end, more traction is produced against the device housing until it gradually comes to a complete stop. Instead of both ends being tapered, in some variations one of the proximal end and distal end of the dynamic sleeve may be tapered.

Variable traction force may also be provided by components such as circular raised bands or ridges on the outside surface of the device tip. These components may provide counter-traction when approximated against another circular raised band or ridge on the inside surface of the movable dynamic sleeve (inner bands or ridges). When the outer and inner bands or ridges are in contact with each other before the dynamic sleeve begins to move, they generate high traction and high resistance to dynamic sleeve movement. Once the dynamic sleeve starts to move, the raised band on the outside of the device housing moves past the raised band on the inside of the dynamic sleeve, which may result in a rapid decrease in resistance to dynamic sleeve movement and, therefore, decreased pressure on the eye wall by the device tip. The shape of the raised interlocking bands or ridges will generally determine the shape of resistance decrease. For example, the resistance decrease may follow a sine-shaped profile.

The resistance component may also be configured as a slidable shield that is coaxial with housing, and which has a lumen and an internal surface that forms a raised step or platform about at least a portion thereof. In some variations, the step or platform circumscribes the entire lumen of the slidable shield. The luminal diameter of the slidable shield is generally reduced in the area of the step or platform to thus provide higher friction (resistance) when the shield slides along the housing. Thus, the internal diameter of the slidable shield may typically be smaller in its distal portion than in its proximal portion. The width of the raised step or platform may be from about 0.1 mm to about 5 mm, or from about 0.5 mm to about 2 mm. The raised step or platform may also have at least one rounded or sloped edge, e.g., either the proximal or distal edge, or both edges. The raised step or platform may further include an edge that is gradually sloped to achieve a gradually increase the diameter of the lumen and generate a smooth reduction in friction as the slidable shield moves to expose the needle. For example, the edge can be sloped so that the lumen is greater in the proximal portion of the shield than at its distal portion.

In another variation, the dynamic sleeve may generate a force that continuously decreases from its highest point before needle deployment (when the dynamic sleeve completely covers the needle), to its lowest point when the dynamic sleeve begins to move to expose the needle tip. Here the force remains low until the end of dynamic sleeve travel and complete needle deployment. This pattern of resistance decrease may follow a sine-shaped curve.

Slidable advancement of the dynamic sleeve may generate a resistance force against its movement ranging from 0 N to about 2 N. In some instances, slidable advancement of the dynamic sleeve generates a force ranging from about 0.1 N to about 1 N. As previously stated, the amount of force that may be required to move the sleeve may range between about 3 gm and about 30 gm.

Figure 57A:
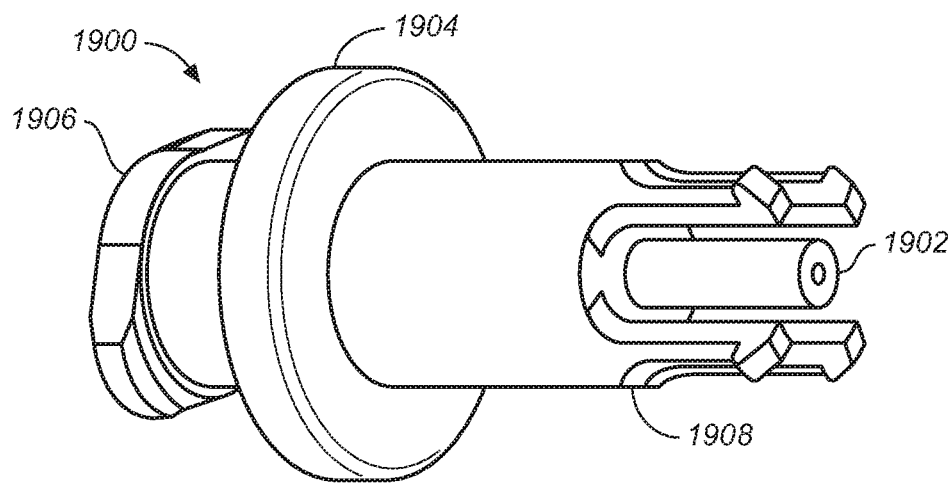
FIGS. 57A and 57B show another variation of an injector attachment having a needle stabilization mechanism or needle guide mechanism.
Figure 57B:
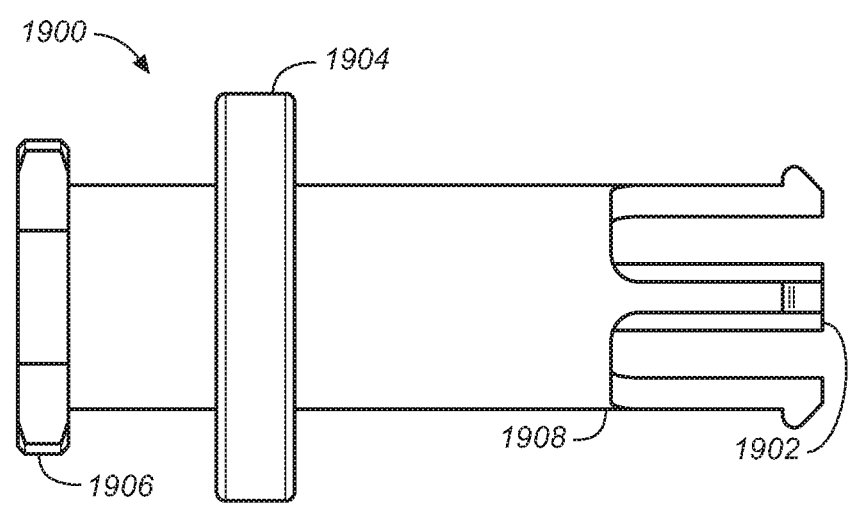

The resistance component may be configured to be part of an injector attachment or injector assembly that can be removably attached to any suitable syringe, including syringes of the luer lock and luer slip type. The resistance component of the injector attachment may interface with the internal surface, external surface, or both surfaces of a slidable sleeve. In some variations, the injector attachment comprises a ring or disc-shaped component that at least partially surrounds the exterior of, and is raised above the surface of the injector attachment. The ring may function as a backstop for the slidable resistance component and/or as a grip or handle to help manipulate the injector attachment on and off the syringe. As shown in FIGS. 57A and 57B, the ring (1904) may entirely surround the injector attachment (1900) and be disposed along the axial length of the injector attachment (1900) about one-tenth to about one-half, or about one-eighth to about one-third, of the distance between the proximal end (1906) of the injector attachment (1900) and the proximal end (1908) of the projections (which are described in more detail below).

In some instances, the resistance component may include a plurality of appendages attached to, or formed as part of, the needle hub. Here the device may be generally configured to include an injector attachment that can be exchanged for the loading needle of a typical syringe. The injector attachment may include a sterile injection needle (e.g., a 30 to 33 gauge needle) and a resistance component (e.g., a dynamic sleeve). An advantage of this modular design may be that side-loading of drug into the device drug reservoir is no longer needed because the device can be loaded like a regular syringe. Such a modular assembly may contain a universal female connector comprising, e.g., a flange, at the proximal portion of the attachment. The female connector may enable the injector attachment to removably interface (i.e., attach and detach) with a male luer-tip drug reservoir. The drug reservoir may be a syringe that includes a luer fitting of the luer lock or luer slip configuration, or any derivative or modification of the luer tip. The modular design may enable loading of a drug reservoir within any of the devices described herein with a drug from a container, e.g., a drug vial. A loading needle can first be used to transfer the drug from the vial to the reservoir. The loading needle may then be detached or switched for an injector attachment.

Figure 53:
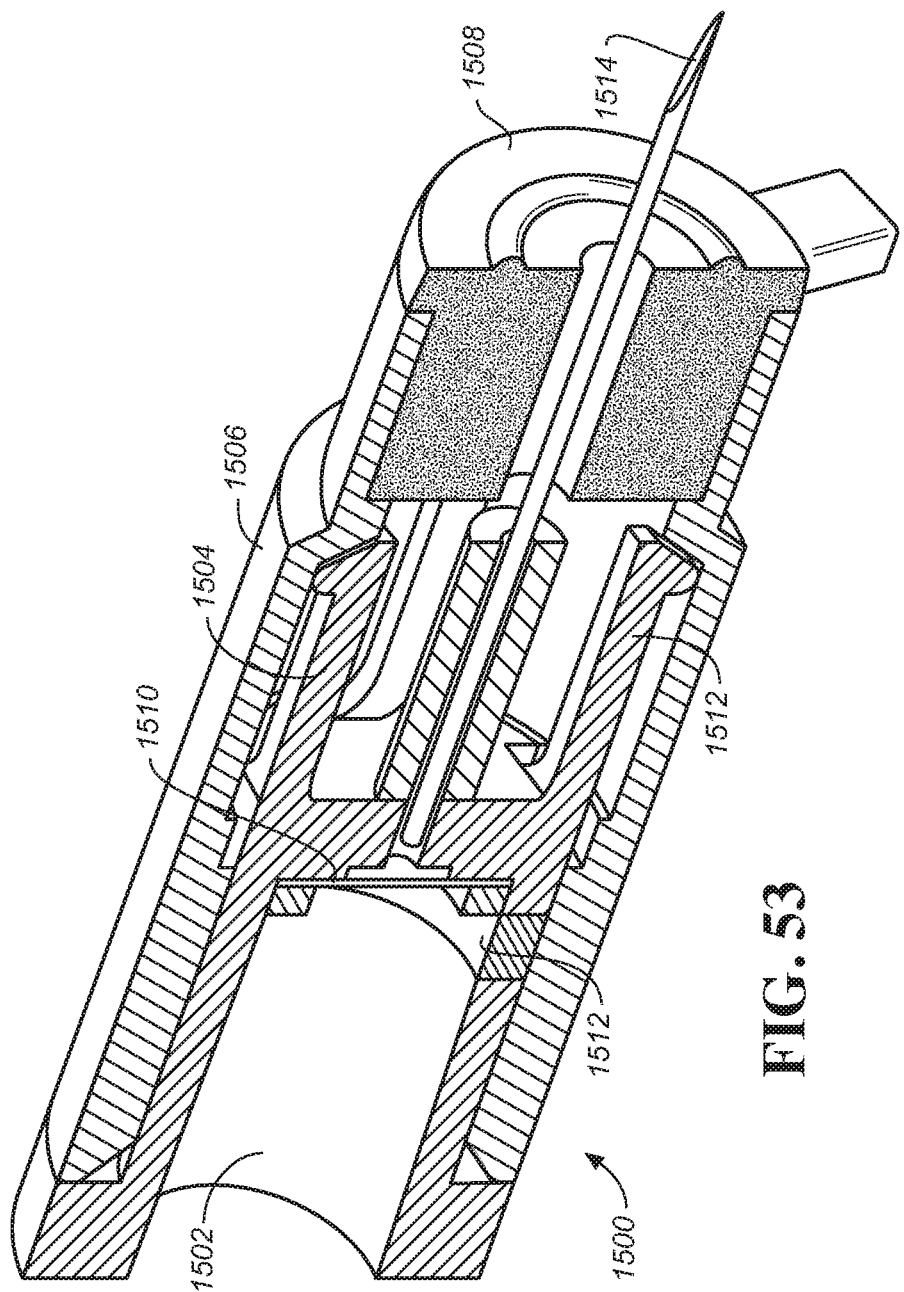
FIG. 53 depicts a partial cross-sectional view of an exemplary injector attachment.
Figure 59:
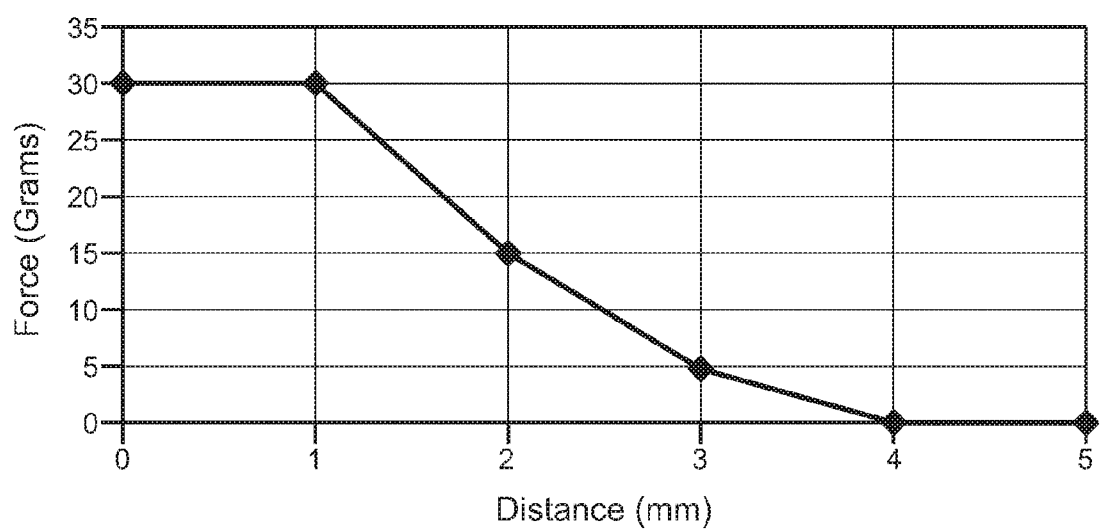
FIG. 59 is a graph that depicts an exemplary resistance profile.

For example, as shown in FIG. 53, an exemplary injector attachment (1500) is shown. Injector attachment (1500) comprises a needle hub (1502) for removably coupling the attachment (1500) to a syringe (not shown). The needle hub (1502) is configured to include a plurality of projections (1504) that extend distally from the needle hub. Although four projections are shown in the figure, any suitable number of projections may be employed on the needle hub. For example, two projections, three projections, four projections, five projections, or six projections may be employed. The projections may be made from any suitable material. In some variations, the projections are formed from a polymeric material, e.g., a plastic material. In one variation, the projections are made from polypropylene. The projections may also be radially spaced about the periphery of the hub in any suitable manner. For example, the projections may be equally or unequally spaced, or symmetrically or asymmetrically spaced, about the periphery of the hub. A slidable shield (1506) may at least surround the needle hub (1502) and projections (1504), and may be operatively coupled to an ocular contact surface having a measuring component (1508). The projections typically provide friction (resistance) with the internal surface of the slidable shield. The desired resistive force that may need to be overcome in order to advance the resistance component (e.g., the slidable shield) may vary between about 0.1 grams and about 100 grams, or between about 5.0 grams to about 30 grams. An exemplary resistance profile is shown in FIG. 59. It is understood that other friction profiles are also contemplated that may require the application of constant force, increasing force, etc., if desired. The amount of friction could be adjusted or optimized, e.g., by increasing the contact surface of the projections, narrowing the internal diameter of the slidable shield lumen, or by varying the materials comprising the contact surfaces (e.g., to vary the coefficient of friction and stiffness). In some variations, there is an interference fit between the slidable shield and the projections. In some instances the interference fit may range from between about 0.05 mm (about 0.002 inches) to about 1.0 mm (about 0.04 inches), or from about 0.08 mm (about 0.003 inches) to about 0.76 mm (about 0.03 inches). For example, an interference fit of about 0.13 mm (about 0.005 inches) between the inner surface (inside diameter) of the slidable shield and the outer diameter of the needle hub assembly may yield a range of force from about 3 grams to about 30 grams of resistive force. In general, a 2% to 5% interference may provide an appropriate amount of resistance. Further, the softer (i.e., less rigid) the projections, the greater the interference. Either or both contact surfaces may also be lubricated, coated, or siliconized to facilitate the smooth sliding movement of the surfaces, if desired. In one variation, a smooth mobility element, e.g., a silicone or thermoplastic elastomeric washer, may be placed inside the shield to generate smooth sliding with the drug conduit or the internal surface of the lumen of the shield, or a coating (e.g., a fluoropolymer coating) or a lubricant applied to at least one friction/traction surface.

However, not all the projections (1504) may be used to provide resistance to shield (1506) movement. Any number of the projections (1504) included may be used to provide resistance. For example, just one or two projections out of four may be used to provide resistance. Projections not used to provide resistance may provide forward and rearward sliding limits for the shield, and may also prevent the shield from rotating relative to the syringe axis. Needle (1514) is attached to the hub (1502) and extends distally therefrom. The force and resistance curves, decreases in resistance, and the amount of force generated between the projections and the slidable shield may be the same or similar to that described for the dynamic sleeve.

One or more longitudinal grooves may also be placed on the internal surface of the slidable sleeve. The grooves may extend through either a partial-thickness or a full-thickness of the sleeve's wall. Thus, the projections from the hub (or needle assembly or housing) travel within the grooves to prevent the sleeve from spinning/rotating around its long axis. In one variation, the grooves preventing the rotation of the sleeve may be useful when the measuring component covers the 360 degrees of circumference of the tip (i.e., when there is no need to rotate the sleeve to orient the measuring component towards the limbus).

The injector attachments may be made by bonding the needle to a needle hub configured with a plurality of projections. A shield such as the one shown in FIGS. 54B and 54C may be slid over the needle hub until it snaps in place. No adhesives are used to secure the shield to the needle hub. A safety clip (as further described below) may be attached to the needle hub to prevent back and forward movement of the shield on the needle hub. The needle hub may be made from any suitable material. In some variations, the needle hub is made from polypropylene. In other variations, the needle hub is made from polycarbonate. The slidable shield may also be made from any suitable material. For example, the slidable shield may be made from a polycarbonate, including polished polycarbonate.

Some variations of the safety clip generate resistance that impedes the movement of the shield relative to the drug conduit. For example, the clip could lock the shield in a certain position or more than one position (such as pre-deployment resting position, post-injection end position, or both), and may prevent the movement of the shield relative to the drug conduit. In one variation, the safety clip does not rotate relative to the long axis of the device. In another example, the safety clip may be rotatable relative to the long axis of the device.

Figure 54A:
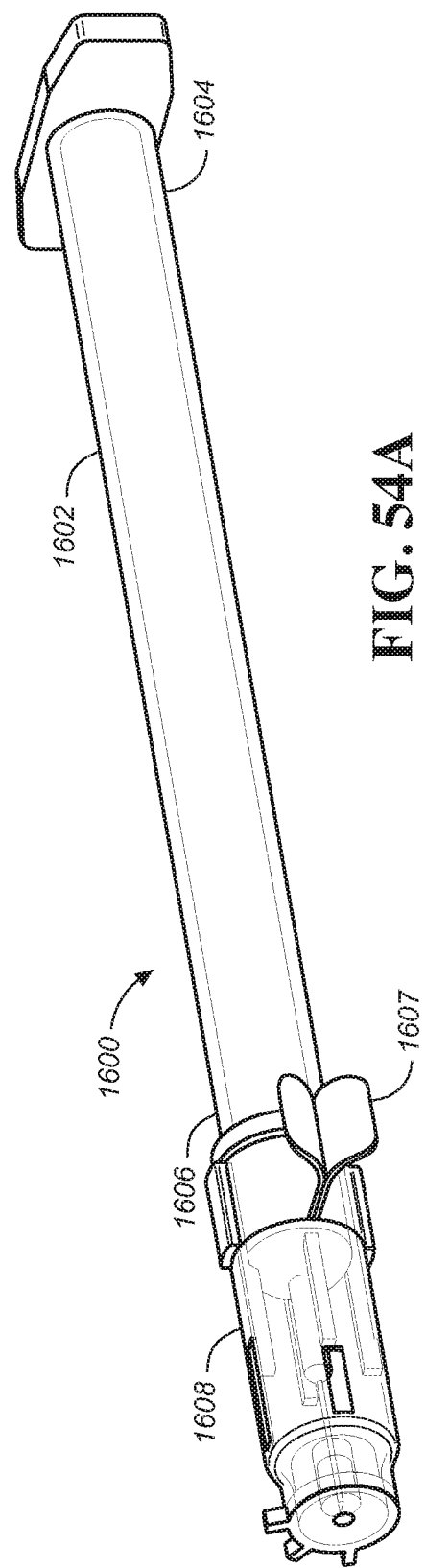

Another variation of the injector attachment is shown in FIGS. 54A-54C. In these figures, the injection device (1600) is depicted as comprising a syringe body (1602) having a proximal end (1604) and a distal end (1606). An injector attachment (1608) is removably coupled to the distal end (1606). In this variation, and as illustrated in more detail in FIGS. 54B and 54C, injector attachment (1608) includes a needle hub (1610) having a proximal end (1611), a needle (1612), and four projections (1614) extending distally. As previously stated, any suitable number of projections may be used. The projections (1614) may be configured, shaped, etc. at their distal ends with a tab (1616). Instead of tabs, the distal ends may also be configured as hooks, flaps, etc. Injector attachment (1608) also includes a slidable shield (1618) having a proximal end (1620) and a distal end (1622), and slots (1624) provided through the wall, or partially through the wall, of the shield (1618). The slots may have any suitable size, shape, and geometry, and will typically be configured to interface with the slots in a complimentary manner. The projections (1614) generally have a slight interference fit with the inside surface of the slidable shield (1618). An ocular contact surface having a measuring component (1626) may be coupled to the distal end (1622) of the shield (1618). In use, the projections (1614) slide along the inside surface of the slidable shield (16 18), and because of the interference fit with the inside surface, provide resistance to shield (1618) movement. Resistance is provided until the projections (1614) reach the slots (1624) in the shield (1618). Upon reaching the slots (1624), the tabs (1616) at the distal ends of the projections (1614) expand (e.g., radially expand) into the slots (1624), thereby decreasing the resistance to movement of the shield (1618). The amount of resistance can be adjusted by adjusting such factors as the thickness of the tabs or the degree of interference of the projections with the inside surface of the shield. A clip (1607) may be provided on the needle hub (1610) for preventing axial movement of the shield (1618) along the outer surface of the needle hub (1610). Axial movement of the shield (1618) can occur when the clip (1607) is removed. The clip may be a safety feature that prevents the resistance component, e.g., the slidable shield from longitudinally moving along the axis of the device. The clip may be of any suitable configuration that prevents axial movement of the shield when coupled to the needle hub, and which allows axial movement when removed from the needle bub. In some variations, the clip may be locked to the device housing or the needle hub assembly so that it does not rotate about the housing (e.g., about the longitudinal axis of the device). However, in other variations, the clip may be configured to be rotatable about the housing. In some variations, as further described below, a locking mechanism, such as a clip, that controls the mobility of the dynamic shield or sleeve is non-removably attached to the devices housing, the shield, needle hub/assembly, drug reservoir, or any part of the device. For example, the locking mechanism may be released by pressing its rear lever, thus releasing the slidable shield and rendering it mobile.

Although the clip is shown as comprising a looped body portion and tabs in the figures, it may be of any suitable configuration. For example, the body portion may have a width between about 1 mm and about 12 mm, between about 3 mm and about 10 mm, or between about 4 mm and about 8 mm. The clip may be made from any suitable material. Exemplary materials include without limitation, polyethylene, polycarbonate, polypropylene, acrylonitrile butadiene styrene polymers, Delrin® acetal homopolymers, polyurethane, acrylic polymers, polyether ether ketone, and combinations thereof. In one variation, the clip is made from polyethylene.

Figure 63A:
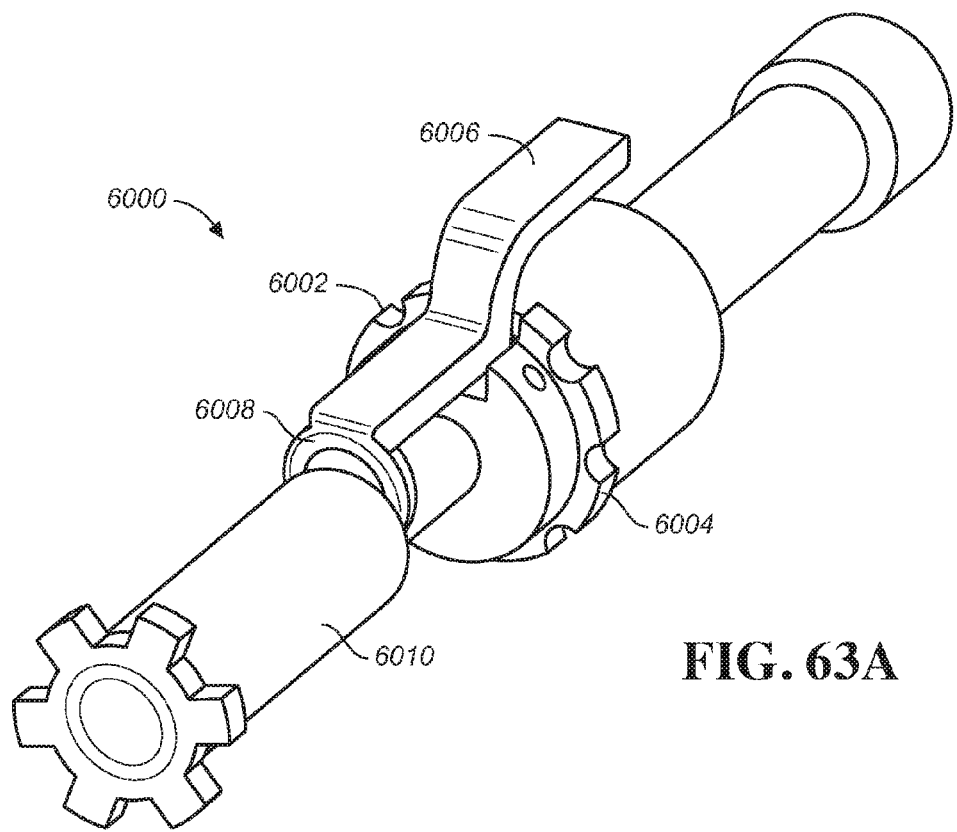
FIGS. 63A-63B depict another variation of the device clip and how it functions to prevent and allow movement of a slidable sleeve.
Figure 63B:
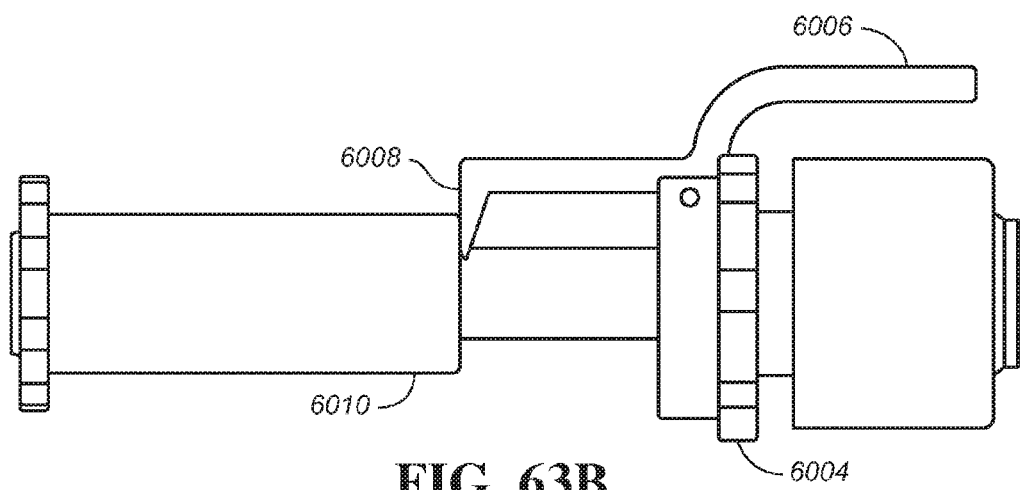

Clips that are fixed or non-removably attached to a portion of the injector device or injector attachment could also be employed. These clips could be of any suitable configuration that prevents movement of the resistance component. Some variations of the clip may be fixed to the device housing, while others are fixed to a portion of the needle assembly. For example, as shown in FIG. 63A, the clip may be a lever (6002) that is attached to the needle assembly (6004) of the device (6000). The lever (6002) comprises two ends, where one end includes a release tab (6006) and the other end, a locking shoulder (6008). In its locked position (FIG. 63B), the locking shoulder (6008) contacts a portion of the resistance mechanism, here shown as slidable sleeve (6010) to prevent movement of the slidable sleeve (6010). When the release tab (6006) is depressed, e.g., in the direction of arrow A, as shown in FIGS. 63C-63D, the pressure on the release tab (6006) pivots the lever (6002) at its point of fixation to the needle assembly (6004) so that the end with the locking shoulder (6008) is lifted, e.g., in the direction of arrow B. By lifting the locking shoulder (6008), contact between the locking shoulder (6008) and slidable sleeve (6010) is removed, and the slidable sleeve (6010) is unlocked and free to move (i.e., slide) proximally. After injection has been completed, the slidable sleeve (6010) can again be locked against movement by pressing the locking shoulder (6008) so that it contacts the slidable sleeve (6010).

The clip may comprise a resistance component, a safety feature, or a combination thereof, that prevents the resistance component, e.g., the slidable component such as a shield or sleeve from longitudinally moving along the axis of the device. For example, the clip may prevent the slidable component from moving relative to the drug conduit in the pre-deployment or resting state. In some variations, the clip may prevent the slidable component from moving relative to the drug conduit in both pre-deployment and post-injection states when the tip of the drug conduit, for example an injection needle, is completely covered by the slidable component such as a shield or a sleeve. In some variations, the clip may create resistance to and partially or completely hamper the back and forth mobility of the slidable component relative to the drug conduit in at least one or both pre-deployment and post-injection states when the tip of the drug conduit is completely covered.

The eye is a unique organ in that it is shaped as a hollow sphere that bas certain intraocular pressure (IOP) normally maintained within a certain range that increases when external pressure is applied onto the eye wall and may cause tissue damage or intraocular material and/or venous occlusions. In addition, the eye is exquisitely sensitive to external pressure that may cause substantial discomfort for the individual in the form of photopsia, uncomfortable pressure sensation and/or pain, which may be difficult to completely abolish even by topical anesthesia. Thus, there is a need for a mobility control mechanism that controls the mobility of a slidable component that protects the tip of a drug conduit, such as the injection needle, while the device is placed onto the eye wall, while controlling the level of pressure applied onto the eye wall. Such a mechanism enables stable and safe placement of the intraocular drug delivery device onto the eye surface while the slidable component is locked and non-mobile in the needle pre-deployment state, but without applying excessive pressure onto the eye wall. The mechanism may be gradually or completely released to partially or completely remove the lock on the slidable component rendering it partially or freely mobile in the needle deployment state during intraocular injection. Thus, the mobility control mechanism enables manual control of the slidable element's mobility ranging from it being completely locked and immobile to being partially mobile with certain resistance, to being completely and freely mobile relative to the drug conduit. For example, the slidable component may be non-mobile in the pre-deployment and post-injection states but freely or partially mobile during the injection state by completely or partially releasing the mobility control mechanism, for example by manually pressing on the rear lever of the control mechanism thus lifting its front locking part. The mobility control mechanism ensures that the drug conduit, such as an injection needle, is not deployed or exposed prematurely before the device is properly positioned in the desired location of the eye surface. In other variations, it may also ensure that the slidable shield or sleeve securely covers the tip of the drug conduit at the end of the injection procedure preventing accidental needle sticks.

In some instances, the proximal end of the slidable shield comprises a centration/stabilization element, such as a band or ting having a certain thickness and its internal lumen diameter smaller than the remainder of the proximal portion of the slidable shield. The centration/stabilization enables a snug interface between the slidable shield and the needle hub assembly or device housing, thus stabilizing and centering the slidable shield relative to the long axis of the device during its travel. In one example, the centration/stabilization element is attached to the internal surface of the proximal end of the slidable shield. The slidable shield may have slots provided through the wall, or partially through the wall, of the shield. The slots may have any suitable size, shape, and geometry, and will typically be configured to interface with the slots in a complimentary manner.

Figure 61A:
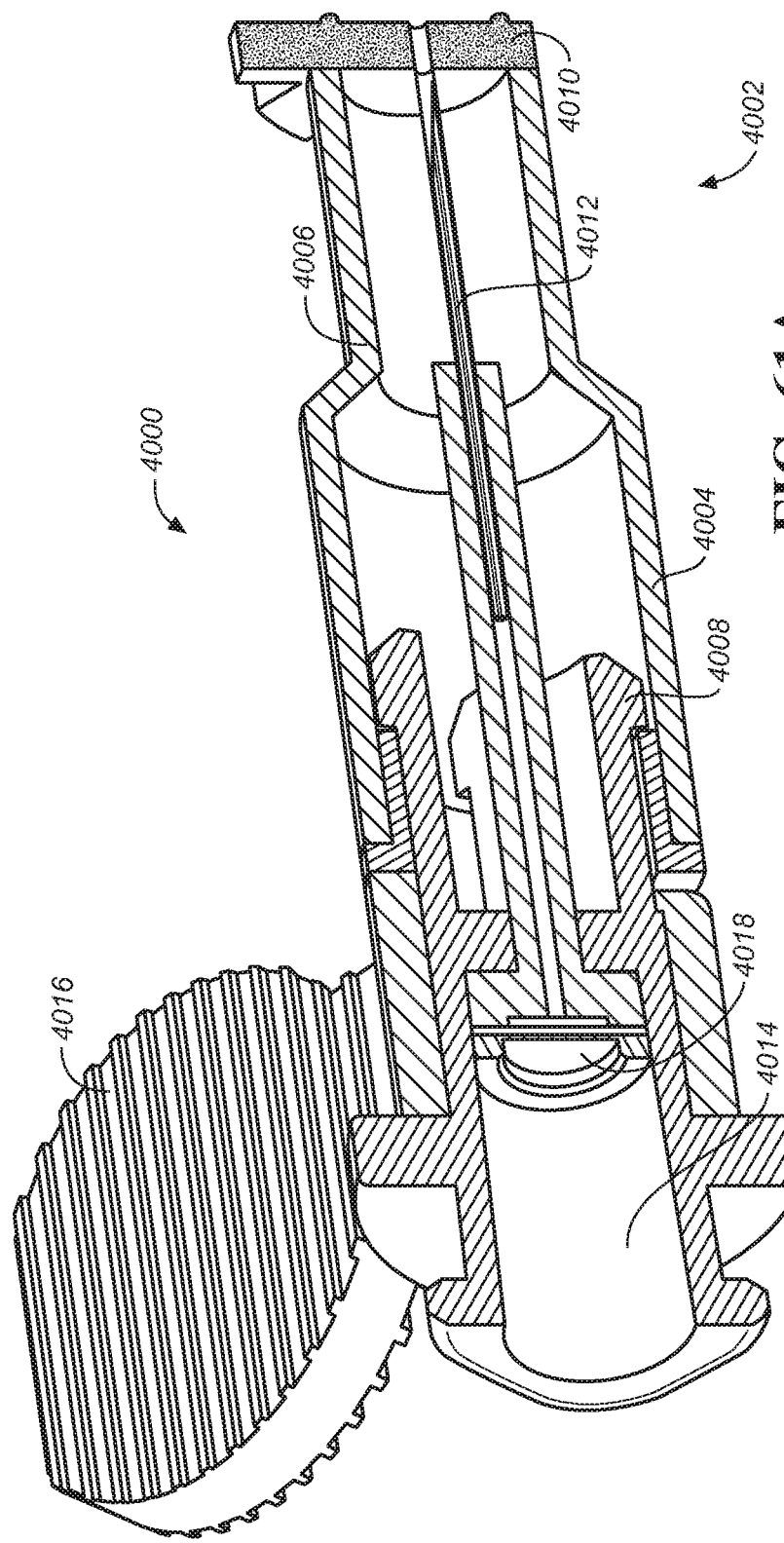
FIGS. 61A-61B show partial cross-sectional views of another exemplary injector attachment.
Figure 61B:
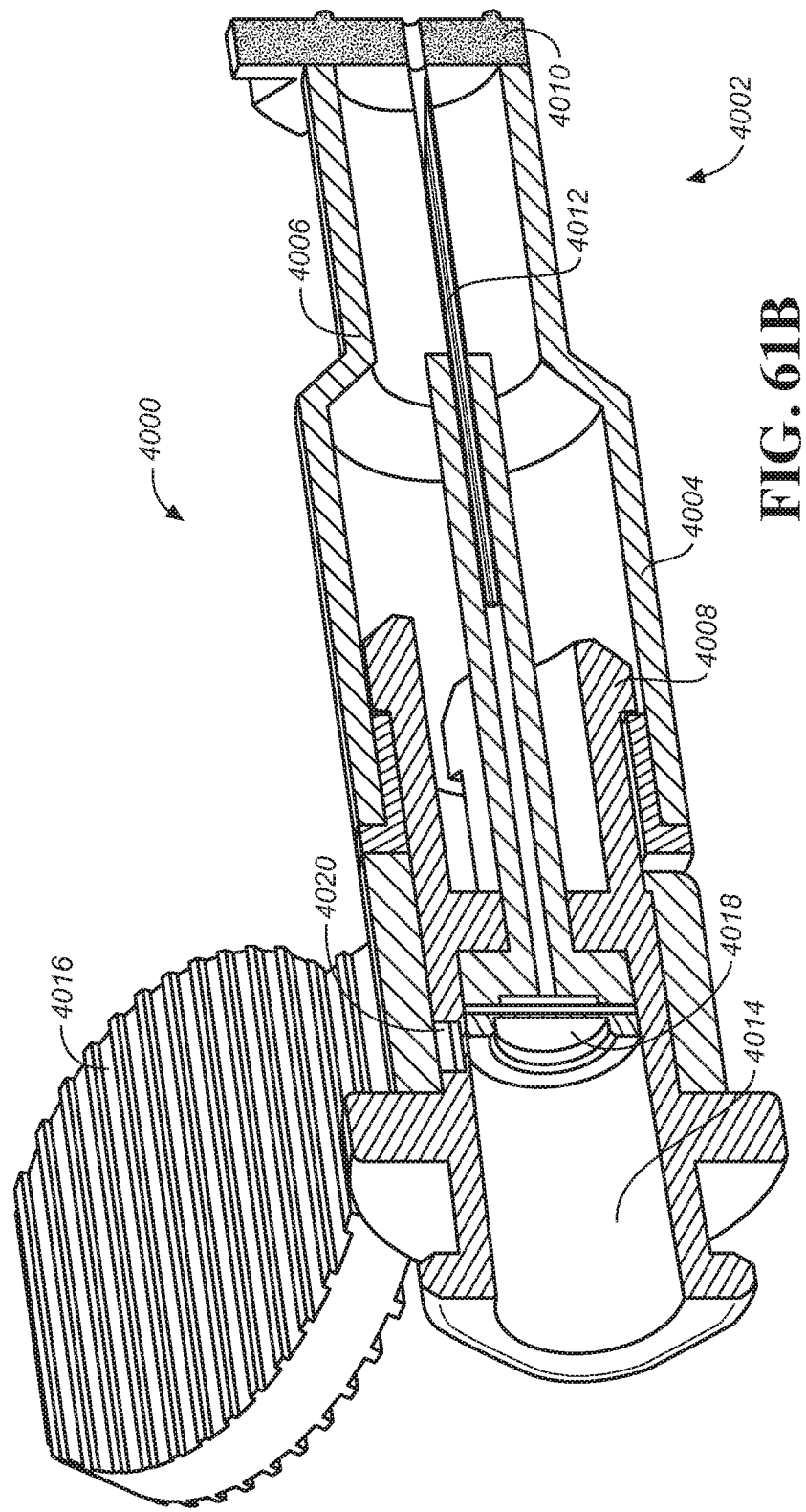

In yet a further variation, as shown in FIG. 61, the resistance component of the injector attachment (4000) may be configured as a slidable shield (4002) that has a wider proximal portion (4004) and a narrower distal portion (4006). Here the internal diameter of the lumen of the wider portion of the slidable shield is generally larger than the internal diameter of the narrower portion. This configuration may allow the wider portion (4004) to be the portion where friction/traction elements of the shield (4002) and needle hub assembly interface (4008) (or of the shield and housing in other variations), and the narrower portion to be the portion that enables the attachment of a measuring component (4010) onto the device tip. In some instances, the internal diameter of the narrower portion of the slidable shield may be substantially similar to the external diameter of a needle holder (4012) (e.g., see FIG. 61). The needle holder that may be attached to the needle hub assembly may fit snugly into the lumen of the narrow portion of the shield at least along some part of the travel path of the shield, which may enable stabilization and centration of the drug conduit attached to the needle holder. In these variations, the clearing between the external surface of the needle holder and the internal surface of the lumen of the narrow portion of the shield may be between about 0.01 mm and about 1 mm.

Alternatively, resistance or friction force may be generated by the friction between the drug conduit and the needle tunnel, device tip, or ocular contact surface. For example, the resistance or friction force may be generated between the shaft of the drug conduit and the material comprising the device tip and/or ocular contact surface.

As further shown in FIG. 61A, the removable injector attachment may include a clip (4016) that is capable of being removed from the needle assembly (4014), and a filter (4018), which here is a hydrophilic filter. In other variations, the removable injector attachment includes both a hydrophilic filter (4018) and an air removal mechanism (4020), which here is a hydrophobic filter.

As previously stated, the benefit of the injector attachment is that it can be used with commercially available syringes, e.g., tuberculin or insulin syringes. Drug may first be loaded into the syringe in the usual manner using a standard loading needle instead of through a side port. The standard needle may then be removed and an injector attachment, as described herein, placed on the luer slip at the distal end of the syringe. The clip may then be removed to free the shield and allow it to axially move along the surface of the needle hub. The ocular contact surface (e.g., with measuring component) may then be placed on the surface of the eye. Next, the syringe body may be advanced to advance the needle into the eye. During this syringe advancement step, the projections on the needle hub generally slide within the shield distally (toward the ocular contact surface). The shield may also slide proximally (toward the proximal end of the needle hub) due to the initial wall tension of the ocular surface. The resistance to sliding of both the needle hub and shield may be adjusted or manipulated based on the particular structure or configuration of the projections extending from the shield. The needle is prevented from being advanced any further once the tabs on the distal ends of the projections snap into the slots in the wall of the shield. The needle may be advanced from between about 1 mm to about 25 mm, or from between about 2 mm to about 8 mm, into the eye before the slots am reached. Drug may then be injected into the eye using the plunger of the syringe and then the syringe and needle removed from the eye.

In variations where the resistance component comprises a slidable shield/sleeve, the resistance component may function to protect the sterility of the drug conduit, e.g., a needle. The slidable shield may protect needle sterility by protecting it from accidental contact with and contamination from, the eyelids, eyelashes, ocular surface secretions, and/or airborne pathogens. The slidable shield/sleeve may also function to protect the needle from contamination by the eyelids and lashes when the patient blinks. Further, the slidable shield/ sleeve may function to prevent or minimize the circulation of non-sterile secretions and tears over the injection site.

Measuring Components

The devices described here may include a measuring component that may be useful in determining the location of the intraocular injection site on the eye surface. Some variations of the device may include an ocular contact surface having a high-traction surface integrated with a measuring component. The measuring component may be fixedly attached or removably attached to the ocular contact surface. The measuring component may also be configured to fully (360 degrees) or partially rotate (less then 360 degrees) about the long axis of the device housing. Inclusion of a rotatable (dynamic) measuring component may allow the operator to maintain a comfortable grasp of the device without having to change or reposition the finger placement pattern in order to appropriately client the measuring component toward the limbus in any meridian either in the left or right eye of a mammal (for example perpendicular to the limbus), in order to accurately determine the injection site and before stably positioning the device tip on the eye surface. A rotating (dynamic) measuring component may also enable sterile localization of injection site in any meridian/clock hour relative to limbus circumference, while avoiding contact with the eyelids or eyelashes.

In some variations, the measuring component comprises one or a plurality of measuring elements or tabs radially extending from the proximal device tip comprising an ocular contact surface. The radial measuring elements or tabs may be oriented perpendicular to the circumference of the proximal device tip comprising an ocular contact surface. In one variation, the measuring component comprises, 1-12, or 3-9, or 6-8, or 6 radially oriented measuring elements or tabs.

In one variation, the measuring component spans the entire circumference of the proximal device tip comprising an ocular interface surface. In another variation, the measuring component spans a portion of the circumference of the proximal device tip comprising an ocular interface surface.

In one variation, the angle between any two adjacent radial elements is the same and constant. In some examples, the angle between any two adjacent radial elements is between 180 degrees and 15 degrees, or between 35 degrees and 25 degrees, or about 30 degrees.

In another variation, all radially oriented elements have equal lengths. In another example, at least some of the radially oriented elements have different lengths. In one example, the lengths of the radially oriented elements vary between 1 mm-6 mm, or between 3.5 mm-4 mm.

Figure 8:
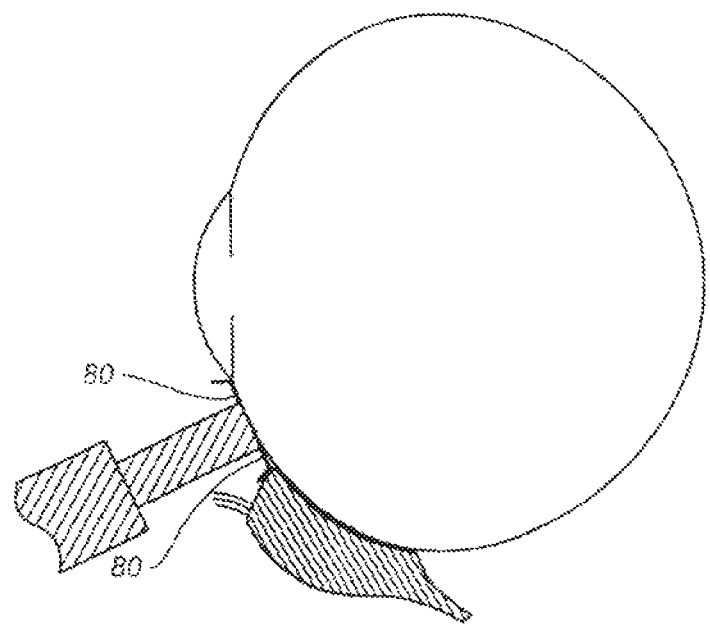
FIG. 8 illustrates how an exemplary measuring component works to retract the eyelid and measure a certain distance from the limbus.

As previously stated, the measuring component may be raised above the ocular surface so that it prevents the eyelid from coming in contact with the sterile ocular contact surface of the device tip (e.g., FIGS. 2A-2B and 8). The specific configuration of the measuring component may also help to minimize the risk of inadvertent contamination of the sterile drug dispensing member (conduit) such as an injection needle. Such contamination may result from various causes such as the sterile needle coming in inadvertent contact with an eyelid or other non-sterile surface. The measuring components may also be colored in a manner to provide color contrast against the surface of the eye including the conjunctiva, the sclera, and the iris. The distance from the deployed needle tip to the tip of each individual measuring component may be about 4 mm. Here the distance from the needle tip to the outer edge of corneo-scleral limbus may be about 3.5 mm. In some instances, e.g., when the measuring component comprises two tabs, and the tabs are rotated so that the tips of the tabs are simultaneously touching the outer edge of corneo-scleral limbus, the injection site is located at 3.5 mm from limbus (ranging from 1 to 4 mm).

In general, the measuring component will enable the intraocular injection site to be more precisely placed at a specific distance from, and posterior or anterior to, the corneal-scleral junction termed "the limbus." In some variations, the measuring component may provide for placement of the intraocular injection site from about 1 mm to about 5 mm, from about 2 mm to about 4.5 mm, or from about 3 mm to about 4 mm, from and posterior to the limbus. In another variation, the measuring component may provide for placement of the intraocular injection site from about 2 mm to about 5 mm posterior to the limbus, or about 3.5 mm posterior to the limbus. In other variations, the measuring component may provide for placement of the intraocular injection site from within about 3 mm or about 2 mm, from and anterior to, the limbus, or between about 0.1 mm and about 2 mm from and anterior to the limbus. In one variation, the measuring component provides for placement of the intraocular injection site between about 1 mm anterior to the limbus and about 6 mm posterior to the limbus. In another variation, the measuring component provides for placement of the intraocular injection site between about 3 mm to about 4 mm posterior to the limbus.

The measuring components may have any suitable configuration. For example, the measuring components may be located on one side of the ocular contact surface or on more than one side of the ocular contact surface (e.g., FIGS. 9, 10, and 11). Here, when the tip of the measuring component is placed right next to the corneo-scleral limbus, the site of the intraocular needle injection is placed at a particular distance from the limbus, e.g., between about 3 mm and about 4 mm posterior to the limbus.

In alternative variations, the measuring component comprises one or more members (e.g., FIGS. 9, 10, and 11). These members may radially extend from the ocular contact surface. Having more than one member comprise the measuring component may be beneficial in ensuring that the distance between the limbus and injection site is measured perpendicular to the limbus and not tangentially as it may be the case when the measuring means comprise a single member. When the tips of one or more than one radial member comprising the measuring component are aligned along the corneo-scleral limbus, the site of the intraocular needle injection is placed at a particular distance from the limbus, such as between about 3 mm and about 4 mm posterior to the limbus.

More specifically, as shown in FIG. 8, the device tip having an ocular contact surface comprises a measuring component (80) that enables the determination of the injection site at a certain distance relative to the corneo-scleral limbus. As previously stated, in one variation the measuring component is located on one side of the device tip. In another variation, more than one measuring component is located on more than one side of the device tip. In yet further variations, the tip of the measuring component may be raised, bent, etc., which prevents the eye lid from sliding over the measuring component and coming in accidental contact with the dispensing member (conduit) of device. Also in FIG. 8, the dispensing member (conduit) is shown as being completely shielded inside the device tip.

Figure 9A:
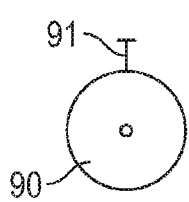
FIGS. 9A-9C show exemplary arrangements of measuring components around an ocular contact surface.
Figure 9B:
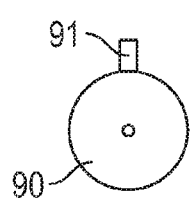
Figure 9C:
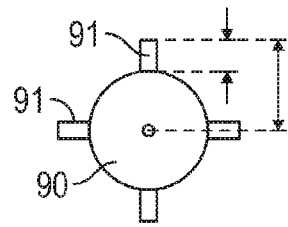

FIG. 9 provides further detail about another variation of the measuring component. Here the device tip comprises a ring-shaped ocular contact surface (90) and a measuring component (91) that enables the determination of the injection site at a certain distance relative to the corneo-scleral limbus. The outer circumference of the device tip that comes into contact with the surface of the eye has, e.g., a ring shaped ocular interface, and the dispensing member such as an injection needle may be hidden inside and protected by the device tip. In FIG. 9, the measuring components (91) are located on one side of the device tip (FIGS. 9A-9B) or on more than one side of the device tip (FIG. 9C). Thus, when the tip of the measuring component is placed next to the corneo-scleral limbus, the site of intraocular needle injection is placed at a specific distance from the limbus, such as between about 3 mm and about 4 mm posterior to the limbus. Any suitable number of measuring components may be provided on the device tip, e.g., attached to the ocular contact surface. When a plurality of measuring components are used, they may be arranged around the ocular contact surface in any suitable fashion. For example, they may be circumferentially disposed around the ocular contact surface or on one side of the ocular contact surface. They may be equally or unequally spaced around the circumference of the ocular surface. In other variations, the measuring components may be symmetrically spaced or asymmetrically spaced around the circumference of the ocular contact surface. These configurations may be beneficial in allowing the injector to rotate the device along its long axis.

Figure 10A:
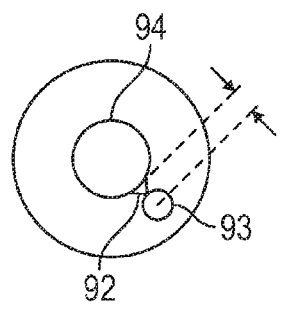
FIGS. 10A-10C depict other exemplary measuring components and how they work to measure a certain distance from the limbus.
Figure 10B:
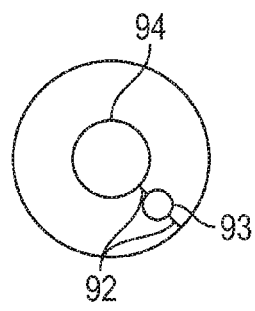
Figure 10C:
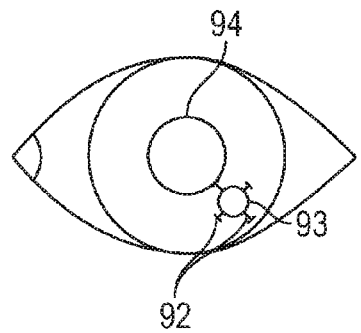
Figure 11A:
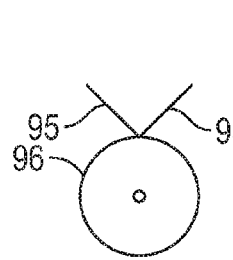
FIGS. 11A-11D show further exemplary measuring components.
Figure 11B:
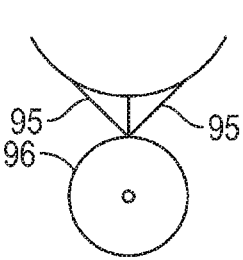
Figure 11C:
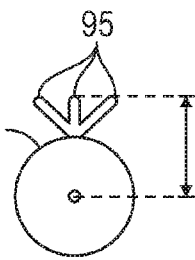
Figure 11D:
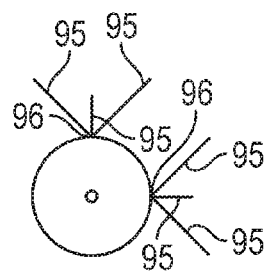

FIGS. 10A-10C provide additional views of measuring components that are similar to those shown in FIGS. 9A-9C. In FIG. 10, a ring-shaped ocular contact surface (93) is shown having a measuring component (93) that enables the determination of the injection site at a certain distance relative to and perpendicular to the corneo-scleral limbus (94). The measuring components are depicted on one side of the device tip, or in another variation, on more than one side of the device tip. Again, the measuring components may comprise one or more members. Having more than one member comprise the measuring component may be beneficial in ensuring that the distance between the limbus and injection site is measured perpendicular to the limbus and not tangentially as it may be the case when the measuring component comprise a single member. When the tips of all members comprising the measuring component are aligned along the corneo-scleral limbus, the site of the intraocular needle injection is placed at a particular distance from the limbus, such as between about 3 mm and about 4 mm posterior to the limbus.

More than one measuring component is also shown in FIGS. 11A-11D. Here the measuring components (95) are depicted as extending from a common attachment point (96) on the ocular contact surface. When the tips of all members comprising the said measuring component are aligned along the corneo-scleral limbus, the site of the intraocular needle injection is placed at a particular distance from the limbus, such as between about 3 mm and about 4 mm posterior to the limbus.

Figure 44A:
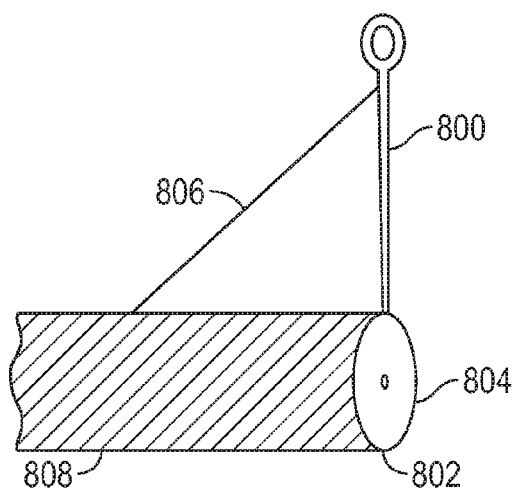
FIGS. 44A-44D depict exemplary positional indicator components.
Figure 44B:
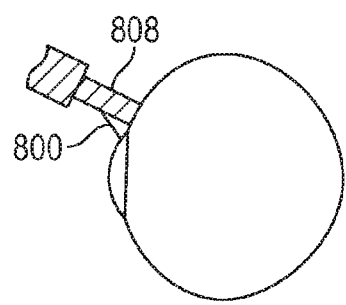
Figure 44C:
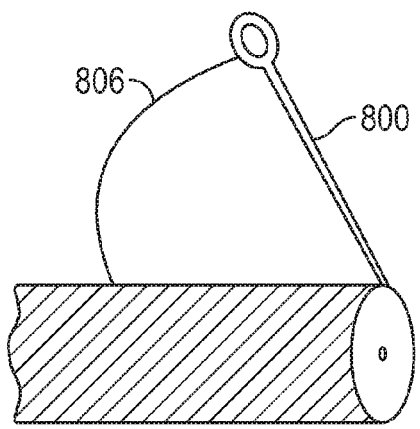
Figure 44D:
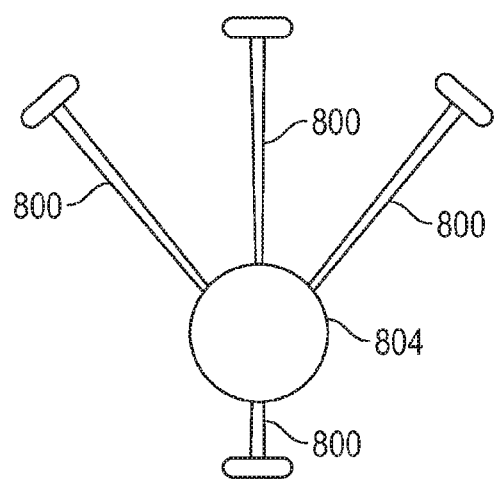

Alternatively, the measuring components may be configured as one or more flexible measuring strips. Flexible materials that may be used to make the measuring strips include flexible polymers such as silicones. As shown in FIG. 44A, the measuring strip (800) may extend from the device tip (802), usually from the side of the ocular contact surface (804), so that the distance between the limbus and injection site can be measured perpendicular to the limbus. A positional indicator component (806) may be employed to ensure that the measuring strip (800) is properly used. For example, as shown in FIG. 44B, correct positioning of the measuring strip (800) (so that a 90 degree angle is formed between the measuring strip and device housing (808)) may be determined when the positional indicator component is substantially taut. In contrast, a slack positional indicator component (as shown in FIG. 44C) would indicate incorrect positioning. The positional indicator component may be a cord. In one variation, the integrated device comprises at least three measuring strips. In another variation, the integrated device includes at least four measuring strips. When a plurality of measuring strips are used, they may be configured in any suitable manner around the tip of the integrated device (equally spaced around the circumference of the ocular contact surface, symmetric or asymmetrically placed around the circumference of the ocular contact surface, etc.). For example, as shown in FIG. 44D, the measuring strips may be configured to span the desired 90 degree angle (45 degrees plus 45 degrees between the farthest strips) to allow for a 90 degree rotation of a control lever without having to reposition the hand of the user.

Figure 12:
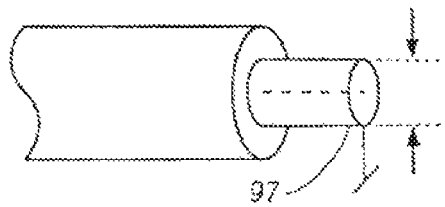
FIG. 12 shows an exemplary device that includes a marking tip member.
Figure 13:
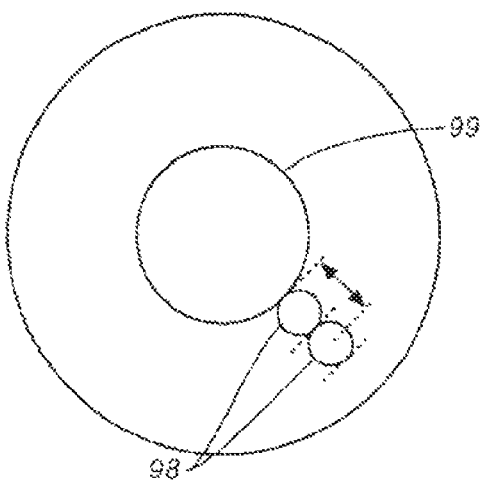
FIG. 13 illustrates how marks made on the surface of the eye by an exemplary marking tip member can be used to position the device at a target injection site.

In some variations, the measuring component may be configured as a marking tip member (97). As shown in FIG. 12, the marking tip member (97) at its distal end (closer to the eye) that interfaces with the ocular surface and leaves a visible mark (98) on the conjunctival surface when pressed against it (e.g., FIG. 13). The marker-tip enables intraocular injections to be carried out through a safe area of the eye relative to the corneo-scleral limbus (99), such as between about 3 mm and about 4 mm posterior to the limbus, over the pars plana region of the ciliary body of the eye. The diameter of the marking tip may range from about 1 mm to about 8 mm, or from about 2 mm to about 5 mm, or from about 2.3 mm to about 2.4 mm (e.g., FIG. 12).

In further variations, the measuring component may be a sectoral measuring component. The sectoral measuring component may be configured to span a sector of between about 1 degree and about 180 degrees of arc (e.g., between about 45 degrees and 90 degrees of arc) at the distal end of device or housing. In general, by "sectoral" it is meant that only a portion or section of the measuring component includes elements for taking measurements. For example, a sectoral measuring component may include radially extending members that are spaced from about 1 degree to about 90 degrees about the circumference of the device tip. During precise localization of the injection site, a sectoral measuring component configured in this manner may enhance sterility of the procedure because the measuring component can be oriented toward the limbus and away from periocular appendages such as the eyelids and eyelashes. Here the sectoral measuring component may avoid contact with the appendages, thus minimizing the risk of bacterial contamination and intraocular infection, while enabling precise localization of the injection site relative to the limbus in a sterile manner.

Figure 47:
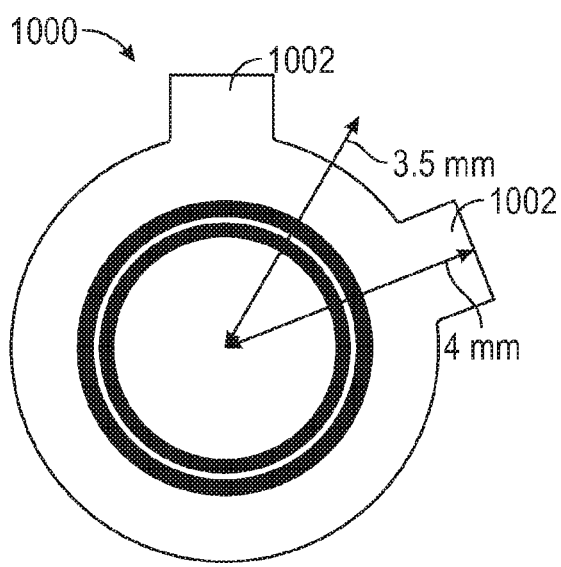
FIG. 47 depicts an end view of an exemplary sectoral measuring component.

In one variation, the sectoral measuring component may comprise a central (core) member having a proximal end and a distal end, and comprising a plurality of radially oriented spokes or tabs as the radially extending members, which are equal in length. Central member may be round, oval, square, rectangular or triangular in shape having a circumference or a perimeter. When central member is round, its diameter may be between about 1.0 mm and about 8.0 mm, or between about 3.0 mm and about 6.0 mm. Radially extending members may have the same fixed angle between any two adjacent members, for example, between 1 degree and 90 degrees, or between 15 degrees and 45 degrees. The radially extending members may also have the same length, so that the distance between the needle exit point and the tip of each individual radial member tip is substantially the same, for example between about 1.0 mm and about 5.0 mm, or between about 3.0 mm and about 4.0 mm. With this configuration, the sectoral measuring component may provide fine adjustment of device positioning on the ocular surface around the limbus circumference while rotating the entire device between 1 and 180 degrees (or between 1 and 90 degrees) and using any one or plurality of spokes or tabs to measure the distance between injection site and the limbus. As shown in FIG. 47, using any single tab or spoke (1002), or any two adjacent tabs or spokes (1002) of a sectoral measuring component (1000) that simultaneously touch the limbus line enables the measurement of two fixed distances relative to the limbus, for example 4 mm and 3.5 mm, respectively. More specifically, when the measuring component is rotated so that the tip of only one tab or spoke touches the limbus line while the tab or spoke is perpendicular to the limbus line, the injection site is localized at about 4 mm (ranging from about 3 mm to about 5 mm) from the limbus. When the measuring component is rotated so that the tips of two tabs or spokes are simultaneously touching the limbus line, the injection site is at about 3.5 mm from limbus (ranging from about 1 mm to about 4 mm).

Figure 60:
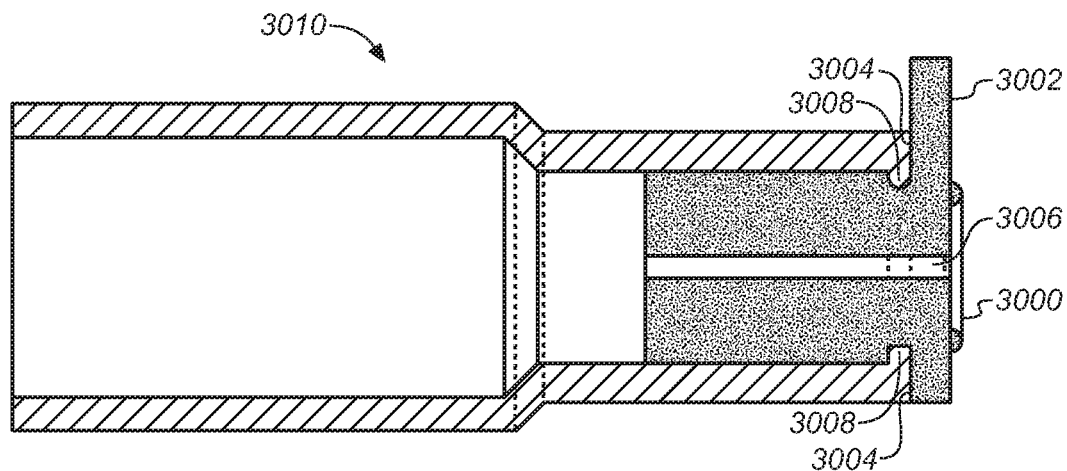
FIG. 60 depicts a side, cross-sectional view of an exemplary device tip coupled to a slidable shield by an interference fit.

In another variation, three divergent measuring tabs or spokes may comprise the measuring component. In a further variation, two divergent measuring tabs or spokes may comprise the measuring component. The divergent measuring tabs or spokes may span a curvilinear distance between about 30 degrees and about 180 degrees or between about 45 degrees and about 90 degrees on the distal surface of the device tip. Having the measuring tabs or spokes protrude only on one side of the device tip that is oriented towards the limbus and away from the eyelid may be helpful in ensuring that the measuring tabs do not become contaminated by touching the eyelids or eyelashes. In yet another variation, the measuring component, e.g., one having tabs or spokes as described above, may be configured to form a device tip that couples to a slidable shield by an interference fit. For example, as shown in the cross-sectional view of FIG. 60, device tip (3000) includes a measuring component (3002), notch (3004), and a needle stabilization mechanism, tunnel (3006). The device tip (3000) may be made from any suitable polymer, e.g., a polymer having a durometer between about 40 A and about 70 A, or between about 50 A and about 60 A. Alternatively, the device tip may be made from a polymer such as silicone or a thermoplastic elastomer, e.g., Medalist® MD-145 thermoplastic elastomer (50 A durometer) and Medalist® MD-555 thermoplastic elastomer (55 A durometer). A flange (3008) on the distal end of the shield (3010) correspondingly fits into notch (3004) to form the interference fit. Such an interference fit is beneficial because it may better hold the device tip within the shield.

Conduits

The intraocular drug delivery devices described here may include any suitable conduit (or dispensing member) for accessing the intraocular space and delivering active agents therein. The conduits may have any suitable configuration, but will generally have a proximal end, a distal end, and a lumen extending therethrough. For their first, non-deployed (pre-deployed) state, the conduits will generally reside within the housing. In their second, deployed state, i.e., after activation of the actuation mechanism, the conduit, or a portion thereof, will typically extend from the housing. By "proximal end" it is meant the end closest to the user's hand, and opposite the end near the eye, when the devices are positioned against the eye surface. In some variations, the drug conduit is removable or detachable from the drug reservoir. In other variations, the drug conduit is permanently (fixedly attached) to the drug reservoir.

The distal end of the conduit will generally be configured to be sharp, beveled, or otherwise capable of penetrating the eye surface, e.g., the sclera. The conduit employed may be of any suitable gauge, for example, about 25 gauge, about 26 gauge, about 27 gauge, about 28 gauge, about 29 gauge, about 30 gauge, about 31 gauge, about 32 gauge, about 33 gauge, about 34 gauge, about 35 gauge, about 36 gauge, about 37 gauge, about 38 gauge, or about 39 gauge. The wall of the conduit may also have any suitable wall thickness. For example, in addition to regular wall (RW) thickness, the wall thickness of the conduit may be designated as thin wall (TW), extra/ultra thin wall (XTW/UTW), or extra-extra thin wall (XXTW). These designations are well known to those of skill in the relevant art. For example, the conduit may be a fine gauge cannula or needle. In some variations, the conduits may have a gauge between about 25 to about 39. In other variations, the conduits may have a gauge between about 27 to about 35. In yet further variations, the conduits may have a gauge between about 30 to about 33. Use of a small needle gauge, for example a 31-33 gauge needle, may make the needle track through the sclera smaller and may minimize the risk of the drug backflow from the eye along with the egress of intraocular fluid following intraocular needle withdrawal.

In some variations, the outer diameter of the needle may be tapered from a wider needle base toward a narrower needle tip. In another example, the needle inner diameter may be tapered from a wider needle base toward a narrower needle tip. In yet another example, both the needle outer and inner diameters may be tapered from a wider needle base toward a narrower needle tip. For example, either or both needle diameters may be tapered from about 25 to about 27 gauge at the base toward about 31 to about 33 gauge at the tip, or from about 30 gauge at the base toward about 32 to about 33 gauge at the tip.

Figure 14A:
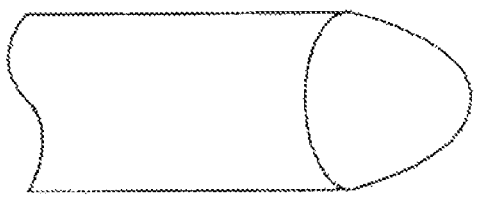
FIGS. 14A-14C show perspective views of exemplary sharp conduits.
Figure 14B:
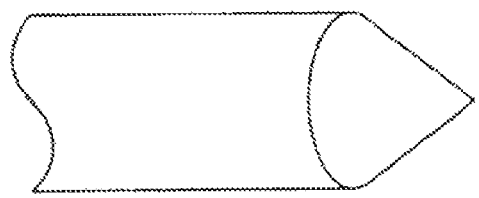
Figure 14C:
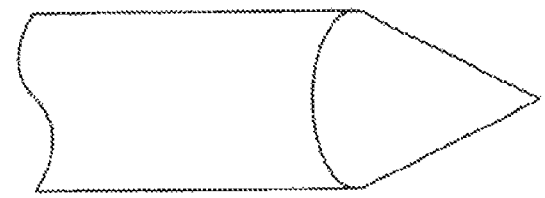

The conduits may have a sharp, pointed tip (FIGS. 14B-14C and FIGS. 15A1-15A2), rather than a rounded one (FIG. 14A) as in conventional needles. The pointed needle tip is formed by the lateral side surfaces that are straight at the point of their convergence into the tip, and at the point of their convergence forming a bevel angle (the angle formed by the bevel and the shaft of the needle), which may range from between about 5 degrees and about 45 degrees (FIG. 14B), between about 5 degrees and about 30 degrees, between about 13 degrees to about 20 degrees, or between about 10 degrees and about 23 degrees (FIG. 14C).

The sharp, pointed needle tip may provide improved penetration of the needle through the fibrillar, fibrous scleral tissue, which is the major structural cover of the eye and consists of a network of strong collagen fibers. Thus, such a needle tip during its penetration through the eye wall may create less resistance and, thus, decrease the impact force that is transmitted to the intraocular structures, such as the retina and the crystalline lens, in turn causing less damage to intraocular structures during the intraocular injection process (compared to conventional needles).

In addition, such a narrow bevel angle may enable the needle to cause less sensation when it penetrates through the eye wall (the outer cover of the said eye wall being richly innervated with sensory nerve fibers endings particularly densely located in the conjunctiva and cornea), which may be an issue when intraocular injections are involved compared to other less sensitive sites.

The narrow bevel angle may also allow for a longer bevel length and larger bevel opening and, thus, a larger opening at the distal end of the injection needle. With such a configuration, the force of drug injection into an eye cavity may be reduced, thus reducing the chances of intraocular tissue damage by a forceful stream of injected substance, which may occur with conventional short-beveled needles.

In some variations, the conduits are injection needles having one or more flat surface planes, as well as one or more side-cutting surfaces, as illustrated in FIGS. 16 and 17. Examples include a needle shaft comprising multiple surface planes separated by sharp ridges (FIGS. 16A-16C), as well as a needle tip comprising sharp side-cutting surfaces located on either side of the beveled surface of the needle about 90 degrees from the beveled surface (FIG. 17). The conduit may also be bi-beveled, i.e., have two bevels facing about 180 degrees from each other that is located on the opposite sides of the conduit. The conduit may also be coated (e.g., with silicone, PTFE, etc.) to facilitate its penetration through the eye wall.

Figure 18A:
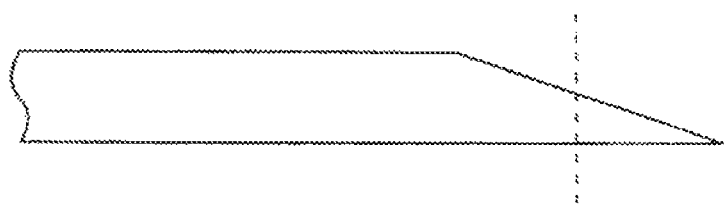
FIGS. 18A-18C show side and cross-sectional views (taken along line A-A) of an exemplary flattened conduit.
Figure 18B:
Figure 18C:

In other variations, the conduit may be configured to be wholly or partially flattened in at least one dimension, as shown in the cross-sectional view of FIG. 18C taken along the line A-A of FIG. 18A. For example, the conduit may be flattened in the anterior-posterior dimension (that is from the beveled side of the needle towards its opposite side. In one variation, both the external and internal surfaces of the needle are flattened and represent ovals on cross-section. In another variation, the internal surface of the needle is round and represents a circle on cross-section, while the external surface of the needle is flattened to enable its easier penetration through the fibrous scleral or corneal tissue of the eye wall. In another variation, more than one external surface plane of the needle is flattened to enable its easier penetration through the fibrous eye wall, while the internal opening of the said needle may be of any shape including round or oval.

As previously stated, in its second, deployed state, the conduit or needle extends from the housing. The portion of the needle that extends from the housing can be referred to as the exposed needle length. Upon activation of the actuation mechanism, the needle goes from its first, non-deployed state (pre-deployed state) (where it is entirely within the housing of the device), to its second, deployed configuration outside the housing, where a certain length of it is exposed. This exposed length may range from about 1 mm to about 25 mm, from about 2 mm to about LS mm, or from about 3.5 mm to about 10 mm. The exposed needle lengths may enable complete penetration through the eye wall and into the vitreous cavity, while minimizing the risk of intraocular damage. The exposed needle length may be adjusted according to the depth of needle penetration desired. In some variations, the exposed needle length ranges from about 1 mm to about 25 mm, or from about 1.5 mm to about 10 mm, or from about 2 mm to about 8 mm. Here the exposed needle lengths may enable complete intraocular penetration through the cornea into the anterior chamber, while minimizing the risk of intraocular damage. To illustrate, if the injection depth is too shallow, the drug could be injected into the choroid causing bleeding, or into the cortical gel causing a retina tear. If the injection is too deep, the jet stream or hydraulic wave generated by the injected drug could cause trauma to the lens or the retina/macula on the opposite side of the eye. An exemplary range of needle exposure past the external surface of the device tip is between about 4 to about 6 mm, or between about 2 to about 8 mm, or between about 1 mm to about 25 mm. If the injection depth is too shallow, the drug may leak out of the eye due to backflow of the intraocular fluid through the needle track. This may result in variable intraocular drug concentration following injections. To minimize this, it may be beneficial for the needle to (be exposed and) have a penetration depth of at least about 2 mm (or at least about 4 mm, or at least about 6 mm), and have a small needle gauge that may produce a self-sealing wound (for example 30 gauge or smaller, or in the range of 30-33 gauge).

Figure 19:
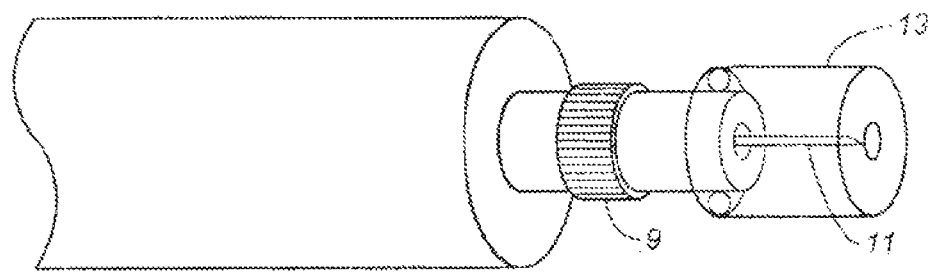
FIG. 19 shows an exemplary mechanism for controlling exposure of the conduit.
Figure 20:
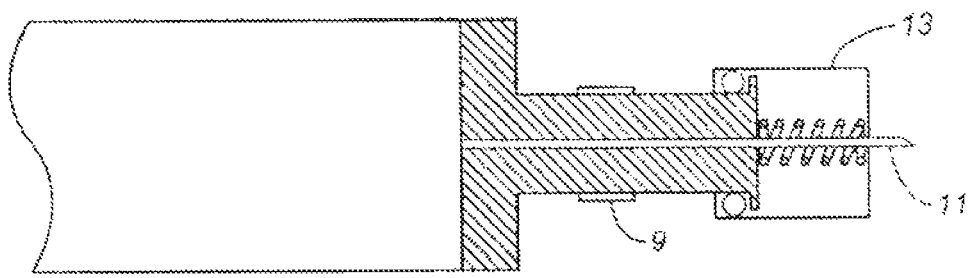
FIG. 20 provides another exemplary conduit exposure control mechanism.

In some variations, the devices may include an exposure control mechanism (9) for the dispensing member (11) (conduit) (FIGS. 19 and 20). The exposure control mechanism (9) generally enables one to set the maximal length of the dispensing member exposure during dispensing member deployment. In one variation, the exposure control mechanism works by providing a back-stop for the needle-protective member (13). In another variation, the exposure control mechanism (9) may be a rotating ring member with a dialable gauge. Needle exposure could be adjusted by the millimeter or a fraction of the millimeter, e.g., 1 mm, 1.5 mm, 2 mm, 2.5 mm, 3 mm, etc. Here the device may be equipped with a retraction mechanism that controls needle retraction into a needle-protective member. Such a needle-retraction mechanism may be spring-actuated (FIG. 20).

Figure 21:
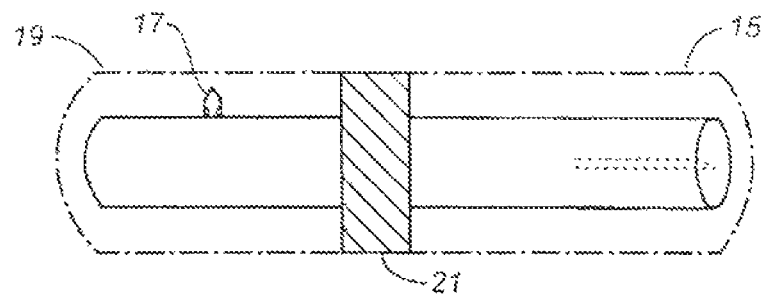
FIG. 21 shows an exemplary device having a front cover and back cover.

The devices may also include a removable distal (towards the eye) member that covers and protects the conduit (e.g., the front cover (15) in FIG. 21). In one variation, the devices may also include a removable proximal (away the eye) member that covers and protects the proximal part of the device, e.g., comprising a loading dock mechanism (17) (e.g., the back cover (19) in FIG. 21).

Figure 56:
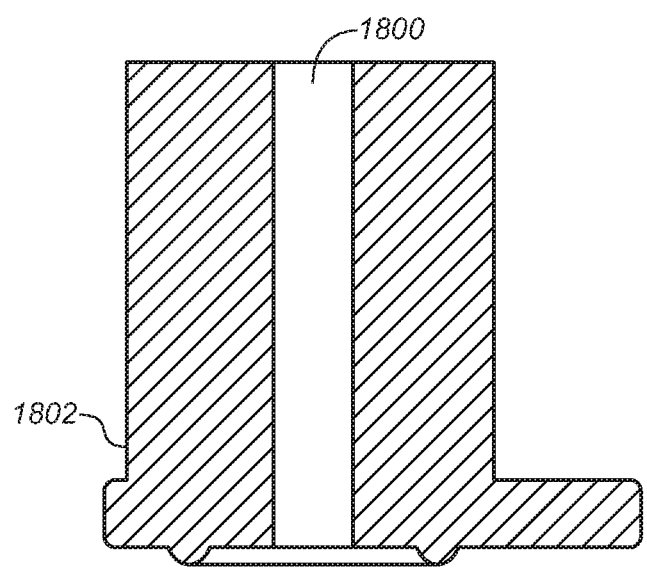
FIG. 56 depicts a cross-sectional view of an exemplary needle stabilization or needle guide mechanism.

Some variations of the devices described herein comprise a needle stabilization mechanism or needle guide mechanism configured to provide a steady and consistent needle alignment that is perpendicular to the ocular contact surface, and, therefore, perpendicular to the eye surface. This allows the operator to precisely control the angle of needle penetration into the eye by controlling the position of the device tip and housing relative to the eye surface. For example, the needle stabilization mechanism may be configured so that the needle exits the device tip through its central point (e.g., at the geometric center of a round tip) at 90 degrees relative to the tip outer surface (e.g., the ocular contact surface). Referring to FIG. 56, the needle stabilization mechanism may be configured as a tunnel (1800) that extends through the distal end of the device, e.g., through the ocular measuring component (1802) to open to the device exterior at the center of the device tip. In another variation, as shown in FIGS. 57A and 57B, the needle stabilization mechanism is configured as a sheath or scabbard (1902). In some instances, an injection angle other than 90 degrees (when the long axis of the device is not completely perpendicular to the eye surface at the injection site), may lead to inadvertent intraocular trauma to the crystalline lens or the retina. However, in other instances it may be useful for the needle to exit the tip at an angle less than 90 degrees relative to eye surface, in a direction parallel to the limbus.

In addition to allowing the injection needle to remain centered with respect to the injection device during the injection procedure, the needle stabilization mechanism may also be configured to include an anti-bending component that prevents bending of the needle while it is being advanced into the eye. In some variations, the needle stabilization mechanism is made of a non-deformable material, such as polycarbonate. In other variations, the needle stabilization mechanism is part of the slidable shield, or may be detachable or fixedly connected to the shield.

A drug conduit such as a needle used with the devices described herein may bend at its base (e.g., where it is inserted into the hub) or near the center of the needle shaft during advancement through the eye wall. The needle stabilization mechanism may be configured to support the needle as it is being deployed. Thus, the needle stabilization mechanism may have a certain length and/or inner diameter relative to the enclosed drug conduit. In general, the needle stabilization mechanism will have a minimal (and optionally uniform) length and/or maximum inner cross-sectional diameter. The needle stabilization mechanism may also be defined by a ratio of its length to its inner cross-sectional diameter (to distinguish an opening in a shield that would be relatively short). As previously mentioned, the needle stabilization mechanism may have a certain length and/or inner diameter (ID) relative to the dimensions of the enclosed drug conduit. For example, the needle stabilization mechanism may have an axial length of between about 5% to about 95%, about 20% to about 60%, or about 20% to about 50% of the needle axial length. In some variations, the needle stabilization mechanism has an ID ranging from about 30% to 100%, from about 50% to about 95%, or from about 50% to about 90% of the outer diameter (OD) of the drug conduit. In one variation, the ID of the needle stabilization mechanism is greater than the OD of the drug conduit. The needle stabilization mechanism or guide mechanism may allow the utilization of smaller gauge needles or larger gauge but thinner walled needles (as compared to conventional needles), which may be particularly beneficial when large molecular drugs that include peptides, proteins, antibodies, soluble receptors, etc., are delivered. In some variations, such a needle stabilization mechanism may be configured as a tunnel, sheath, or scabbard in which the needle is coaxially disposed. The needle may be completely covered inside its needle stabilization mechanism during the resting position. During needle deployment, about 4 mm to about 10 mm of the needle tip may be exposed outside of the needle stabilization mechanism. Furthermore, the needle stabilization mechanism may be configured so that the needle travels directly through it and into the eye without contacting air.

The central positioning and anti-bending features of the needle stabilization mechanism may be particularly beneficial in preventing bending of smaller gauge needles, for example 31 gauge to 35 gauge needles. The utilization of smaller gauge needles is particularly desirable for intraocular injections because the opening such a needle makes in the eye wall is smaller, thereby eliminating or reducing the back flush of intraocular fluid following needle withdrawal. Eliminating or reducing the backflush of intraocular fluid has other advantages. For example, communication between the outside environment and the interior of the eye is avoided or minimized (or the time period that the communication exists is eliminated or reduced), in turn reducing the risk of intraocular infection or endophthalmitis. Additionally, the use of a smaller needle gauge enhances patient comfort during intraocular needle penetration, which is inversely proportional to the needle gauge. Furthermore, the anti-bending and central positioning features are also beneficial when thin walled needles are utilized for intraocular drug delivery of high viscosity, high molecular weight, or large particle drugs.

Reservoirs

The reservoir is generally contained within the housing and may be configured in any suitable manner, so long as it is capable of delivering an active agent to the intraocular space using the actuation mechanisms described herein. The reservoir may hold any suitable drug or formulation, or combination of drugs or formulations to the intraocular space, e.g., the intravitreal space. It should be understood that the terms "drug" and "agent" are used interchangeably herein throughout. In one variation, the drug reservoir is silicone oil-free (lacks silicone oil or one of its derivatives) and is not internally covered or lubricated with silicone oil, its derivative or a modification thereof, which ensures that silicone oil does not get inside the eye causing floaters or intraocular pressure elevation. In another variation, the drug reservoir is free of any lubricant or sealant and is not internally covered or lubricated with any lubricating or sealing substance, which ensures that the said lubricating or sealing substance does not get inside the eye causing floaters or intraocular pressure elevation.

In some variations, the reservoir is made of a material that contains a cyclic olefin series resin, a cyclic olefin ethylene copolymer including commercially available products such as Zeonex® cycle olefin polymer (ZEON Corporation, Tokyo, Japan) or Crystal Zenith® olefinic polymer (Daikyo Seiko, Ltd., Tokyo, Japan) and APEL™ cycle olefin copolymer (COC) (Mitsui Chemicals, Inc., Tokyo, Japan), a cyclic olefin ethylene copolymer, a polyethylene terephthalate series resin, a polystyrene resin, a polybutylene terephthalate resin, and combinations thereof. In one variation, it may be beneficial to use a cyclic olefin series resin and a cyclic olefin ethylene copolymer that have a high transparency, a high heat resistance, and minimal to no chemical interaction with a pharmacological product such as a protein, a protein fragment, a polypeptide, or a chimeric molecule including an antibody, a receptor or a binding protein.

Exemplary agents may be selected from classes such as anti-inflammatories (e.g., steroidal and non-steroidal), anti-infectives (e.g., antibiotics, antifungals, antiparasitics, antivirals, and antiseptics), cholinergic antagonists and agonists, adrenergic antagonists and agonists, anti-glaucoma agents, neuroprotection agents, agents for cataract prevention or treatment, anti-oxidants, antihistamines, anti-platelet agents, anticoagulants, antithrombics, anti-scarring agents, anti-proliferatives, anti-tumor agents, complement inhibitors, vitamins (e.g., vitamin B and derivatives thereof, vitamin A, depaxapenthenol, and retinoic acid), growth factors, agents to inhibit growth factors, gene therapy vectors, chemotherapy agents, protein kinase inhibitors, tyrosine kinase inhibitors, PEGF (pigment epithelial growth factor), small interfering RNAs, their analogs, derivatives, conjugates, and modifications thereof, and combinations thereof.

Exemplary complement inhibitors include, but are not limited to, antibodies or blocking peptides that inhibit at least one complement protein or fraction (e.g., anti-C5 agents, including antibodies such as anti-C5a and anti-C5b agents, and ARC1905; anti-C3 agents and antibodies, such as anti-C3 and anti-C3b, and other complement inhibitors, complement fraction inhibitors, or combinations thereof.

Particular agent classes that may be useful include without limitation, antineovascularization agents, anti-VEGF agents, anti-platelet derived growth factor agents, antiplacenta delivered growth factor agents, anti-pigment epithelium delivered growth factor agents, anti-PDGF pathway blocking agents (e.g., a PDGF-beta pathway blocking agent such as anti-PDGF-beta aptamers (e.g., Fovista™ anti-PDGF therapy), antibodies, blocking peptides or blocking small molecules). anti-PDGF-beta receptor agents (e.g., a PDGFR-beta blocking agent such as an aptamer, antibody, blocking peptide, or a blocking small molecule), anti-vascular permeability agents, protein kinase C inhibitors, EGF inhibitors, tyrosine kinase inhibitors, steroidal anti-inflammatories, nonsteroidal anti-inflammatories, anti-infectives, anti-allergens, cholinergic antagonists and agonists, adrenergic antagonists and agonists, anti-glaucoma agents, neuroprotection agents, agents for cataract prevention or treatment, anti-proliferatives, anti-tumor agents, complement inhibitors, vitamins, growth factors, agents to inhibit growth factors, gene therapy vectors, chemotherapy agents, protein kinase inhibitors, small interfering RN As, aptamers, antibodies or antibody fragments, growth factor receptors and receptor fragments, analogs, derivatives, and modifications thereof, and combinations thereof. Further exemplary agents include an anti-complement fraction agent (e.g., an anti-C5 agent, anti-C5a agent, or anti-C3 agent) and aptamers, antibodies, and binding peptides thereof, and combinations thereof. In one variation, a combination of an anti-VEGF agent and an anti-PDGF agent is used.

Non-limiting, specific examples of drugs that may be used alone or as part of a combination drug therapy include Lucentis™ (ranibizumab), Avastin™ (bevacizumab), Fovista™ (anti-PDGF therapy). E10030 aptamer, Macugen™ (pegaptanib), anti-complement agents as described above, steroids, e.g., dexamethasone, dexamethasone sodium phosphate, triamcinolone, triamcinolone acetonide, and fluocinolone, taxol-like drugs, integrin or anti-integrin agents, vascular endothelial growth factor (VEGF) trap (aflibercept) (VEGF receptor fragments or analogs), anecortave acetate (Retaane), enzymes, proteases, hyaluronidase, plasmin, ocriplasmin, and limus family compounds, and combinations thereof. Non-limiting examples of members of the limus family of compounds include sirolimus (rapamycin) and its water soluble analog SDZ-RAD, tacrolimus, everolimus, pimecrolimus, and zotarolimus, as well as analogs, derivatives, conjugates, salts, and modifications thereof, and combinations thereof. In some instances it may be beneficial to employ a combination of agents. For example, it may be beneficial to combine two or more of the following for therapy: Lucentis™ (ranibizumab), Fovista™ (anti-PDGF therapy), Eylea® (aflibercept), an anti-PDGF agent, Macugen™, Jetrea™, a thrombolytic agent, and a steroid. In some instances it may be beneficial to combine Lucentis™ (ranibizumab) and Fovista™ (or another anti-PDGF agent) combination, or Eylea® (aflibercept) and Fovista™ (or another anti-PDGF agent).

Topical anesthetic agents may also be included in the reservoirs. For example, lidocaine, proparacaine, prilocaine, tetracaine, betacaine, benzocaine, ELA-Max®, EMLA® (eutectic mixture of local anesthetics), and combinations thereof may be used.

Some variations of the injection devices described herein include a filter that filters the contents of the reservoir as it is delivered into the eye. For example, the filter may be used to remove infectious agents and enhance sterility of an active agent formulation before injection into the eye. Thus, inclusion of a filter into the device may be useful because the eye is an immune-privileged site, and introduction of even a small quantity of pathogens such as bacteria may cause sight-threatening intraocular infection (endophthalmitis). The filter may also be used to remove impurities, e.g., silicone droplets, from an active agent formulation prior to injection into the eye. This may be useful for intraocular drugs because a small impurity injected into a subject's eye may result in the subject seeing it as floater(s) that may be intractable, which significantly worsens the quality of vision.

In one variation, the filter pore size is between about 0.1 µm (microns) and about 10 µm (microns), between about 0.2 µm (microns) to about 5.0 µm (microns), or between about 0.2 µm (microns) and about 10 µm (microns) to facilitate filtration of bacterial pathogens, particulate matter or impurities such as silicone droplets from the outgoing drug being injected intraocularly. Thickness of the said may range from between about 50 µm (microns) to about 250 µm (microns), or from between about 10 µm (microns) to about 10000 µm (microns).

The filter may be made from any suitable non-reactive material, such as a low protein-binding material. Exemplary filter materials include without limitation, thermoplastic fluoropolymers such as PVDF (polyvinylidene fluoride); thermoplastic polymers such as polyethylene and polypropylene; mixed cellulose esters; nylons; polyesters; nitrocelluloses; acrylic polymers such as Versapor® acrylic copolymer; polyethersulfones such as found in Super™ and Supor-R™ (Pall, Inc.) filters; a combination, a mixture, or a blend thereof.

The filter may be integrated with the device housing, the reservoir, the conduit, or any part of the device. In one variation, the filter is press-fit into a device lumen, for example into the lumen of a male-type luer, or a female-type hub, such as a drug conduit hub. In one variation, the filter is internal to the device. For example, the filter is configured to be inside the drug reservoir, or inside the conduit, or at the junction between reservoir and conduit. In another variation, filter is detachable or removable from the device. In one variation, the filter is located within the reservoir at its distal end, e.g., within the luer of a syringe. In another variation, the filter is located at the proximal end of the lumen of the conduit. The filter may also be placed at any location within and along the lumen of the drug delivery conduit, e.g., at its proximal end, in the middle, or at the distal end of the conduit.

In one example, the filter is integrated with the drug-loading conduit or device utilized to load a drug into the intraocular drug delivery devices described herein. For example, the filter is located inside the drug-loading conduit, or at or near the internal opening of the lumen of the drug-loading conduit. The filter may also be placed at any location within and along the lumen of the drug-loading conduit, e.g., at its proximal end, in the middle, or at the distal end of the conduit. For example, integrating a sterilizing filter within the drug-loading conduit may prevent microbial pathogens from room air from being introduced into the drug during the loading procedure.

In addition to removing infectious agents and/or impurities from the reservoir contents, the filter may function as a jet control mechanism that controls the force and limits the travel distance of the injected fluid as it exits the device and enters the eye. Other configurations of the jet control mechanism are also contemplated. The jet control mechanism may be generally configured to limit the maximum travel distance of the injected fluid to between about 5 mm and about 25 mm, between about 5 mm to about 20 mm, between about 5 mm and about 15 mm, or between about 5 mm to about 10 mm. In some instances, the maximum travel distance may be limited to less than about 25 mm, less than about 15 mm, less than about 10 mm, or less than about 5 mm. When a filter serves as the jet control mechanism, the pore size may range from about 0.05 µm to about 10 from about 0.1 µm to about 5 or from about 0.2 µm to about 1 Such a filter may also be placed within any portion of the device, e.g., near the device conduit.

The jet control mechanism may also include a fluid displacement control mechanism. The fluid displacement control mechanism may include a plunger rate control mechanism such as a mechanical interference, resistance component, or pneumatic control component that is configured to control the rate of plunger advancement within the reservoir of the device. The jet control mechanism may be beneficial because it improves the safety of intraocular drug injections, e.g., by minimizing the risk of serious adverse effects such as retinal detachment or other types of damage to intraocular structures by a forceful jet of fluid inside the eye.

It may also be advantageous to remove air from the reservoir contents before it is injected into the eye since the presence of intraocular air can result in unpleasant visual disturbances ("floaters"). The removal of air from a viscous composition, e.g., a viscous drug solution such as Lucentis® (ranibizumab injection), may be particularly beneficial. Thus, in some variations, the devices described herein may also include an air control mechanism for removing the amount of air introduced into the eye during intraocular drug administration. The air removal mechanism may be configured as a filter, a plurality of filters, a valve, a reservoir, or a combination of any of the foregoing. The air removal mechanism may be placed within any portion of the device, e.g., near the device conduit.

Some variations of the air control mechanism may include a hydrophobic filter or porous hydrophobic membrane that allows air through while retaining an aqueous drug solution. Exemplary materials that may be employed in the hydrophobic filters include without limitation, polytetrafluoroethylene (PTFE), Supor® R Membrane (Pall Corporation, Ann Arbor, Mich.), Versapor® R Membrane (Pall Corporation, Ann Arbor, Mich.), and other porous filter materials that have been coated or treated with a hydrophobic membrane such as Repel™ Acrylic Copolymer Membrane (Pall Corporation, Ann Arbor, Mich.). The pore size of the air removal filters may range from about 0.05 µm to about 50 from about 0.1 µm to about 10 or from about 0.2 µm to about 5 µm.

Some variations of the air control mechanism may include a distal extension of the drug conduit and its internal opening (or its holder or internal opening of the hub of the drug conduit) into the internal cavity of a syringe luer or drug reservoir (e.g., beyond the internal surface plane of the hub). Such distal extension of the drug conduit and its internal opening beyond the internal surface of its bub may prevent air bubbles from entering the drug conduit and being injected into the eye causing bothersome "floaters". For example, air bubbles passing by the drug conduit's internal opening during its priming may pass into the proximal part of the hub and get trapped there, or continue to pass for example through a filter (e.g., a hydrophobic filter) out of the hub. In addition, distally extended drug conduit's internal opening beyond the internal plane of its hub may prevent potential clogging of the drug conduit by the glue used to attach the needle to the hub. This way, the needle shaft rather than its distal open end will be glued into the hub, reducing the chance of glue clogging the needle or interacting with the drug.

In one variation, the drug conduit may comprise more than one internal and/or external diameter. For example, the proximal part of the drug conduit, some or all of which may penetrate the eye wall, may have a small internal and/or external diameter (e.g., 33 gauge, or within the 30 to 33 gauge range) whereas its distal portion may have a larger internal and/or external diameter (e.g., 30 gauge, or within the 25 to 31 gauge range). In one example, the proximal portion of the drug conduit comprises a narrower, 31 gauge or 32 gauge or 33 gauge needle, whereas the distal portion of the drug conduit comprises a wider, 25 to 30 gauge needle.

In some variations, the drug conduit comprises a needle with at least a portion being tapered (e.g., internal, external, or both internal/external diameter being narrower towards its proximal end). In one variation, the drug conduit comprises a needle with at least two portions, or the entire needle being tapered (e.g., narrower internal, external or both internal/external diameter towards its proximal end). This design allows for the distal portion of the drug conduit (that does not penetrate the eye wall or enter an eye cavity) to have wider diameter therefore reducing the overall resistance to the drug flow while maintaining patient comfort due to the small needle gauge coming in contact with the eye. Such drug conduit having reduced resistance to drug flow is particularly important when using large molecular size drugs (such as proteins and other biopharmaceuticals), small-gauge needles (such as 30 to 33 gauge needles), or using distally extended and elongated needles described herein.

In one variation, the distal extension of the drug conduit may be able to puncture a membrane or cap covering the proximal entrance into the drug reservoir cavity, for example a syringe luer. This may be used with loadable and prefilled drug reservoirs or syringes, and may ensure the air-free drug injection.

The devices described herein may further include a terminal sterilization mechanism that includes a filter for removing infectious agents and particulate matter (as previously described) alone, or in combination with an air removal mechanism, e.g., an air removal filter. The terminal sterilization mechanism generally removes bacteria and particles from the drug solution as it exits the device and enters the eye. The inclusion of a terminal sterilization mechanism may help to minimize the risk of intraocular infection or inflammation such as endophthalmitis or sterile uveitis. The terminal sterilization mechanism may be configured as a filter comprising a hydrophilic membrane that is placed within any portion of the device, e.g., near the device conduit. The pore size of such a filter may range from about 0.05 µm to about 10 from about 0.1 µm to about 5 or from about 0.2 to about 1 In some variations, the filter is a non-protein binding or low protein-binding filter. Here exemplary hydrophilic filter materials include without limitation, thermoplastic fluoropolymers such as polyvinylidene fluoride (PVDF), mixed cellulose esters, nylons, polyesters, nitrocelluloses, and combinations, mixtures, or blends thereof. In one variation, the hydrophilic filter is treated with an oleophobic material to repel oil. The oleophobic material may be silicone oil.

It is understood that the injection devices described herein may include an air removal mechanism, a terminal sterilization mechanism, a jet control mechanism, or any combination thereof. When a plurality of filters are employed (e.g., in a filter assembly), both hydrophobic and hydrophilic filters may be used. In some instances, non-protein binding or low protein-binding filters are used. For example, as shown in FIG. 53, a filter (1510) may be provided near the device conduit (needle, 1514) that removes bacteria and particles, and which also controls the travel distance of the injected fluid. Thus, filter (1510) functions as both a terminal sterilization mechanism and a jet control mechanism. Additionally, an air removal mechanism (1512) may be included near the device conduit (needle, 1514). The air removal mechanism (1512) may comprise one or more openings in hub (1502) that communicates with the area external to the device, or a pouch or chamber that collects air. The openings and pouch/chamber may or may not include a filter or a valve.

An air removal mechanism may be particularly beneficial when an air bubble in a drug solution or suspension covers a substantial amount of the surface area of a poorly gas-permeable membrane such as a hydrophilic membrane. The air bubble generally increases resistance to flow of the drug composition, in turn decreasing its flow rate, to thereby cause an airlock. In other instances, e.g., when a fine pore hydrophilic membrane with a small surface area is utilized (that is poorly permeable to air), small air bubbles can aggregate on its surface and fuse into larger air bubbles that may eventually cause an airlock. Here the hydrophilic filter membrane may have a surface area less than about 25 mm$^2$, or less than about 9 mm$^2$, or less than about 4 mm$^2$. In another example, the effective filtration surface area of a hydrophilic membrane may be between about 0.1 mm$^2$ and 100 mm$^2$, or between about 1 mm$^2$ and 25 mm$^2$.

As a solution to the problem described above, a drug delivery device (e.g., an injector device) may be provided that comprises a gas-resistance component (e.g., a hydrophilic filter) and a vent (e.g., a hydrophobic filter). A hydrophilic filter membrane may increase the resistance to air or gas flow and prevent it from passing through a drug conduit while also diverting it through a hydrophobic filter vent and out of the device to facilitate air or gas removal from the drug composition. The vent and gas-resistance resistance components may be adjacent to each other. The vent and gas-resistance components may also be integrally formed with the needle hub or provided as separate, attachable/detachable components. The gas-resistance component may be at least partially air-impermeable under any condition, or at least partially air-impermeable under certain conditions, e.g., when wetted. The gas-resistance component may prevent air in the drug composition from entering a drug conduit. The vent may provide an anti-airlock mechanism, or a gas (air)-removal mechanism. For example, the vent may comprise an air-release valve or a hydrophobic membrane.

In some variations, the gas-resistance component may comprise a sterilization filter. For example, the gas-resistance component may include a hydrophilic membrane, such as a hydrophilic membrane filter that produces filter-sterilization of the drug composition as it passes through it and is ejected from the device. The hydrophilic filter membrane may be flat, convex, or concave in order to facilitate aggregation and fusion of small air bubbles into larger ones, to help with their removal by the air-removal component. In other variations, the pore size of the hydrophilic membrane may be small, making it less permeable to air and causing small air bubbles to aggregate on its surface and fuse into larger bubbles. The larger bubbles may enhance their removal by the air-removal component. The gas-resistance component may comprise a hydrophilic membrane with a pore size ranging between about 0.02 μm and about 5 μm, or about 0.1 μm and about 1 μm. Some variations of the hydrophilic membrane may have a pore size of about 0.2 μm.

In yet further variations, the drug delivery device may include an oil-removal component. In one example, the oil-removal component is part of, e.g., removable attached to, or integrated with, a terminal sterilization component. The oil-removal component may be a combination of a hydrophilic/oleophobic filter and at least one hydrophobic/oleophilic filter adjacent to or in close proximity to the hydrophilic filter. Oleophobic and oleophilic coatings may also be used to impart oleophobic or oleophilic properties to the filters.

Other filter structures and filter assembly configurations are also contemplated. For example, in some instances the filter may be structured to include a hydrophilic center and a hydrophobic periphery, or vice versa. These filters may have any suitable shape and geometry, e.g., the filters may be shaped to be flat, concave, convex, or discoid. In some variations, the filter assembly comprises filters of different types, e.g., a first filter and a second filter, where one is hydrophilic and the other is hydrophobic. When dual filters are employed, the filters may be arranged so that they are adjacent one another. The filters may be positioned so that a certain angle is formed between their surfaces, e.g., an angle between about 45 degrees and about 135 degrees, or between about 70 degrees and about 110 degrees. In some variations, the angle between the hydrophilic and hydrophobic filters may be about 90 degrees. For example, a 90 degree angle may be formed by placing a hydrophilic filter in the needle hub near the proximal end of the needle lumen, and a hydrophobic filter(s) in the wall of the needle hub. The filter assembly may include more than two filters and/or more than two types of filters in certain instances.

Figure 55A:
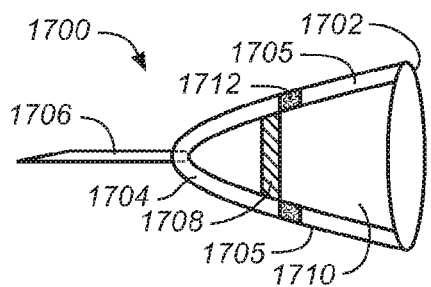
FIGS. 55A-G depict exemplary filter arrangements that include a hydrophilic filter and a hydrophobic filter.
Figure 55B:
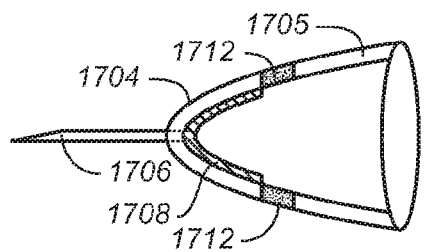
Figure 55E:
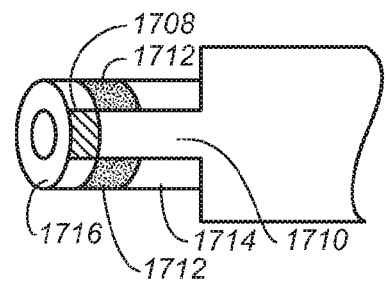
Figure 55C:
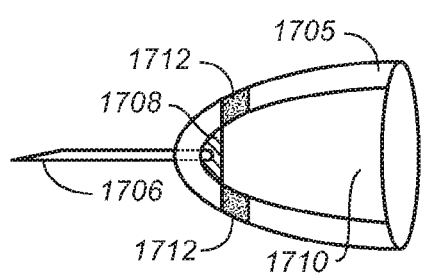
Figure 55F:
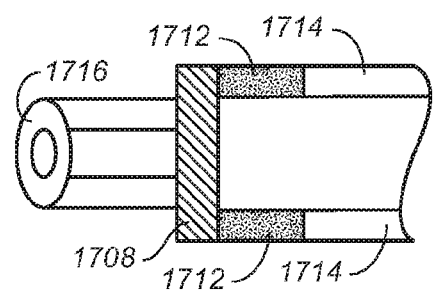
Figure 55D:
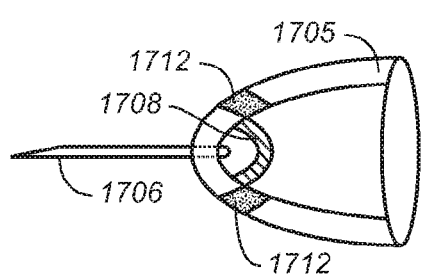
Figure 55G:
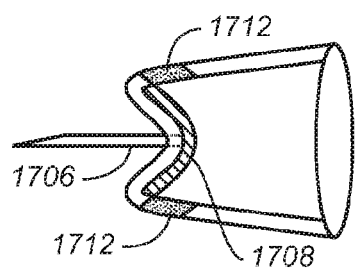

Referring to FIGS. 55A-55G, exemplary filter arrangements are shown. The filters may be placed in the needle hub or syringe luer, or if an integrated injection device is being employed, in the device wall near the proximal end of the needle or in the drug reservoir. In FIG. 55A, needle hub (1700) is shown having a proximal end (1702), a distal end (1704), a needle (1706) extending distally from the distal end (1704), and a wall (1705). Here the dual filter assembly includes a hydrophilic filter (1708) within the space (1710) defined by the needle hub wall (1705) positioned perpendicular (90°) to the axis of the needle (1706). Hydrophobic filters (1712) are disposed within the wall (1705). In FIG. 55B, the needle hub (1700) from FIG. 55A is shown, but hydrophilic filter (1708) follows the contour of the wall (1705) at the needle hub distal end (1704) to take a concave shape (with respect to the needle). In FIG. 55G, hydrophilic filter (1708) takes a convex shape (with respect to the needle).

Alternatively, as shown in FIGS. 55C and 55D, hydrophobic filters (1708) can be disposed within the wall (1705) and hydrophilic filter (1708) can be provided in the needle hub within the space (1710) defined by the needle hub wall (1705) near the proximal end of the needle. Hydrophobic filter (1712) may be shaped to be convex (with respect to the needle), as shown in FIG. 55D.

In an integrated device, as shown in FIGS. 55E and 55F, the space (1710) would be defined by the wall (1714) of the device instead of the wall of the needle hub, and some of the filters would be disposed within the wall (1714) of the device instead of the wall of the needle bub. The hydrophilic filter (1708) may be provided at the distal end (1716) of the device (FIG. 55E), or spaced proximal the distal end (1716) a certain distance (FIG. 55F). In both instances, the hydrophobic filters (1712) would be disposed within the device wall (1714).

The reservoirs and devices described here may be suitable for intraocular administration of a very small volume of a solution, suspension, gel or semi-solid substance. For example, a volume between about 1 μl and about 200 μl, or between about 10 μl and about 150 μl, or between about 20 μl and about 100 μl may be delivered. To that end, the device will generally have a very small "dead space," which enables intraocular administration of very small volumes.

The volume of a solution, suspension, gel or semi-solid substance may be even smaller when injected into the eyes of children, infants, or premature infants, where the intravitreal volume may be as small as about 4.0 ml. Thus, an injection device as described herein that is configured to inject such a small volume may be beneficial to use when treating retinopathy of prematurity or other diseases of the eye that affect these populations. Such a device may deliver a micro-volume of drug, e.g., a volume less than about 50 μl.

In some variations, the microvolume injector may deliver between about 5.0 µl to about 30 µl of drug. In other variations, the micro-volume injector may deliver between about 10 µl and about 25 µl of drug.

The housing of the micro-volume injector may have an outside diameter (OD) that is substantially the same, or the same, as that of a larger volume device. For example, the OD may range from about 3.0 mm to about 11 mm, from about 5.0 mm to about 10 mm, or from about 6.0 mm to about 9.5 mm. However, the drug reservoir within the housing will generally define an inner diameter (ID) that may be smaller. For example, the ID may range from about 1.0 mm to about 5.0 mm, from about 1.5 mm to 5.0 mm, or from about 2.0 mm and 3.0 mm, in order to precisely measure the a small amount of a drug solution.

In some instances, the smaller ID may be achieved by thickening the wall of the drug reservoir to measure, e.g., between about 1.0 mm and 3.0 mm, or between about 1.2 mm and about 2 mm. In another example, this could be achieved by expanding the OD within the grip/handle area only, for example, by adding an external handle, grip, or expander to increase the outer diameter (OD) of an area to range between about 3.0 mm and about 11.0 mm, or between about 5.0 mm and about 10 mm, or between about 6.0 mm and about 9.5 mm, while keeping the ID of the drug reservoir the same small size, for example, between about 1.0 mm and about 5.0 mm, or between about 1.5 mm and 5.0 mm, or between about 2.0 mm and 3.0 mm, throughout the entire or partial axial length of the drug reservoir. Thus, the wall thickness of the drug compartment may be thin (e.g., between about 0.7 mm and about 1.2 mm, or between about 0.8 mm and about 1.2 mm) in front of the handle/grip area in order to directly visualize the drug within the drug reservoir during drug loading, as well as to ensure complete air removal and to facilitate the priming of the device and drug conduit (e.g. needle).

In some variations, the internal radius of the reservoir of the injection device is configured to be proportional to the drug injection volume. Here the plunger travel distance (L) within drug reservoir is constant may equal 12.7 mm (+/−5 mm). Thus, for an incompressible fluid (e.g., a drug solution or suspension), the square of the internal drug reservoir radius is proportional to the drug injection volume. That is:

Injection volume=$\pi r2L$ and

L=Injection volume/$\pi r2L$;

where L is the plunger travel distance and r is the internal radius of the drug reservoir.

Using these formulas, the plunger travel distance and internal radius of the reservoir can be tailored to optimize delivery of small injection volumes. For example:

For an injection volume of 0.05 ml and a length (L) of 12.7 mm, the radius will be 1.12 mm;
For an injection volume of 0.05 ml and a length (L) of 7.7 mm, the radius will be 1.44 mm;
For an injection volume of 0.05 ml (L) and a length of 17.7 mm, the radius will be 0.95 mm;
For an injection volume of 0.03 ml and a length (L) of 12.7 mm, the radius will be 0.87 mm;
For an injection volume of 0.03 ml and a length of 7.7 mm, the radius will be 1.11 mm; and
For an injection volume of 0.03 ml and a length of 17.7 mm, the radius will be 0.74.

Figure 62A:
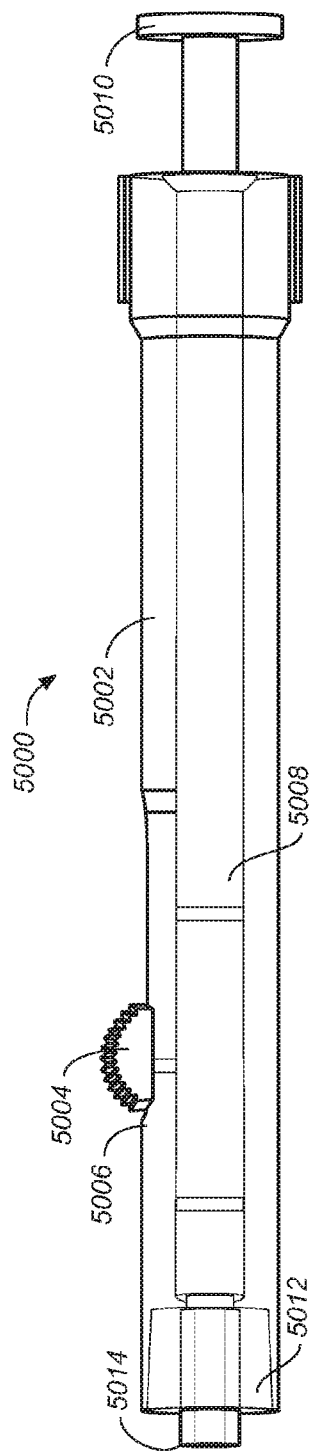
FIGS. 62A-62B depict another injection device according to a further variation.

In one variation, and as shown in FIG. 62A, the intraocular injection device (5000) for delivering a pharmaceutical formulation into the eye includes a housing (5002) (e.g., a syringe barrel), a small volume reservoir disposed within the housing and configured as described above (dimensions are defined by the radius and plunger travel distance) to deliver about 0.03 to about 0.05 ml of the formulation, and a plunger actuation lever (5004) that extends through a slot (5006) in the side (lateral) wall of the housing, and which is fixedly attached to a portion of the plunger (5008). The plunger actuation lever (5004) may be manipulated by a fingertip, and may help to deliver small volumes and/or low viscosity formulations requiring less force but higher jet stream control. A back plunger (5010) may also be included (e.g., by attachment to plunger (5008)) for devices that deliver viscous fluids. Thus, the plunger here may be considered a rear-side plunger. The use of a back plunger may help with the injection of larger volumes and/or viscous fluids that require increased force application to advance the plunger that is substantially disposed within the housing. A resistance component is not included in this particular design of the injection device. The housing (5002) can be used with commercially available detachable needles or with the injector attachments described herein by attachment to luer (5014).

Figure 62B:
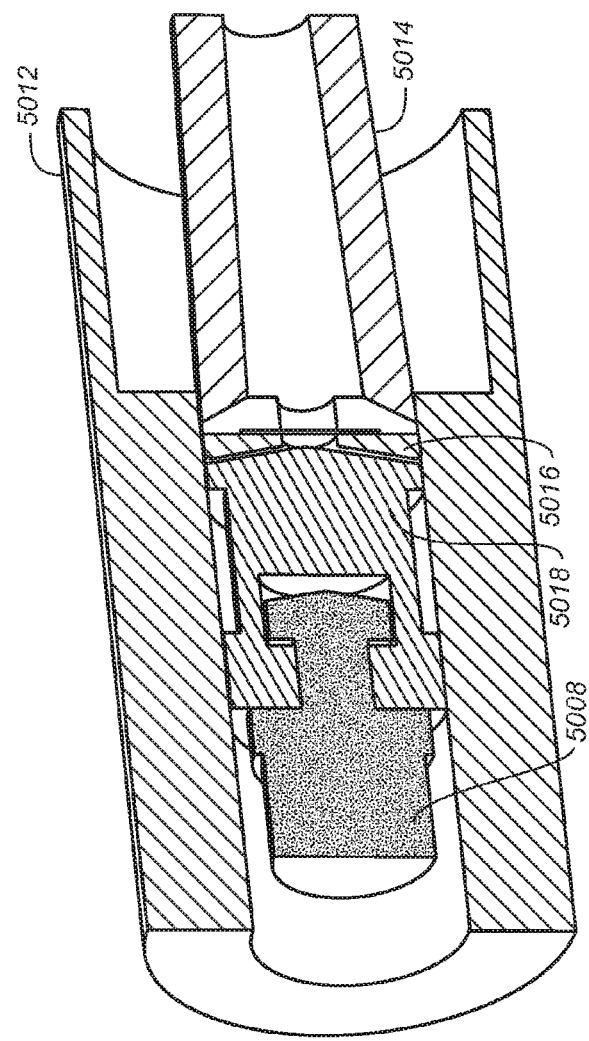

An expanded, cross-sectional view of the housing tip (5012) is shown in FIG. 62B. Here the housing tip (5012) includes a hydrophilic filter (5016) at the distal end of the plunger travel path. In the figure, the filter (5016) is depicted as being distal to the plunger seal (5018) but proximal to luer fitting (5014). Some variations of the device may be configured the same as that shown in FIG. 62A, but without the hydrophilic filter.

The device reservoirs may be pre-loaded during the manufacturing process or loaded manually before the intraocular injection, as further described below.

Drug Loaders

Front loading of an injection device when the drug is loaded through the injection needle generally dulls the needle tip and removes at least some of the lubricant coating from the needle making it more difficult and uncomfortable for the needle to penetrate the target tissue. There is also a higher risk of contaminating the injection needle while manipulating it with a drug container. Back loading, for example through the plunger, often leads to wasting a significant amount of the drug, for example, more than 0.05-0.1 mL, which is undesirable with expensive agents, as well as when smaller drug volumes are used, as is typically the case for intravitreal injections. Here total volumes in the range of 0.05-0.1 ml are generally used. When a detachable needle is used, drug may be lost in the syringe luer and needle bub when the loading needle is exchanged with an injection needle, and contamination of the sterile drug conduit may occur. Thus, it would be beneficial to have a front or side-loading mechanism that allows for direct loading of the drug into drug reservoir without passing the drug through the tip of the drug conduit, exchanging or detaching the drug conduit, or losing a significant volume of the drug during the loading process.

Figure 22:
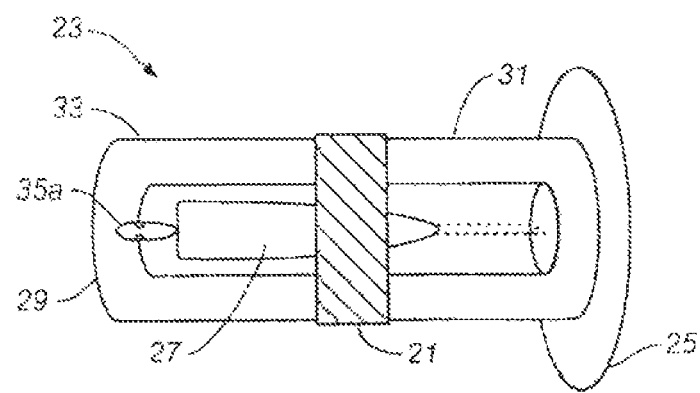
FIG. 22 illustrates how the device may be filled with a pharmaceutical formulation using an exemplary drug loading member.

In view of the above, when a drug or formulation is to be loaded into the reservoir of the devices described herein prior to intraocular injection, a loading member may be employed. The loading member may be removably attached to the distal end of the housing. For example, the loading member may function as a loading dock that quantitatively controls the volume of a liquid, semi-liquid, gelatinous, or suspension drug that is to be loaded into the device. For example, the loading member may comprise a dial mechanism (21) that allows the operator to preset a particular volume of a drug to be loaded into the device (FIGS. 21 and 22). The loading may occur with a precision raging from about 0.01 μl and about 100 μl, or from about 0.1 μl and 10 μl. Such a loading member may allow for loading the device reservoir with a liquid, semiliquid, gelatinous or suspended drug in a particular volume equal or less than that of the drug storage container, which allows for airless loading of the drug into the device. This may be beneficial because air injected into the eye will result in the sensation of seeing "floaters" by the patient, which may be uncomfortable and distracting to the patient particularly during driving or other similar activities.

As shown in FIG. 22, the drug loading mechanism (23) includes a wide base member (25) for upright loading of the reservoir (27) through its proximal (further from the eye) end (29). Also shown are exemplary front (31) and back (33) covers, as well as a dialable control mechanism (21) for setting the loading and/or injection volume(s). In other variations, the devices comprise a loading mechanism such as a loading dock (35A), wherein the dock (35A) interfaces with a drug storage container (FIGS. 25A-25B) such as a vial known to those skilled in the art and penetrates through the vial stopper to gain access to the drug contained inside the vial so that the drug could be loaded into the device reservoir. In FIGS. 25A-25B, the dock mechanism is located in the dependent position so that the drug vial (37) is positioned directly above the dock so that the drug moves from the vial downward in the direction of gravity.

In one variation, the dock mechanism comprises a needle or a sharp cannula that has openings or fenestrations (39) at its base. The said openings or fenestrations are positioned immediately adjacent to the internal aspect of the vial stopper when the loading dock penetrates into the drug vial while in the desired loading position, which in turn enables airless drug loading into the device as well as complete drug removal from the storage container. Airless drug loading may be beneficial because it may prevent the patient from seeing small intraocular air bubbles or "floaters." Complete drug removal is also beneficial given that small drug volumes and expensive medications are typically used.

Some variations of the loading mechanism comprise a cannula or needle. The length of such a needle or cannula is sufficient to penetrate into the lumen of the drug reservoir. In one example, the length of the loading needle or cannula is such that its tip reaches the opposite wall of the drug lumen when it is inserted perpendicularly to the device wall, in order to minimize the amount of air bubbles formed during drug loading. For example, the length of the loading needle or cannula is between about 0.1 mm and about 5 mm.

In other variations, for example, when the devices have a flat side surface (FIGS. 24A-24D) or a flat front or back surface (FIG. 22), the loading mechanism includes a loading dock located 180 degrees from the flat surface. This results in a loading clock pointing straight upwards, which enables its penetration into a drug container in the dependent position, which in turn enables airless drug delivery into the device, as well as complete drug removal from the storage container and its loading into the said device without drug retention and loss in the storage container.

In further variations, as shown in FIGS. 33A-33B, an access port (loading port) (144) may be provided at the distal end of the needle assembly (125) that allows drug from a storage container (146) to be loaded into the reservoir (122). Access port (144) may be placed at any suitable location on the needle assembly (125) or housing (102) to provide access to the reservoir. For example, if desired, the access port may be placed in the front wall (i.e., side or lateral wall) of the housing or even the ocular contact surface (not shown) so that drug loading occurs from the front of the device. The lateral access port may be configured to load drug through the wall of the device housing and into the reservoir in a manner that directs the drug toward the plunger seal and away from the internal opening of the injection needle, or along the surface of the plunger seal with an angle between 0 degrees (i.e., parallel to the seal surface) and about 70 degrees. This way the small amount of the medication to be loaded does not get splashed over the front part of the drug reservoir. In some variations, the lateral access port is round or oval. When the access port is round, it may have a diameter ranging from between about 1.0 mm and 5.0 mm. The lateral access port may be positioned at about a 1 degree to about a 90 degree angle with respect to the axis of the plunger. With this orientation, direct visualization of drug loading may occur while moving the plunger. In some variations, an injection device is configured to include a loading port at the front end of the device (e.g., distal end of the housing) that extends through the side wall of the housing. The loading port may or may not be near a side trigger. In other variations, the injection device may be configured to include the combination of a side loading port, a shielded needle, and a resistance component.

Access port (144) may comprise a seal or a plug configured to seal the reservoir against air or fluid leak, and/or external bacterial contamination and may be made from any suitable material, e.g., silicone, rubber, or any soft thermoplastic polymer such as, but not limited to, polyurethane, Kraton™ styrenic block copolymers consisting of polystyrene blocks and rubber blocks, polyethylene, polypropylene, polyvinyl chloride, or combinations thereof that allows sealable penetration by a sharp conduit.

Figure 52A:
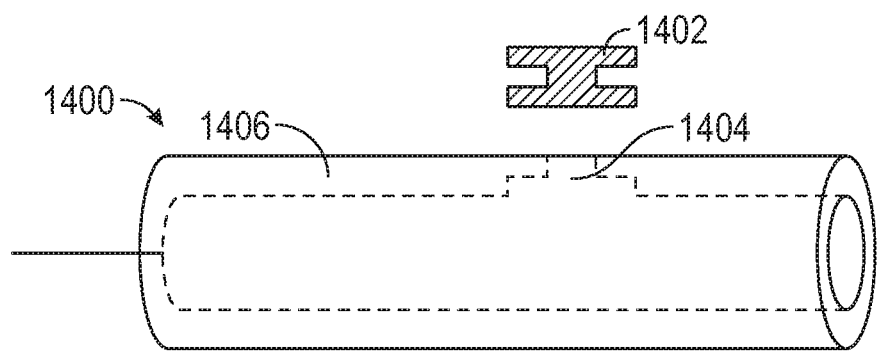
FIGS. 52A-52C show an exemplary access (drug loading) port in the injection device housing as well as an exemplary stopper for sealing an injection device access port, and how the location of the stopper corresponds with the location of an opening in a reservoir.
Figure 52B:
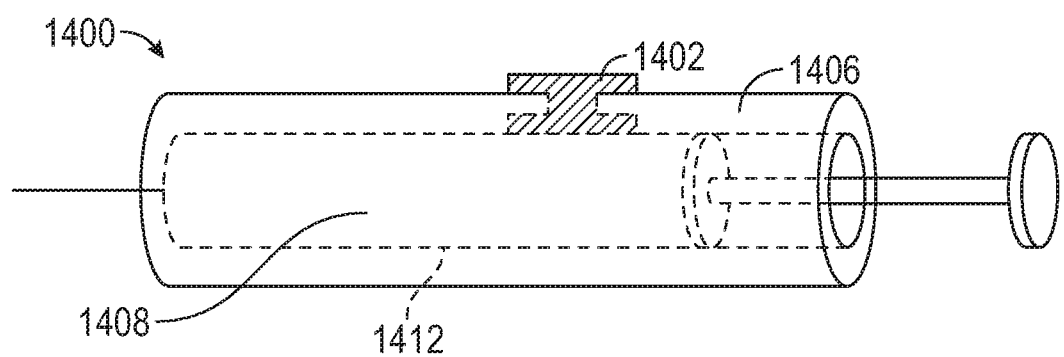
Figure 52C:
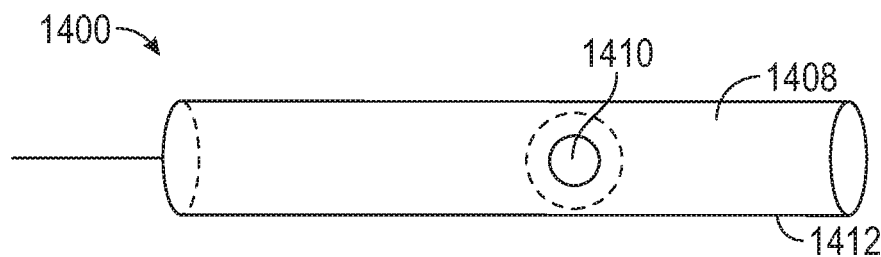

In some variations, the access port stopper or seal may comprise a fully or partially encircling sleeve. Here the sleeve may also serve as a finger grip or a holder. In another variation, and as shown in FIGS. 52A-52C, the injection device (1400) may include an H-shaped stopper or plug (1402) for sealing the access port (1404) that provides access through the housing wall (1406) of the device (1400) into the reservoir (1408). An opening (1410), e.g., in the wall of a needle assembly (1412) that contains the reservoir (1408), may be provided so that drug loading may occur through the access port (1404) and opening (1410) into the reservoir (1408). Here the H-shaped stopper or plug (1402) is flush with the internal surface of the reservoir (1408) when it is inserted to seal the access port (1404).

One or multiple membranes (148) may also be provided, e.g., in the ocular contact surface (108) to seal the internal compartment of the housing against air leak and/or external bacterial contamination. For example, the thickness of the membrane or the combined plurality of membranes may range from about 0.025 mm to about 5.0 mm, or range from about 0.1 mm to about 1 mm. One or multiple small apertures (150) may also be included in the wall of the housing (102) to help control air outflow from the housing (102). The number and diameter of the apertures (150) may be varied to control the rate of (needle assembly and) needle deployment.

In some variations, e.g., when a pneumatic actuation mechanism is used, drug loading may be controlled by a drug-loading piston. For example, as shown in FIG. 38, the device (400) may include a drug-loading piston (402) having a proximal end (404) and a distal end (406). The distal end (406) is adapted to include a threaded portion (408). Thus, during loading of a drug from container (410) through adaptor (412) and access port (414), the drug-loading piston (402) can be rotated and withdrawn to create negative pressure within the reservoir (416). This negative pressure in turn draws the drug through the needle (418) and into the reservoir (416). A receptacle (420) may also be provided at the distal end of the device for holding initially loaded drug prior to transfer into the reservoir (416).

Some variations of the drug loading devices include a filter that filters the contents of the drug container as it is delivered into the reservoir. For example, the filter may be used to remove infectious agents and enhance sterility of an active agent formulation before delivery into the reservoir. Thus, inclusion of a filter into the drug loader may be useful because the eye is an immune-privileged site, and introduction of even a small quantity of pathogens such as bacteria may cause sight-threatening intraocular infection (endophthalmitis). The filter may also be used to remove impurities, e.g., silicone droplets, from an active agent formulation as it is transferred to the reservoir and prior to injection into the eye. This may be useful for intra-ocular drugs because a small impurity injected into a subject's eye may result in the subject seeing it as floater(s) that may be intractable, which significantly worsens the quality of vision.

In one variation, the filter pore size is between about 0.2 µm (microns) and about 10 µm (microns) to facilitate filtration of bacterial pathogens from the outgoing drug being injected intraocularly. In another variation, the filter pore size is between about 0.1 µm (microns) and about 500 µm (microns) to facilitate filtration of particulate matter or impurities such as silicone droplets from the outgoing drug being injected intraocularly. In yet a further variation, the filter pore size is between about 0.2 µm (microns) to about 4.0 µm (microns). Thickness of the said filter may range from between about 50 µm (microns) to about 250 µm (microns), or from between about 10 µm (microns) to about 10000 µm (microns).

The filter may be made from any suitable non-reactive material, such as a low protein-binding material. Exemplary filter materials include without limitation, thermoplastic fluoropolymers such as PVDF (polyvinylidene fluoride); mixed cellulose esters; nylons; polyesters; nitrocelluloses; acrylic polymers such as Versapor® acrylic copolymer; polyethersulfones such as found in Super™ filters; a combination, a mixture, or a blend thereof.

The filter may be integrated with the drug loading device housing, the reservoir, a conduit, or any suitable part of the device. In another variation, filter is detachable or removable from the device. In one variation, the filter is located within the reservoir at its distal end. In another variation, the filter is located at the proximal end of the lumen of the conduit. The filter may also be placed at any suitable location within and along the lumen of the conduit, e.g., at its proximal end, in the middle, or at the distal end of the conduit.

Actuation Mechanisms

The devices described here generally include an actuation mechanism within the housing that deploys the conduit from the housing and enables the delivery of drug from the device into the intraocular space. In other variations, the conduit is deployed by an actuation mechanism contained within a separate cartridge that can be removably attached to the device housing, e.g., using snap-fit or other interlocking elements. The actuation mechanisms may have any suitable configuration, so long as they provide for accurate, atraumatic, and controlled delivery of drug into the intraocular space. For example, the actuation mechanisms may deliver a drug or formulation into the eye by way of intraocular injection at a rate ranging from about 1 µl/sec to about 1 ml/sec, from about 5 µl/sec to about 200 µl/sec, or from about 10 µl/sec to about 100 µl/sec. The actuation mechanisms may generally provide a force of needle deployment that is strong enough to penetrate the eye wall comprising the conjunctiva, sclera and the pars plana region of the ciliary body, but less than that causing damage to the intraocular structures due to high velocity impact. This force depends on several physical factors, including but not limited to, the needle gauge utilized, the speed/rate of needle deployment at the point of contact between the needle tip and the eye wall which in turn determines the impact force. An exemplary range of force that may be generated by the actuation mechanisms is about 0.1 N (Newton) to about 1.0 N (Newton). The velocity of needle deployment may also range between about 0.05 seconds and about 5 seconds.

In some variations, the actuation mechanism is a single-spring mechanism. In other variations, the actuation mechanism is a two-spring mechanism. In further variations, the actuation mechanism is pneumatic, e.g., employing negative pressure such as vacuum, or a positive pressure driven mechanism. In further variations, the actuation mechanism is driven magnetically or electrically, e.g., by a piezoelectric or magnetic rail mechanism. These types of actuation mechanisms may be configured to allow independent control of the rate and force of drug injection (controlled, e.g., by the first spring member in the two-spring variation), and the rate and force of the dispensing member deployment (controlled, e.g., by the second spring member in the two-spring variation). Exemplary two-spring mechanisms are shown in FIGS. 26 and 27.

Figure 28:
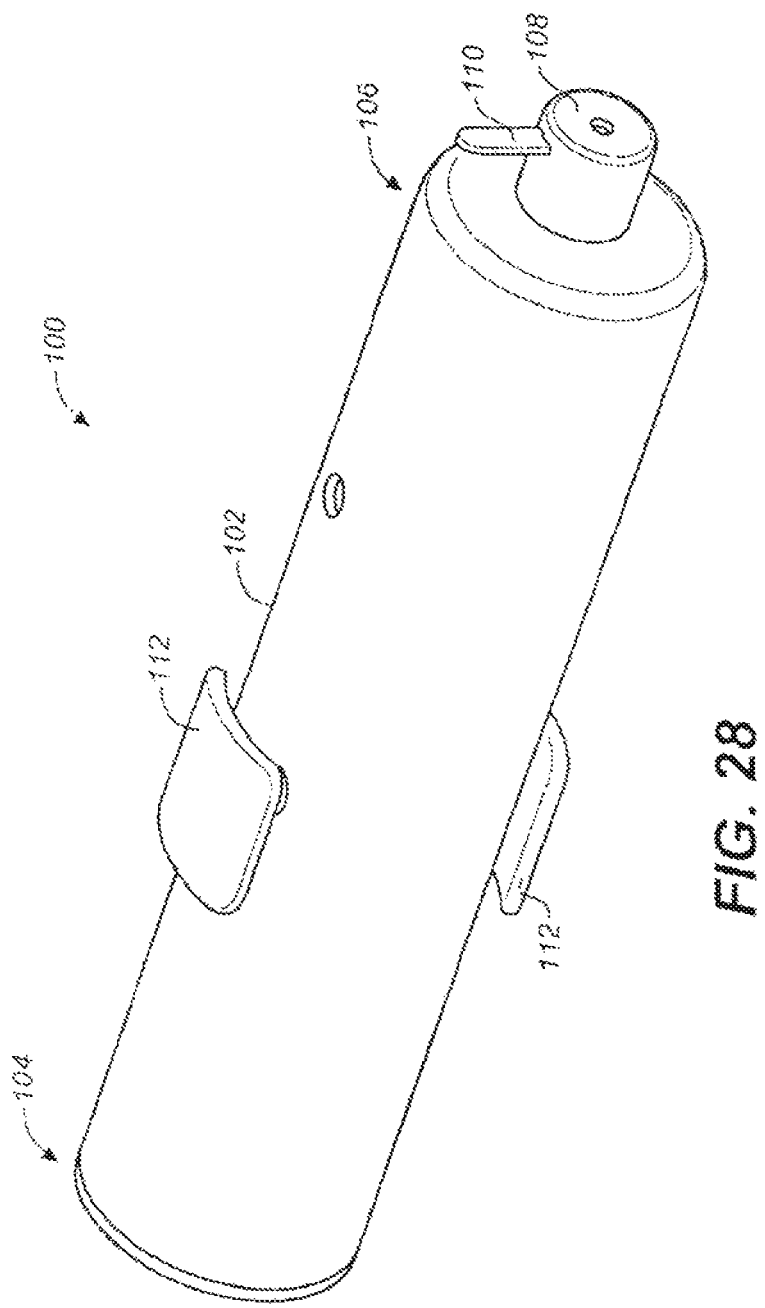
FIG. 28 depicts a perspective view of a device including a further example of a two-spring actuation mechanism in its pre-activated state.

FIG. 28 also depicts an exemplary integrated intraocular drug delivery device with a two-spring actuation mechanism. In FIG. 28, the device (100) includes a housing (102) having a proximal end (104) and a distal end (106). An ocular contact surface (108) is attached to the distal end (106). A measuring component (110) is attached to one side of the ocular contact surface (108). As further described below, a trigger (112) that is operatively coupled to the housing (102) works with the first spring (114) and the second spring (116) of the actuation mechanism to deploy pins (118) through openings (120) in the housing (102), to thereby deliver drug from the reservoir (122). First spring (114), second spring (116), pins (118), openings (120), and reservoir (122) are better shown in FIG. 29. Also in FIG. 29, a conduit, e.g., needle (124), is depicted within the housing in its first non-deployed state. Needle (124) is configured as being part of an assembly (125) such that movement of the assembly results in corresponding movement of the needle (124). A stop (115) is provided at the proximal end (127) of the assembly (125), which is connected to the distal end of the first spring (114) and the proximal end of the second spring (116). The springs, as well as other components of the device may be connected via medical grade adhesives, friction or snap fit, etc.

In FIG. 30, the second spring (116) is operatively connected to a plunger (132) by friction fit within a compartment (134) of the plunger (132). In the pre-activated state, as shown in FIG. 29, the plunger (132) and second spring (116) are held in place by pins (118). The pins (118) are removably engaged to the plunger (132) at plunger groove (138), and lock the plunger (132) in place via friction fit against the plunger groove (138) and housing (102).

Figure 31B:
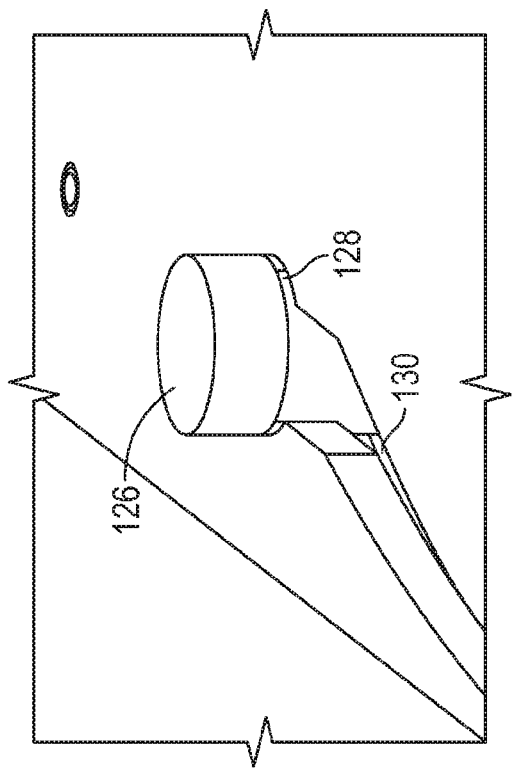
FIGS. 31A-31C illustrate how the trigger in FIG. 28 actuates the first spring of the two-spring actuation mechanism to deploy the conduit.
Figure 31A:
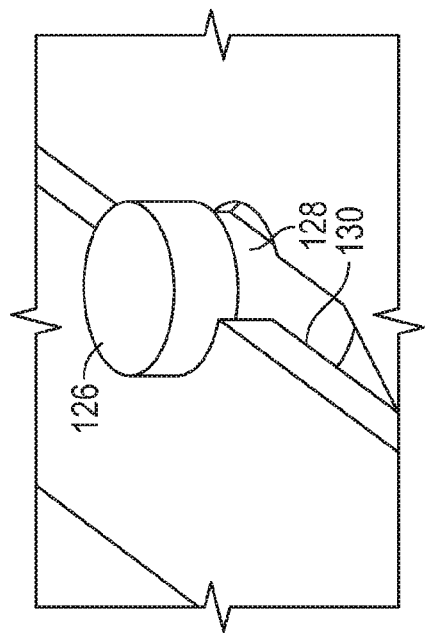
Figure 31C:
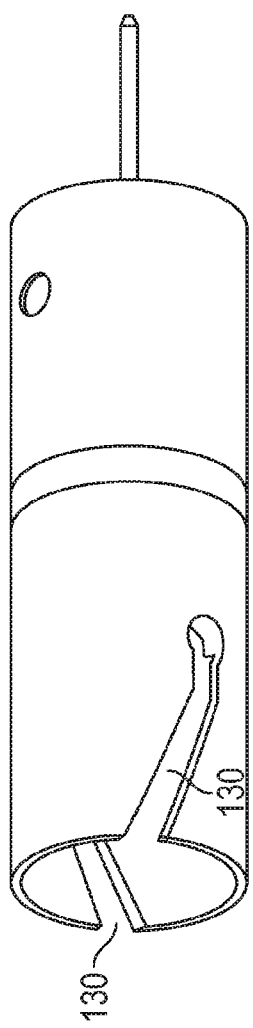

Activation of the first spring (114) of the actuation mechanism by activating the trigger deploys the needle (124) into the intraocular space, i.e., it moves the needle (124) from its first non-deployed state (FIG. 29) to its second deployed state (FIG. 30). Referring to FIGS. 30 and 31A-31C, activation of the first spring (114) occurs by depression of trigger (112) by, e.g., one or two fingers, which also depresses buttons (126). As shown in FIGS. 31A and 31B, buttons (126) are configured with a button groove (128) that allows the buttons (126) to align with channels (130) in the housing (102). Once aligned with the channels (130), the buttons (126) may be slidingly advanced along the channels (130). The channels may be of any suitable length. The distance from the distal end of the channel to the distal end of the housing may range from about 10 to about 20 mm. In one variation, the distance from the distal end of the channel to the distal end of the housing is about 16 mm. The rate of movement along the channels (130) may be controlled manually by the user, automatically controlled by the force of spring expansion, or a combination of both. This movement of the buttons (126) allows expansion of the first spring (114) against stop (115) so that the needle assembly (125) and needle (124) can be deployed. The channels in the housing may have any suitable configuration. For example, as shown in FIG. 31C, the channels (130) may be spiral cut within the housing to allow rotation or a corkscrew type movement of the needle upon advancement, which may facilitate needle penetration through the eye wall.

Figure 32A:
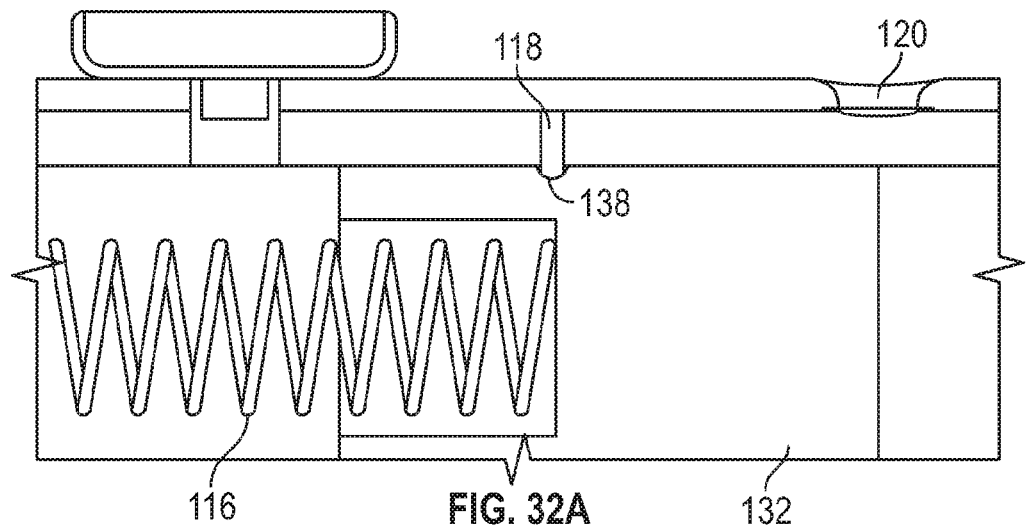
FIGS. 32A-32C are expanded views that illustrate how release of the locking pins in FIG. 28 work to activate the second spring of the two-spring actuation mechanism.
Figure 32B:
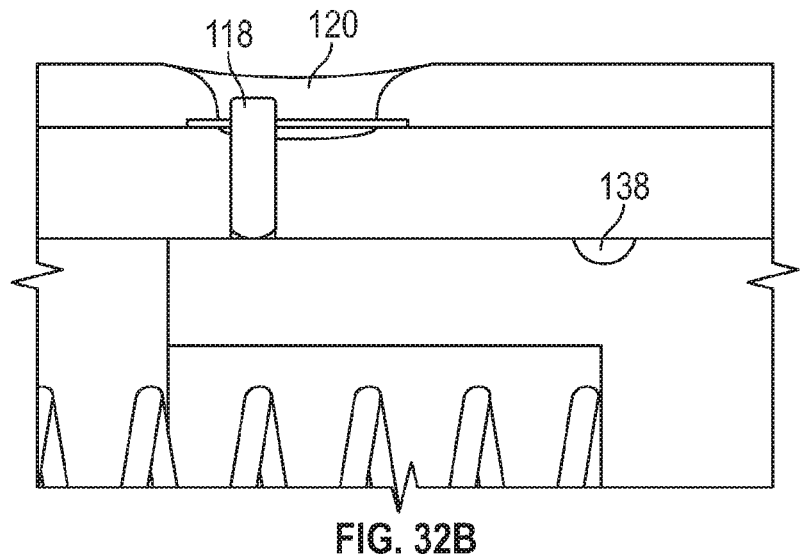
Figure 32C:
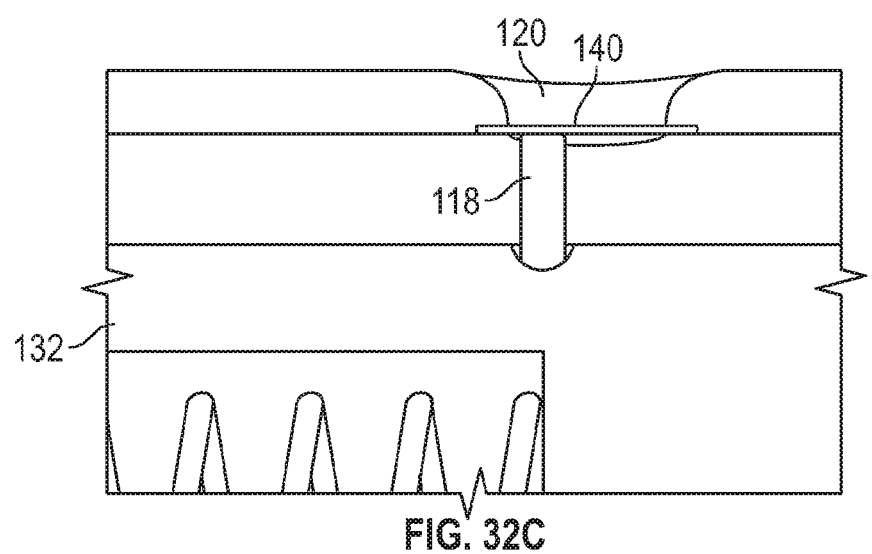

Activation of the first spring (114) will typically result in activation of the second spring (116) to deliver drug out of the device and into the intraocular space. For example, as shown in FIG. 30, the expansion force of first spring (114) against stop (115) that is also connected to the proximal end of the second spring (116) works to expand the second spring (116) so that the assembly (125) is advanced within the housing (102). As illustrated in FIGS. 32A-32C, when the pins (118) that are removably engaged to plunger (132) reach openings (120), they are deployed out through the openings (120). Expulsion of the pins (118) from the device, then allows free expansion of the second spring (116) against plunger (132), to thereby push drug residing with reservoir (122) out of the device. The openings (120) may be covered by a membrane or seal (140) that can be penetrated by the pins (118) to give a visual indication that the drug has been delivered.

A two-spring actuation mechanism, as shown in FIGS. 41A-41B may also be used. Referring to FIG. 41A, integrated device (600) includes an actuation mechanism comprising a first spring (602) and a second spring (604). In use, when trigger (606), e.g., a lever, is depressed, first spring (602) is released to advance shaft (608) in the direction of the arrow, which in turn advances needle (610) out of the tip of the device (600). Continued advancement of the shaft (608) advances the injection sleeve (612) and top seal (614) so that drug within reservoir (616) may be delivered through needle (610). Referring to FIG. 41B, once the drug has been injected, tabs (618) removably engage housing openings (620) to thereby release second spring (604), which then moves shaft (608) backward to retract needle (610) (not shown).

In some variations, a single-spring actuation mechanism is employed, as shown in FIGS. 36 and 37. When a single spring is used, the actuation mechanism is configured much like the two-spring mechanism described above except that the second spring is removed. Thus, in its pre-activated state, as shown in FIG. 36, a device (300) with a single spring (302) may activate the single spring (302) by depression of trigger (304) by, e.g., one or two fingers, which also depresses buttons (306). The buttons (306) are configured with a button groove (308) that allows the buttons (306) to align with channels (not shown) in the housing (310). Once aligned with the channels, the buttons (306) may be slidingly advanced along the channels. This movement of the buttons (306) allows expansion of the spring (302) against plunger (312) so that the needle assembly (314) and needle (316) can be deployed. When the pins (318) that are removably engaged to plunger (312) reach openings (320) within the housing (310), they are deployed out through the openings (320). Expulsion of the pins (318) from the device, then allows further expansion of the spring (302) against plunger (312), to thereby push drug residing with reservoir (322) out of the device. Although not shown here, the openings (320) may be covered by a membrane or seal that can be penetrated by the pins (318) to give a visual indication that the drug has been delivered.

Figure 34:
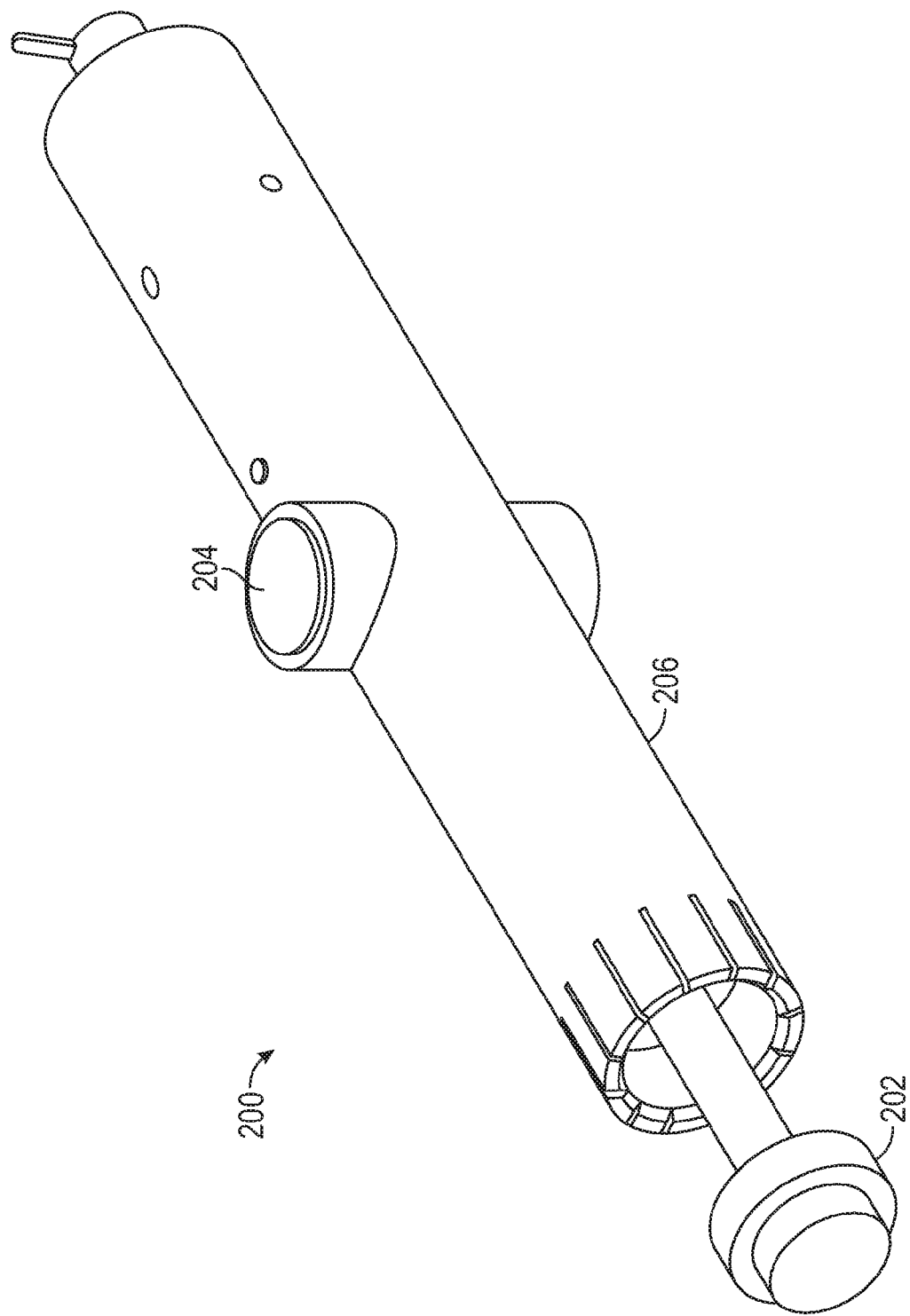
FIG. 34 is a perspective view of an exemplary device with a pneumatic actuation mechanism.

A pneumatic actuation mechanism may also be employed. In one variation, as depicted in FIGS. 34 and 35A and 35B, the pneumatic actuation mechanism includes a plunger, pins, and housing openings in the same fashion as described for the single- and two-spring mechanisms. However, instead of using a spring to deploy the needle assembly and plunger, a piston is used to slidingly advance the needle assembly within the housing. For example, in FIG. 34, a device with a pneumatic actuation mechanism (200) includes a piston (202) and trigger (204). The piston (202) is used to compress air into the housing (206) of the device (202). If desired, the amount of compressed air the piston includes in the device may be controlled by a dial or other mechanism (not shown). The proximal end of the housing may also be configured, e.g., with a flange, crimps, or other containment structure, that allows translational movement of the piston (202) into the housing but not out of the housing. Upon depression of a trigger (208), a pair of locking pins (210) are also depressed to thereby allow the compressed air generated by the piston (202) to push the needle assembly (212) forward. This advancement of the needle assembly (212) deploys the needle (214) out of the device (FIG. 35B). As previously stated, pins (216) similar to those above that lock the plunger (218) in place are also provided. Upon their expulsion from the device out of openings (220) in the housing (206) due to forward movement of the needle assembly (212), the compressed air further moves the plunger (218) forward to thereby push drug residing with reservoir (222) out of the device. Rotational pins (224) may also be included, which upon release by the sliding needle assembly (212) allow rotation of the needle assembly (212) with respect to the housing (206).

As previously stated, a trigger may be coupled to the housing and configured to activate the actuation mechanism. In one variation, the trigger is located on the side of the device housing proximate the device tip at the ocular interface surface (e.g., the distance between the trigger and device tip may range between 5 mm to 50 mm, between 10 mm to 25 mm, or between 15 mm to 20 mm), so that the trigger can be activated by a fingertip while the device is positioned over the desired ocular surface site with the fingers on the same hand. In another variation, the trigger is located on the side of the device housing at 90 degrees to the measuring component, so that when the ocular contact surface is placed on the eye surface perpendicular to the limbus, the trigger can be activated with the tip of the second or third finger of the same hand that positions the device on the ocular surface.

Some variations of the device may include a control lever for initiating plunger movement. In these instances, the control lever may actuate the plunger in a mechanical manner, e.g., by spring-actuation, similar to that described above. In other variations, actuation of the plunger may occur through a combination of mechanical and manual features. For example, the initiation of plunger movement may be aided by a manual force applied onto the control lever, while a spring-actuated mechanism for generating a mechanical force is also employed to move the plunger forward inside the device barrel to inject drug. In instances where the control lever is connected to the plunger, the initiation of plunger movement and drug injection is controlled by the manual component, whereas the rate of fluid injection is controlled by the mechanical force. Here a reduced manual force may be applied to the plunger due to its combination with a co-directional mechanical force, thus facilitating the stability of device positioning on the ocular surface at a precise injection site.

The control lever may be placed between 10 mm and 50 mm from the tip of the device that interfaces with the eye surface, or between 20 mm and 40 mm from the tip of the device. Positioning of the control lever in this manner may enable atraumatic and precise operation of the device with one hand.

Figure 43B:
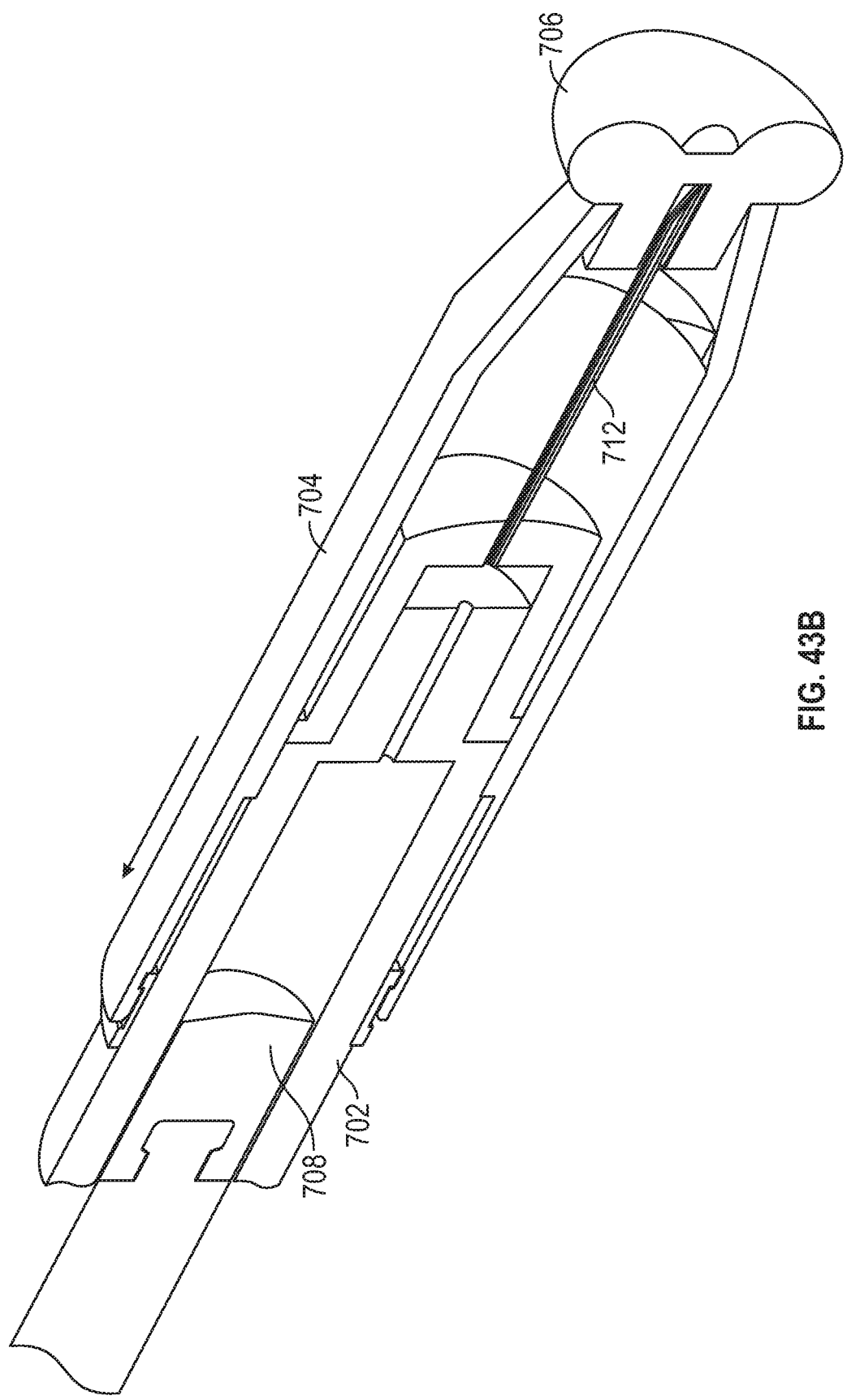
Figure 43C:
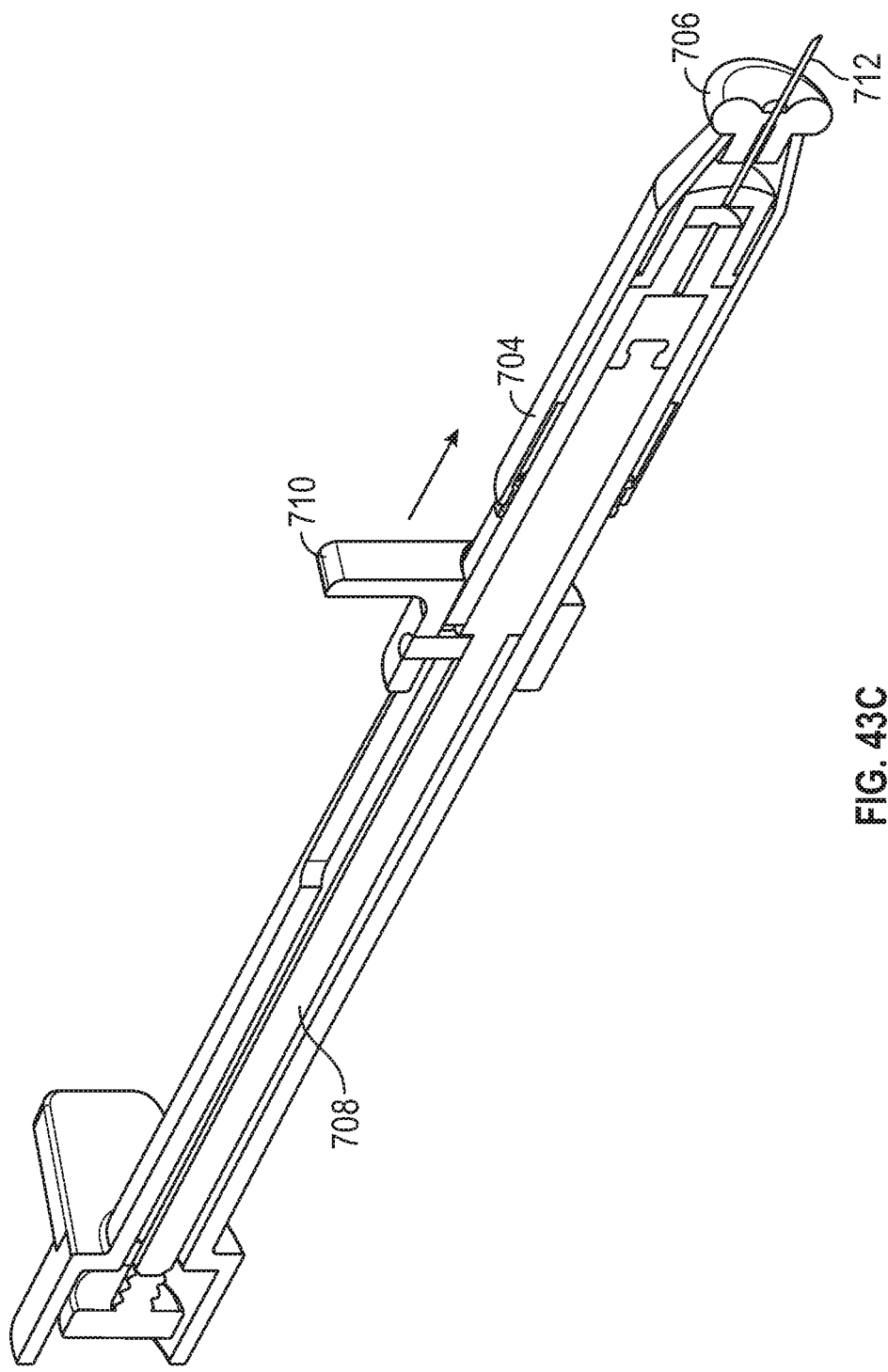
Figure 43D:
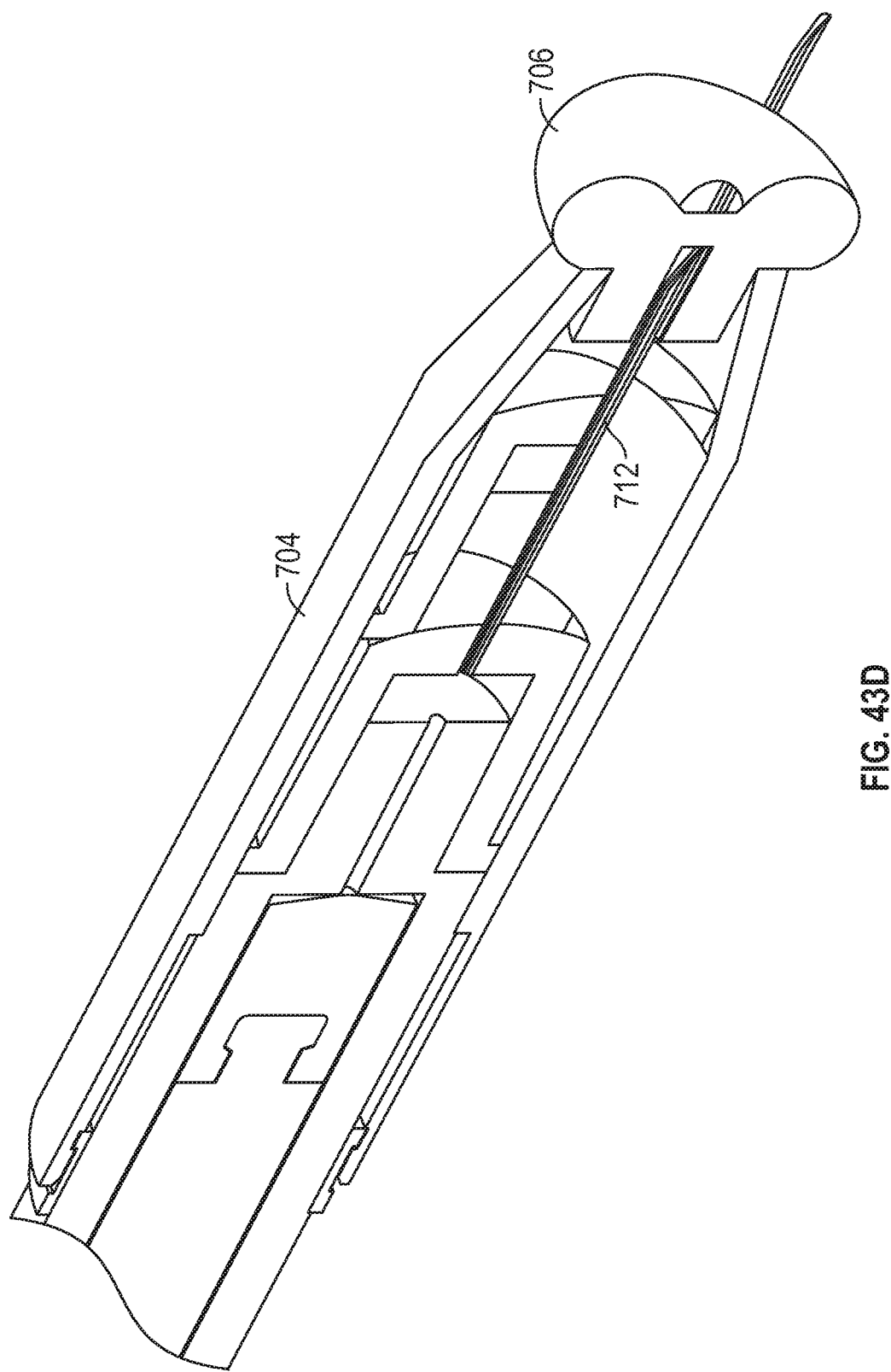

As illustrated in FIGS. 43A-43D, exemplary integrated device (700) includes a housing (702), a dynamic sleeve (704) slidable thereon, an ocular contact Surface (706), a plunger (708), and a control lever (710) for manually actuating the plunger (708) to inject drug through needle (712). An expanded sectional view of the ocular contact surface (706), dynamic sleeve (706), plunger (708), and needle (712) shown in FIG. 43A is shown in FIG. 43B. In use, after placing the ocular contact surface (706) on the eye, the applied pressure may automatically slide the dynamic sleeve (704) back (in the direction of the arrow) to expose the needle and allow needle penetration through the eye wall. The control lever (710) may then be slidably advanced manually (in the direction of the arrow in FIG. 43C) to advance plunger (708). When injection of the drug through the needle (712) is complete, the dynamic sleeve (704) may be slidably advanced manually to cover the needle, as shown in FIG. 43D.

The dynamic sleeve may be slidably advanced or retracted manually by a fine mobility control mechanism, also referred to as a mobility control mechanism. In these instances, the dynamic sleeve may comprise a high-traction surface located on the outer surface of the sleeve, which may aid movement of the sleeve with a fingertip. In one variation, the high-traction surface may be engraved or contain markings with a serrated pattern. In other variations, as shown in FIG. 45A, a platform or pad (e.g., a fingertip pad) (900) may be attached to the outer surface of the sleeve (902) to help manually advance or retract the sleeve. The platform or pad may also include a high-traction surface (904), the perspective, side, and top views of which are illustrated in FIGS. 45B, 45C, and 45D, respectively. Platform or pad (900) will typically include a base (912) for attachment to the sleeve (902). Base (912) may be of any suitable configuration. For example, the base of the platform or pad may be configured as a cylinder (FIG. 45H) or with a narrowed portion (portion of lesser diameter), such as a dumbbell or apple core shape (FIG. 45I). In yet further variations, the fine mobility control mechanism is configured as raised, circular flange located at or near the proximal edge of the dynamic sleeve. In one example, the circular flange is raised about 1 mm to about 1.5 mm over the outer surface of the dynamic sleeve, so that the operator has a tactile feel of its surface, and is able to control movement of the sleeve when applying a retractive (pulling) or pushing force to it.

Some variations of the devices described herein include a grip having a retraction slot or channel that works in combination with the dynamic resistance component to inject drug into the eye. Referring to FIG. 45A, grip (906) may be a component coupled (usually fixedly attached) to the device housing (908) at the proximal end (912) of the sleeve (902). The grip (906) may be configured to include a retraction slot (910) in its wall. In use, when the sleeve (902) is retracted, as shown by the direction of the arrow in FIG. 45J, the base (912) of the pad or platform is moved into the slot (910). The retraction slot (910) may be configured as a channel of uniform width (FIG. 45F), or as a channel with a keyhole-type configuration, e.g., having a narrowed portion (FIG. 45G) or enlarged portion (FIG. 45E) at the slot proximal or distal end. The retraction slot may provide sensory feedback, e.g., when the endpoint of retraction is reached. The configuration of the base of the platform or pad may be chosen so that it provides a friction fit with the slot. For example, when the slot has a narrowed portion, the base may also have a narrowed portion.

When grips are employed, the devices may also include a locking mechanism. In one variation, when the end point of the sleeve retraction and needle exposed/deployment is reached, the wide portion of the sleeve slot is aligned with the wide portion of a grip slot and with an opening in the housing and an opening in the plunger shaft, allowing the platform base to be inserted into the plunger shaft to lock it relative to the platform that become an actuation lever for manual drug injection. The narrow part of the base enters the narrow part of the sleeve slot, which unlocks the platform relative to the sleeve allowing its movement towards device tip. In another variation, when the platform base reaches the end point of the retraction slot, it may be depressed into an opening in the plunger shaft and becomes a locking pin to connect the platform and the plunger. When it is depressed, its narrow portion enters the keyhole-shaped slot in the sleeve, and becomes movable within the slot moving towards the tip of the sleeve (unlocks the platform base and sleeve).

The mobility control mechanism may be beneficial when the user desires to control the amount of pressure exerted by the device tip on the eye surface in order to deploy the needle during its intraocular penetration. With a mobility control mechanism, the user may use a fingertip to either reduce or increase counter-forces that regulate the sleeve movement and needle exposure.

For example, if the user exerts the pulling force onto the said high-traction surface (that is pulling the high-traction surface of the sleeve away from the device tip), this movement may facilitate needle exposure and reduce the amount of pressure force (down to 0 Newton) needed to be applied to the eye wall in order to slide the sleeve back and expose the needle. In another variation, if the user exerts a pushing force (that is pushing the high-traction surface of the sleeve towards the device tip), this movement may counteract and impedes needle exposure, which may allow the device tip to apply increased pressure to the eye wall prior to the initiation of sleeve movement and needle exposure.

In use, the platform or pad may be slid with a second or third finger. Again, this allows the injector to manually modulate the sleeve resistance and movement along the device tip. For example, by pushing the pad and thus the sleeve forward with a fingertip, the injector provides some resistance at the beginning of the procedure when the device tip is being positioned on the eye surface (and the needle needs to remain completely covered). Then the injector would release his/her fingertip from the sleeve pad to enable needle deployment and its trans-scleral penetration. Some variations of the device may also include a step or a ring-shaped ridge at the end of the sleeve path, so that after the sleeve is pulled back past this step, it would automatically trigger spring-actuated plunger movement. The fingertip pad could be used to pull the sleeve back past the said step at the end of needle deployment in order to actuate the plunger movement and drug injection.

When a platform or pad is employed, it may reduce the amount of pressure the device exerts on the eyeball before the sleeve begins to move to expose the needle, and thus, allow customization of the amount of applied pressure from patient to patient.

In another aspect, the dynamic sleeve may provide gradual needle exposure as it penetrates through the eye wall so that the needle is exposed 1 mm or less when it meets most resistance at the eye surface. Here the rest of the needle is located inside the sleeve with at least its most distal unexposed point or a longer segment being protected inside the narrow exit orifice or canal. Such sleeve design may minimize the risk of needle bending compared to the conventional syringe with a long exposed needle. This design may enable the utilization of smaller a gauge needle without increased risk of it being bent as it penetrated through the eye wall. The smaller needle gauge may render it more comfortable and less traumatic during its intraocular penetration.

Some variations of the devices described here may comprise an endpoint shock absorber. The endpoint shock absorber may be a component that cushions the eye against the force transmitted by the dynamic sleeve and the needle when they come to an abrupt stop. The transmitted force wave may be harmful for the delicate structures inside the eye such as the lens, retina and the choroidal vasculature. Inclusion of an endpoint shock absorber may allow the needle to come to a soft and gradual stop at the end of its deployment path when it is fully extended through the eye wall into the intraocular cavity. In one variation, the shock absorber is provided as a tapered surface at the distal end or distal portion of the dynamic sleeve. In another variation, the shock absorber is a soft sleeve located at the base of the drug conduit (such as at the hub of an injection needle). Here the soft sleeve may be configured to contact the tip of the device when the needle is fully deployed. In yet another variation, the shock absorber is the soft tip of the device, where the soft tip is configured to contact the hub of the needle when the needle is fully deployed. Exemplary materials suitable to make the endpoint shock absorbers include without limitation, methylmethacrylate (MMA); polymethylmethacrylate (PMMA); polyethylmethacrylate (PEM) and other acrylic-based polymers; polyolefins such as polypropylene and polyethylene, vinyl acetates, polyvinylchlorides, polyurethanes, polyvinylpyrollidones, 2-pyrrolidones, polyacrylonitrile butadiene, polycarbonates, polyamides, fluoropolymers such as polytetrafluoroethylene (e.g., TEFLON™ polymer); polystyrenes; styrene acrylonitriles; cellulose acetate; acrylonitrile butadiene styrene; polymethylpentene; polysulfones; polyesters; polyimides; natural rubber; polyisobutylene rubber; polymethylstyrene; silicone; and derivatives, copolymers and blends thereof.

The devices described herein may also include a visual feedback mechanism or a needle deployment indicator configured to allow the operator to precisely determine when the needle has been deployed to the desired extent, and to safely initiate drug injection. Furthermore, during the needle deployment process, the eyes of the operator should be pointed at or near the device tip-eye interface. Thus, it would be beneficial for the visual feedback mechanism to be located in close proximity to the device tip-eye interface, so as not to distract the operator from closely monitoring the device position during the entire intraocular drug delivery procedure. With such a configuration, the operator does not have to take his/her eyes off of the device-ocular interface during the entire injection procedure, minimizing the risk of accidental trauma during unexpected movement of the eye or head of the subject. In some variations, the visual feedback mechanism may be coupled to a mechanical stopper at the endpoint of the needle deployment process. Here the visual feedback mechanism may be configured as an elongated measuring tip band, where the tip comes up to a stop against the needle base or hub, which determines the endpoint of needle deployment when the sleeve has been fully retracted. In one variation, the needle base and/or the distal end of the needle hub is colored in a high-visibility dye, such as black, that could be directly visualized through a transparent or translucent material of the slidable shield. Another example of the visual feedback mechanism is a band or a spacer placed on the needle base, so that the band comes up to a stop against the inside surface of the tip, which determines the end-point of needle deployment when the sleeve has been fully retracted.

Figure 48:
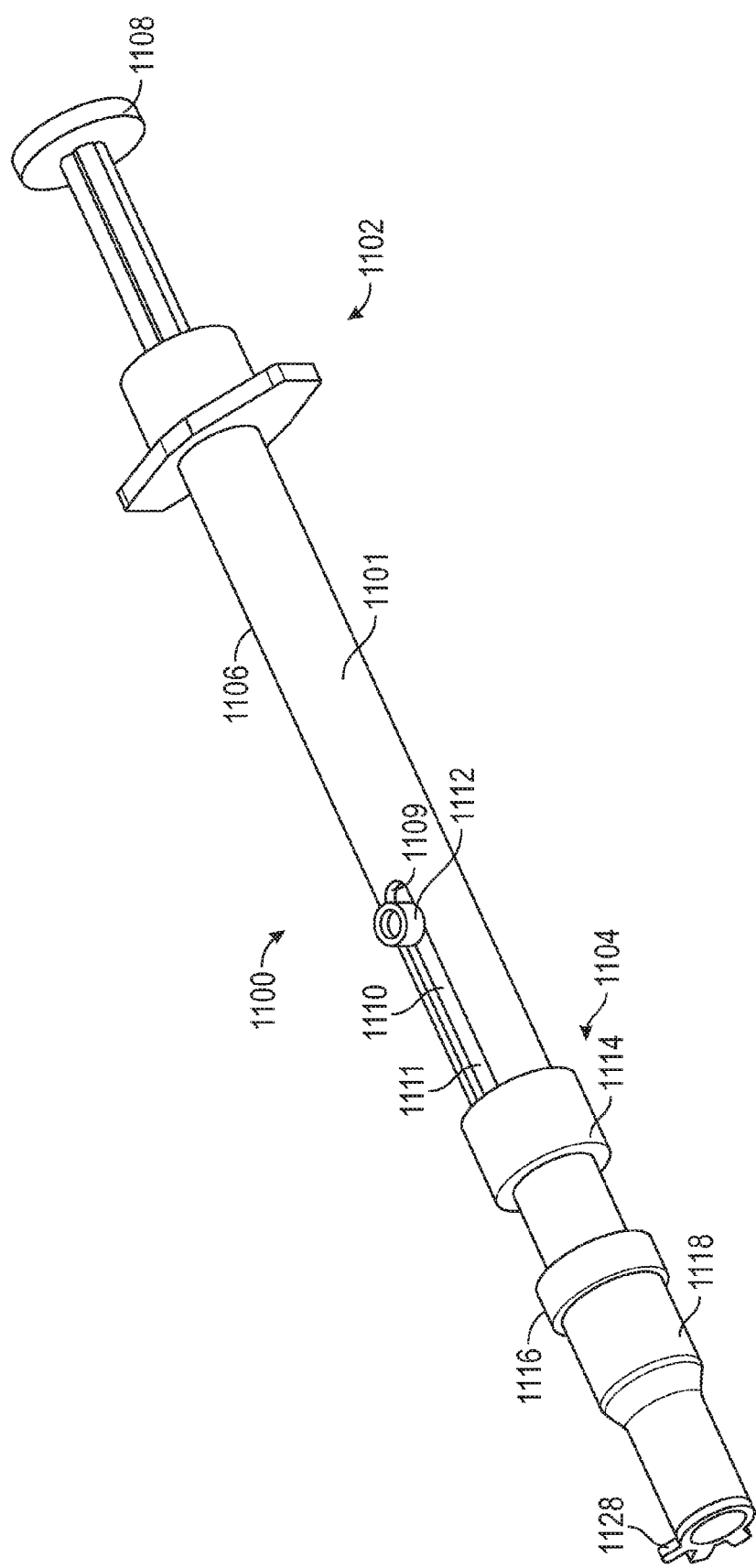
FIG. 48 shows a perspective view of one variation of an intraocular injection device.

An exemplary injection device is shown in FIG. 48. In the figure, injection device (1100) comprises a housing (1101) having a wall (1106), a proximal end (1102), a distal end (1104), and a lumen (not shown) extending between the proximal end (1102) and distal end (1104). A plunger (1108) is slidable at least partially through the lumen. A longitudinally extending channel (1110) having a proximal end (1109) and a distal end (1111) formed through the wall (1106) is provided at the device distal end (1104). A plunger actuation lever such as knob (1112) is configured so that slidable advancement of the knob (1112) from the channel proximal end (1109) to the channel distal end (1111) also slidably advances the plunger (1108) to deliver medication into the eye. The channels may be of any suitable length. The distance from the distal end of the channel (1111) to the distal end of the housing (1104) may range from about 10 to about 20 mm. In FIG. 48, the distance from the distal end of the channel (1111) to the distal end of the housing (1104) is about 16 mm. The injection device of FIG. 48 also includes a cover or sleeve (1114) that overlays an opening or aperture in the housing wall (not shown) through which a drug loader (as previously described) may be placed. The drug loader would deliver medication from a drug vial to the reservoir of the device. The cover or sleeve (1114) may partially, substantially or entirely surround the housing and be made from materials such as rubber or silicone. The drug loader may puncture the cover or sleeve and extend through the opening or aperture of the housing so that medication can be filled into the reservoir.

Figure 49A:
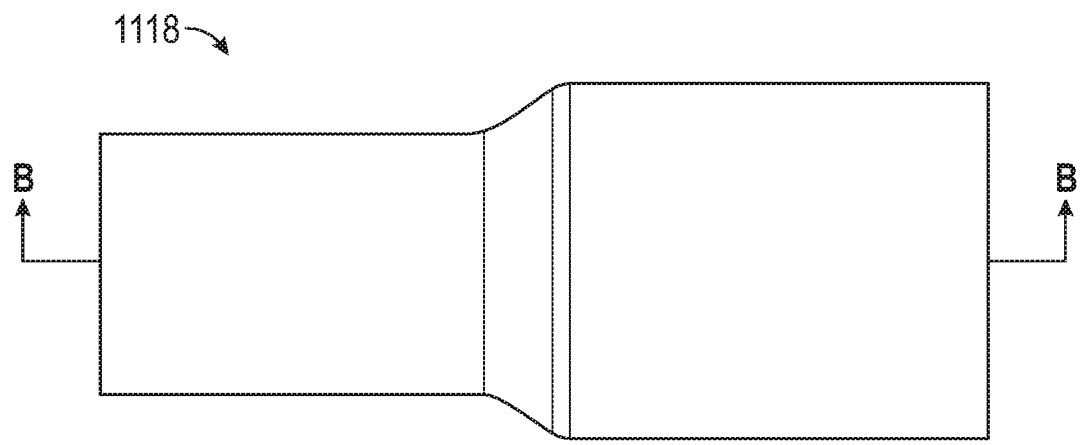
FIGS. 49A and 49B are expanded views of the exemplary dynamic sleeve shown in FIG. 48.
Figure 49B:
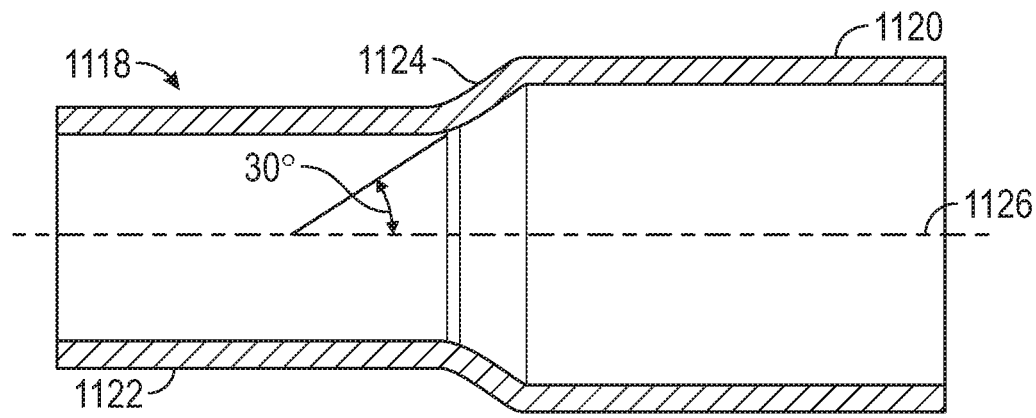

In FIG. 48, the injection device also includes a flange (1116). As previously described, flange (1116) may be part of a fine mobility control mechanism. The flange (1116) may be configured as a raised, circular flange located at or near the proximal edge of a dynamic sleeve (1118). As shown in more detail in FIG. 49B, dynamic sleeve (1118) has a first section (1120) and a second section (1122). The inner diameter of first section (1120) will typically be greater than the inner diameter of second section (1122). For example, the inner diameter of the first section may be about 7.0 mm and the inner diameter of the second section may be about 4.8 mm. The length of the first and second sections may also vary. In FIG. 49B, the length of the first section (1120) may be about 9.0 to 10 mm and the length of the second section (1122) may be about 9.0 to 10 nun. A ramped portion (1124) may also connect the first and second portions (1120 and 1122). Ramped portion (1124) may be configured so that an angle is created with the longitudinal axis (1126) of the device, e.g., an angle of 30 degrees as shown in FIG. 49B.

Figure 50:
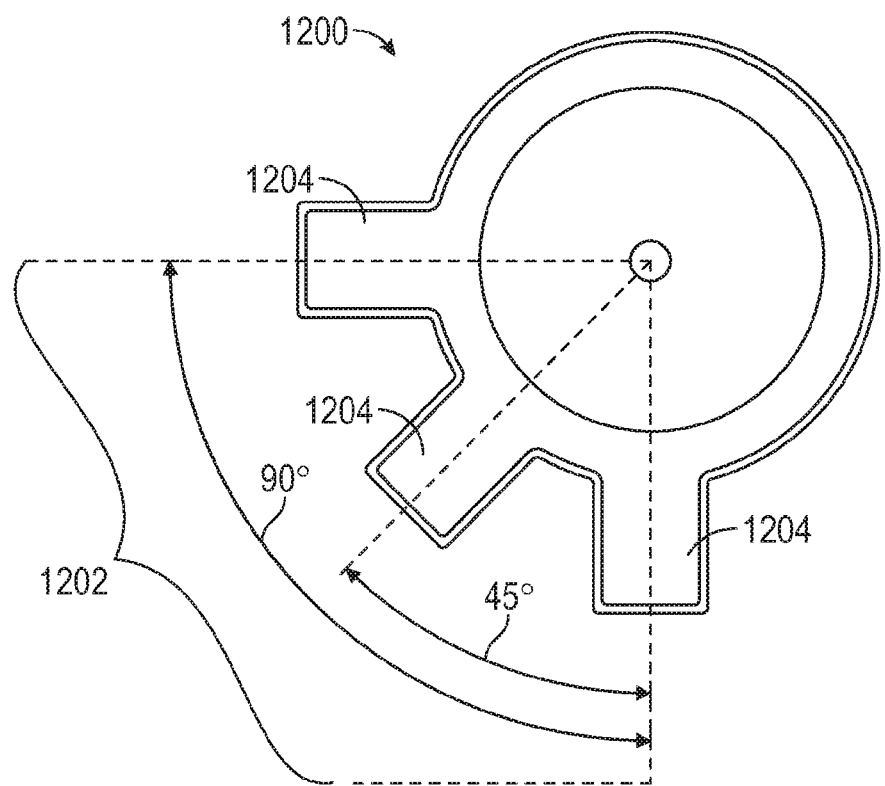
FIG. 50 is an expanded end view of the sectoral measuring component shown in FIG. 48.
Figure 51:
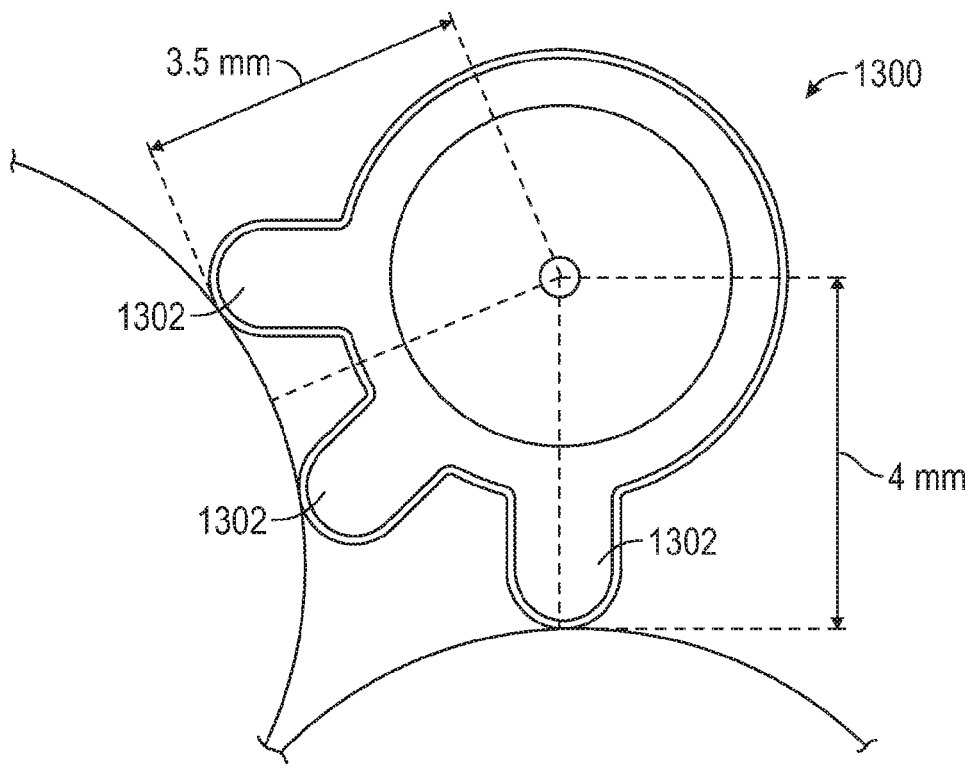
FIG. 51 depicts a sectoral measuring component according to another variation on the surface of the eye at the corneo-scleral limbus.

The injection device of FIG. 48 also includes a sectoral measuring component (1128). The sectoral measuring component in this as well as other variations has a circumference (that spans 360 degrees) and a longitudinal axis. Radially extending members such as tabs or spokes may be provided around the circumference of the sectoral measuring component in any suitable manner, e.g., equidistant from each other, symmetrically or asymmetrically spaced around the circumference, but typically in a manner that avoids contact with the eyelid(s) and eyelashes to maintain its sterility. Thus, the radially extending members will generally be provided on a section (portion) of the circumference and will generally span a certain number of degrees of arc around the circumference. For example, and as specifically shown in FIG. 50, sectoral measuring component (1200) has a section (1202) having three radially extending members (1204). The section (1202) spans an area (e.g., arc) around the circumference of 90 degrees. In this configuration, the radially extending members are spaced around the circumference 45 degrees apart from each other. In another variation, as shown in FIG. 51, sectoral measuring component (1300) is configured similarly to that illustrated in FIG. 50 except that the distal ends of the radially extending members (1302) are rounded.

Figure 58C:
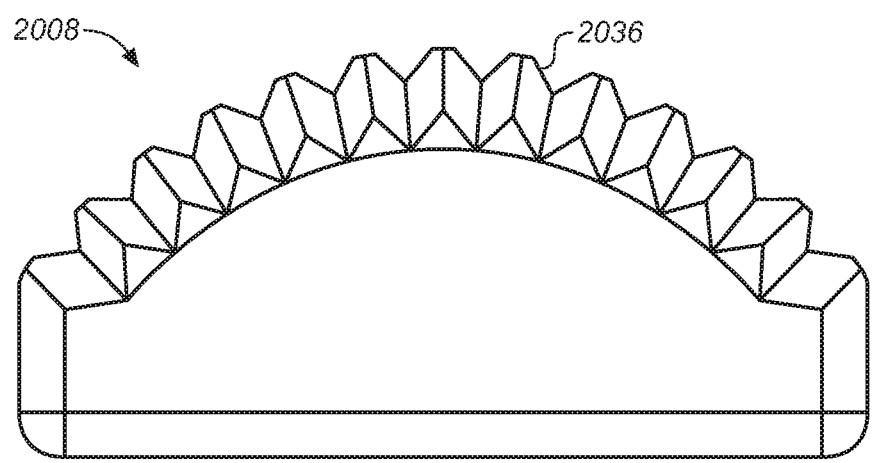

Referring to FIGS. 58A-58C, a further variation of an exemplary ocular drug delivery system/injection device is shown. In FIG. 58A, the injection device (2000) includes a cover (2002), a housing (e.g., a syringe barrel) (2004), a plunger (2006), and a domed actuator (2008) that is slidable within slot (2010) in the housing wall, and which is coupled to the plunger (2006) to deliver drug out of the device. The system is broken down to show its various components in more detail in FIG. 58B. In FIG. 58B, the cover (2002), housing (2004), plunger (2004), and domed actuator (2008) are shown. The cover may be made from any suitable material. Exemplary materials include without limitation, polyethylene, polycarbonate, polypropylene, acrylonitrile butadiene styrene polymers, Delrin® acetal homopolymers, polyurethane, acrylic polymers, polyether ether ketone, and combinations thereof. In one variation, the cover is made from polycarbonate. Further depicted are a seal (2012) at the distal end (2014) of the plunger (2006) and a screw or pin (2016) for fixing the domed actuator (2008) to the plunger (2006). A needle hub assembly (2018) is also shown having an attached 30 gauge needle (2020), projections (2022), and a ring (2024). However, it is understood that the needle hub assembly may include any suitably sized needle. The system further includes a slidable shield (2026). As previously described, movement of the shield (2026) along the projections in the proximal direction (direction of the arrow) creates resistance until the shield (2026) is stopped by ring (2024). In this variation, a filter assembly comprising a filter capture ting (2028), a PTFE filter disk (2030), and a mesh backer (2032) are provided in the needle bub (2018). It is understood that the needle hub (2018) can be removably attached to, or fixed to, the housing (2004). An ocular measuring component (2034) and needle stabilization mechanism, tunnel (2035) is also provided in this variation. In FIG. 58C, an enlarged view of the domed actuator (2008) is depicted. The domed actuator (2008) includes ridges (2036) to aid the grip and or manipulation of the actuator (2008) by the user.

II. METHODS

Methods for using the intraocular drug delivery devices are also described herein. In general, the methods include the steps of positioning an ocular contact surface of the device on the surface of an eye, applying pressure against the surface of the eye at a target injection site using the ocular contact surface, and delivering an active agent from the reservoir of the device into the eye by activating an actuation mechanism. The steps of positioning, applying, and delivering are typically completed with one hand.

The methods may also include placing an ocular contact surface of an injection device against the eye wall, generating variable resistance to conduit advancement as the conduit is deployed through the eye wall, removing air from the composition before the composition is delivered into the eye by passing the composition through an air removal mechanism, and injecting the composition into the eye.

In some instances, the method may include coupling an injector attachment to a syringe body, the injector attachment comprising a variable resistance component, an air removal mechanism, an ocular contact surface, and a needle, and the syringe body having a proximal end and a distal end, and a reservoir for containing a composition therein; placing the ocular contact surface of the injector attachment against the eye wall; generating variable resistance to needle advancement as the needle is deployed through the eye wall; removing air from the composition before the composition is delivered into the eye by passing the composition through the air removal mechanism; and injecting the composition into the eye.

In addition to removing air, the method may further comprise the step of removing bacteria or particulates from the composition before the composition is delivered into the eye, the step of limiting the injection force of the composition, and/or the step of limiting the distance the composition travels in the eye when the composition is injected. When the distance of composition travel in the eye is limited, the distance may be limited to between about 5 mm and about 25 mm, between about 5 mm to about 20 mm, between about 5 mm and about 15 mm, or between about 5 mm to about 10 mm. As previously stated, the removal of air from the composition before it is delivered into the eye may be particularly beneficial when a viscous composition, e.g., a composition comprising ranibizumab, is injected.

The application of pressure against the surface of the eye using the ocular contact surface may also be used to generate an intraocular pressure ranging between 15 mm Hg to 120 mm Hg, between 20 mm Hg to 90 mm Hg, or between 25 mm Hg to 60 mm Hg. As previously stated, the generation of intraocular pressure before deployment of the dispensing member (conduit) may reduce scleral pliability, which in turn may facilitate the penetration of the conduit through the sclera, decrease any unpleasant sensation on the eye surface during an injection procedure, and/or prevent backlash of the device. Intraocular pressure control may be generated or maintained manually or automatically using pressure relief valves, pressure sensors, pressure accumulators, pressure sensors, or components such as slidable caps having locking mechanisms and/or ridges as previously described.

Use of the devices according to the described methods may reduce pain associated with needle penetration through the various covers of the eye wall such as the conjunctiva that is richly innervated with pain nerve endings. The anesthetic effect at the injection site during an intraocular injection procedure may be provided by applying mechanical pressure on the conjunctiva and the eye wall over the injection site before and/or during the needle injection. The application of mechanical pressure to the eye wall may also transiently increase intraocular pressure and increase firmness of the eye wall (and decrease its elasticity), thereby facilitating needle penetration through the sclera. Furthermore, the application of mechanical pressure to the eye wall may displace intraocular fluid within the eye to create a potential space for the drug injected by the device.

The devices may be used to treat any suitable ocular condition. Exemplary ocular conditions include without limitation, any type of retinal or macular edema as well as diseases associated with retinal or macular edema, e.g., age-related macular degeneration, diabetic macular edema, cystoid macular edema, and post-operative macular edema; retinal vascular occlusive diseases such as CRVO (central retinal vein occlusion), BRVO (branch retinal vein occlusion), CRAO (central retinal artery occlusion), BRAO (branch retinal artery occlusion), and ROP (retinopathy of prematurity), neovascular glaucoma; uveitis; central serous chodoretinopathy; and diabetic retinopathy.

When dexamethasone sodium phosphate solution is used to treat an ocular condition, the dose of dexamethasone sodium phosphate that may be administered into the eye by each individual injection device may range between about 0.05 mg and about 5.0 mg, between about 0.1 mg and about 2.0 mg, or between about 0.4 mg and about 1.2 mg.

In some variations, a topical anesthetic agent is applied on the ocular surface before placement of the device on the eye. Any suitable topical anesthetic agent may be used. Exemplary topical anesthetic agents include without limitation, lidocaine, proparacaine, prilocaine, tetracaine, betacaine, benzocaine, bupivacaine, ELA-Max®, EMLA® (eutectic mixture of local anesthetics), and combinations thereof. In one variation, the topical anesthetic agent comprises lidocaine. When lidocaine is used, it may be provided in a concentration raging from about 1% to about 10%, from about 1.5% to about 7%, or from about 2% to about 5%. In another variation, the topical anesthetic agent is mixed with phenylephrine or another agent that potentiates or/and prolongs the anesthetic effect of the pharmaceutical formulation. The topical anesthetic agent may be provided in any suitable form. For example, it may be provided as a solution, gel, ointment, etc.

An antiseptic agent may also be applied on the ocular surface before placement of the device on the eye. An antiseptic agent may also be applied to the device tip before placement of the device on the eye. Examples of suitable antiseptic agents include, but are not limited to, iodine, iodine-containing combinations, povidone-iodine (Betadine®), chlorhexidine, soap, antibiotics, salts and derivatives thereof, and combinations thereof. The antiseptic agent may or may not be applied in combination with a topical anesthetic agent. When the antiseptic comprises povidone-iodine (Betadine®), the concentration of povidone-iodine may range from about 1% to about 10%, from about 2.5% to about 7.5%, or from about 4% to about 6%.

During the drug delivery process, the devices described here may be configured so that the injection needle enters the eye at the right angle that is perpendicular to the eye wall (sclera). In other instances, the device may be configured so that the injection needle enters through the cornea into the anterior chamber of the eye parallel to the iris plane.

III. SYSTEMS AND KITS

Systems and kits that include the intraocular drug delivery devices disclosed herein are also provided. The kits may include one or more integrated drug delivery devices, one or more injection devices, one or more conventional syringes, and/or one or more removably couplable injector attachments. The devices may be preloaded with an active agent. When a plurality of preloaded devices are included, they may be separately packaged and contain the same active agent or different active agents, and contain the same dose or different doses of the active agent.

The systems and kits may also include one or more separately packaged devices (or conventional syringes) that are to be manually loaded. If the devices are to be manually loaded prior to use, then one or more separately packaged active agents may be incorporated into the kit. Similar to the preloaded device system or kit, the separately packaged active agents in the systems and kits here may be the same or different, and the dose provided by each separately packaged active agent may be the same or different.

Of course, the systems and kits may include any combination of preloaded devices, devices (or conventional syringes) for manual loading, and active agents. It should also be understood that instructions for use of the devices will also be included. In some variations, one or more separately packaged measuring components may be provided in the systems and kits for removable attachment to the devices. Topical anesthetic agents and/or antiseptic agents may also be included.

In some variations of the systems and kits, the pharmaceutical formulation is substantially non-irritating to the ocular surface. The pharmaceutical formulation is generally sterile. In one example, the pharmaceutical formulation comprises an antiseptic. In another example, the antiseptic is detergent-free. In yet another example, the antiseptic is in a single-use container. Examples of suitable antiseptic agents include, but are not limited to, iodine, iodine-containing combination, povidone-iodine (Betadine®), chlorhexidine, soap, antibiotics, salts and derivatives thereof, and combinations thereof.

When the antiseptic comprises povidone-iodine (Betadine®), the concentration of povidone-iodine may range from about 1% to about 10%, from about 2.5% to about 7.5%, or from about 4% to about 6%. It may be useful for the concentration of povidone-iodine to be about 5%. The antiseptic formulation may be provided in forms that include, but are not limited to, a solution, an antiseptic-soaked swab, or a single-use reservoir suitable for ophthalmic use.

In other variations, the pharmaceutical formulation comprises an anesthetic agent that is substantially non-initiating to the ocular surface. Here the pharmaceutical formulation may contain both an antiseptic and an anesthetic agent. In other instances, the system/kit may include two separately packaged pharmaceutical formulations, where one formulation contains the antiseptic agent and the other separately packaged formulation contains the anesthetic agent. Examples of anesthetic agents include, but are not limited to, lidocaine, tetracaine. The anesthetic formulation may be provided in forms such as, but not limited to, a solution, a gel, or a anesthetic-soaked swab or spongiform material, or a single-use reservoir suitable for ophthalmic use. The antiseptic agent may or may not be applied in combination with a topical anesthetic agent.

The pharmaceutical formulation may be housed in a container, where the container is integrated with the intravitreal drug injector housing, tip, drug reservoir, or any other suitable part. Alternatively, the container may be configured to detach from the intravitreal drug injector. In one example, the container is hollow reservoir, or drug-soaked spongeform material. In another example, the container is disposable and packaged for a single-use. In yet a further example, the container is sterile.

A pharmaceutical formulation may be applied on the ocular surface before placement of the device on the eye. A pharmaceutical formulation may also be applied on the ocular contact surface of the device tip before placement of the device on the eye. For example, an antiseptic may be applied on the ocular surface before placement of the device on the eye. In another example, an antiseptic may also be applied on the ocular contact surface of the device tip before placement of the device on the eye. In one variation, a physician may apply 5% povidone-iodine-containing pharmaceutical formulation onto the device tip prior to placing the device onto the eye surface in order to ensure sterility of the injection site.

The systems or kits for intravitreal drug delivery may comprise an integrated filter-containing drug conduit, or filter-containing drug reservoir, or a filter-containing adapter for transferring and/or loading a drug from a storage container into the intravitreal injection devices described herein. In one example, the filter is a hydrophilic membrane. In another example, the filter's pore size is less than 4 microns, or less than 0.4 microns, or between 0.1 microns and 0.4 microns. In another example, the filter sterilizes a drug solution, for example, by size-exclusion filtration. Such a filter may remove bacterial pathogens. In another example, the filter removes fungal pathogens. In yet another example, the filter collectively removes bacterial, fungal and certain other pathogens.

This application further discloses the following variations 1-41:

Variation 1. An injector attachment for connection to an injection device housing comprising: a needle assembly, the needle assembly having a proximal end and a distal end; a resistance component; and an ocular contact surface.

Variation 2. The injector attachment of variation 1, wherein the resistance component comprises a slidable sleeve.

Variation 3. The injector attachment of variation 1, wherein the resistance component comprises a lever.

Variation 4. The injector attachment of variation 3, wherein the lever releasably secures a slidable sleeve.

Variation 5. The injector attachment of variation 3, wherein the lever is fixedly attached to the needle assembly.

Variation 6. The injector attachment of variation 3, wherein the lever is releasably attached to the needle assembly.

Variation 7. The injector attachment of variation 1, wherein the ocular contact surface comprises a measuring component.

Variation 8. The injector attachment of variation 1, wherein the measuring component comprises a plurality of radially extending members.

Variation 9. The injector attachment of variation 8, wherein the plurality of radially extending members are disposed 360 degrees about the circumference of the measuring component.

Variation 10. The injector attachment of variation 2, wherein the slidable sleeve is rigid.

Variation 11. The injector attachment of variation 2, wherein the slidable sleeve is nondeformable.

Variation 12. The injector attachment of variation 1, wherein the needle assembly further comprises a needle stabilization mechanism.

Variation 13. The injector attachment of variation 1, wherein the needle assembly further comprises one or more filters.

Variation 14. The injector attachment of variation 1, wherein the needle assembly further comprises a hydrophilic filter.

Variation 15. The injector attachment of variation 14, wherein the needle assembly further comprises a hydrophobic filter.

Variation 16. The injector attachment of variation 1, further comprising a needle deployment indicator.

Variation 17. The injector attachment of variation 16, wherein the needle deployment indicator comprises a high visibility dye.

Variation 18. A system for delivering a pharmaceutical formulation into the eye comprising: the injector attachment of variation 1; a housing; and a drug reservoir disposed within the housing.

Variation 19. The system of variation 18, wherein the housing comprises a syringe.

Variation 20. The system of variation 18, wherein the housing bas a proximal end, a distal end, and a side wall, and comprises an actuation mechanism for delivering an active agent into an eye, wherein the actuation mechanism comprises a plunger.

Variation 21. The system of variation 20, wherein the actuation mechanism comprises a plunger actuation lever fixedly attached to the plunger and extending through the side wall of the housing.

Variation 22. The system of variation 21, wherein the actuation mechanism further comprises a back plunger.

Variation 23. The system of variation 18, further comprising an active agent contained within the drug reservoir.

Variation 24. The system of variation 23, wherein the active agent comprises an anti VEGF agent selected from the group consisting of ranibizumab, bevacizumab, aflibercept, and modifications, derivatives, and analogs thereof, and combinations thereof.

Variation 25. The system of variation 24, wherein the active agent comprises ranibizumab or bevacizumab.

Variation 26. The system of variation 23, wherein the active agent comprises aflibercept, ocriplasmin, a steroid, ranibizumab, bevacizumab, a placenta-derived growth factor, a platelet-derived growth factor, or combinations thereof.

Variation 27. The system of variation 23, wherein the active agent comprises an anti-complement agent.

Variation 28. A method for injecting a pharmaceutical formulation into the eye comprising: coupling an injector attachment to a syringe having a proximal end and a distal end, the injector attachment comprising a needle assembly having a needle, and a resistance component: generating a resistive force with the resistance component; advancing the needle through the eye wall; and injecting the pharmaceutical formulation into the eye.

Variation 29. The method of variation 28, wherein the resistive force is between 0 N and about 2 N.

Variation 30. The method of variation 29, wherein the resistive force is between about 0.05 N and about 0.5 N.

Variation 31. The method of variation 28, wherein the resistance component comprises a slidable sleeve.

Variation 32. The method of variation 28, wherein the resistance component comprises a lever having a locked configuration and an unlocked configuration.

Variation 33. The method of variation 32, wherein depression of one side the lever places the lever in its unlocked configuration.

Variation 34. The method of variation 28, wherein the needle assembly further comprises a needle stabilization mechanism.

Variation 35. The method of variation 28, wherein the pharmaceutical formulation is preloaded in the syringe.

Variation 36. The method of variation 28, wherein the pharmaceutical formulation is loaded into the syringe immediately prior to its use.

Variation 37. The method of variation 30, wherein the pharmaceutical formulation comprises an active agent.

Variation 38. The method of variation 37, wherein the active agent comprises an anti-VEGF agent selected from the group consisting of ranibizumab, bevacizumab, aflibercept, and modifications, derivatives, and analogs thereof, and combinations thereof.

Variation 39. The method of variation 38, wherein the active agent comprises ranibizumab or bevacizumab.

Variation 40. The method of variation 37, wherein the active agent comprises aflibercept, ocriplasmin, a steroid, ranibizumab, bevacizumab, a placenta-derived growth factor, a platelet-derived growth factor, or combinations thereof.

Variation 41. The method of variation 37, wherein the active agent comprises an anti-complement agent.

IV. EXAMPLES

The following examples serve to more fully describe the manner of using the above-described intraocular injection devices. It is understood that this example in no way serves to limit the scope of the invention, but rather is presented for illustrative purposes.

Example 1: Resistance Force Generated by the Slidable Sleeve/Shield

An intraocular injection device comprising a 30-gauge needle covered by a dynamic sleeve was fixed onto an Imada tensile testing bed and moved against an Imada 10 N force gauge at a rate of 10 mm/minute. The resistance force was measured while the sleeve was pushed back to expose the needle simulating the movement of the sleeve in practice. This produced a 'U"-shaped force plotted against the sleeve displacement curve, as shown in FIG. 46. The resistance force at the beginning and the end of sleeve movement path was greater than that in the middle of the path. In FIG. 46, the illustrated range of resistance force generated may be between zero Newton and about 2 Newton or between about 0.01 Newton and about 1.0 Newton, or between about 0.05 Newton and about 0.5 Newton.

In one instance, the resistance force at the beginning of the sleeve path equaled the force required for the 30- or 31-gauge needle to penetrate through the human sclera (e.g., between 0.2 Newton and 0.5 Newton). When a using a higher-resistance sleeve was employed, the resistance force at the beginning of the sleeve path was greater than the force required for the 30- or 31-gauge needle to penetrate through the human sclera (e.g., over 1 Newton). However, the force was low enough to be comfortable for the patient and avoid potential damage to the eye (e.g., to avoid increase in intra-ocular pressure over 60 mmHg). In the middle portion of the sleeve movement path, the force approached zero Newton.

Example 2: Needle Bend and Recovery Force

Figure 64:
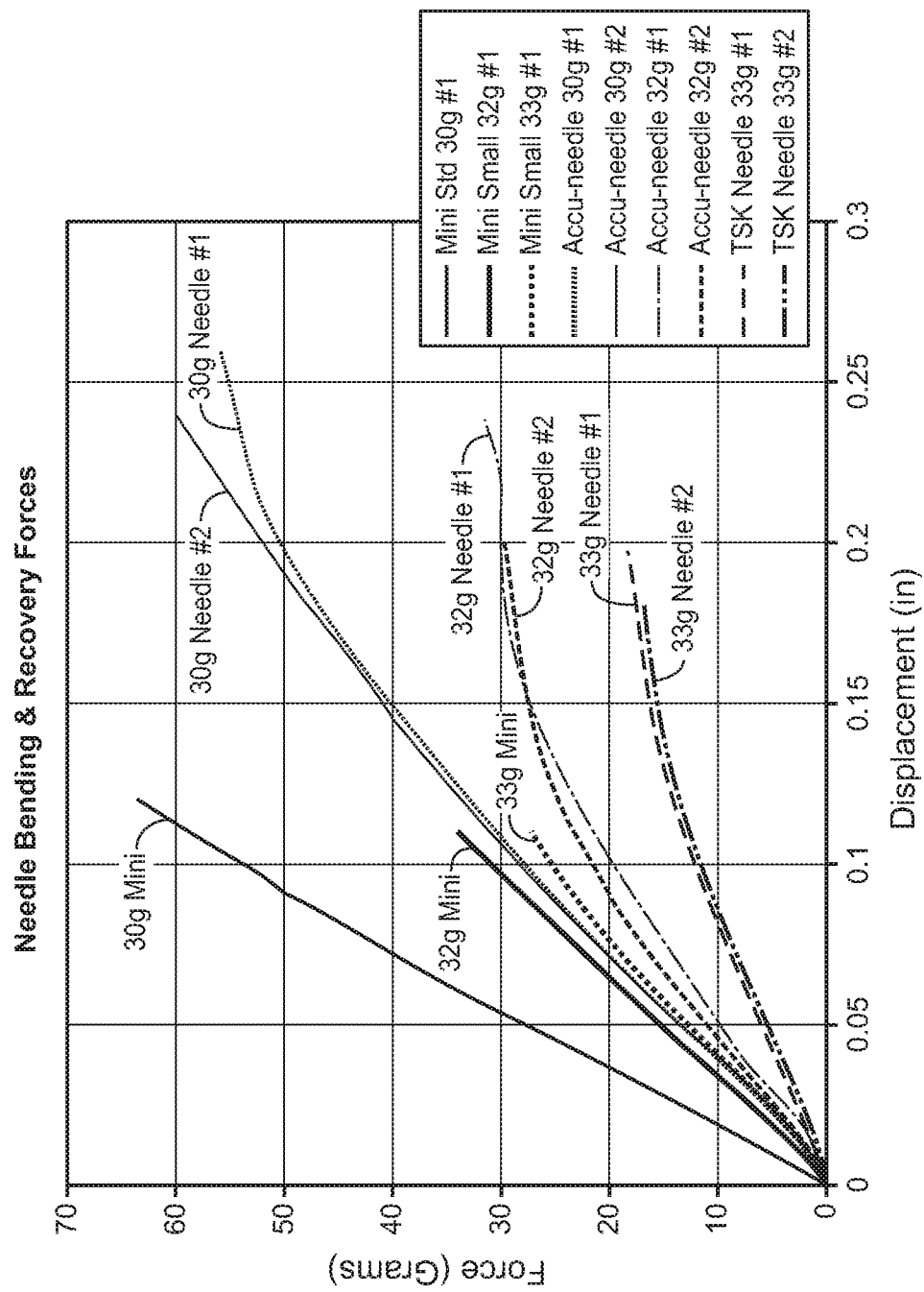
FIG. 64 is a graph that compares the needle bend and recovery forces of an exemplary needle having a needle stabilization mechanism to commercially available needles.

Tests were run to compare the needle bending and recovery forces of a needle (labeled "Mini" in the graph shown in FIG. 64) having a needle-stabilizing component (here a guide tunnel) to commercially available needles (Accu-needles and TSK needles; TSK Laboratory, Inc., Japan).

A maximum of 30° deflection was set based on the length of the needles. Each type of needle was placed into fixture, and mill digital readouts were zeroed and the balance was tared. The test needles were moved down against the deflection fixture and the force on the scale at each test interval recorded until the maximum displacement was reached. The motion was reversed on the mill and the recovery force at each interval was recorded. Any permanent deformation of the needle was recorded.

As shown in the graph, the "Mini" needles significantly increased the bending force required to bend or deform compared to the Accu-needles and TSK needles. The 32 to 33 gauge "Mini" needles had a similar stiffness and resistance to bending as the commercially available 30 gauge needles.

What is claimed is:

1. An injector attachment for connection to an injection device housing, comprising:
a needle hub comprising a tubular body and comprising an input port on its proximal end for removable connection to an injector having a drug reservoir, and a distal stop surface;
a needle comprising a proximal portion and a distal portion, the proximal portion of the needle housed within the tubular body of the needle hub, and the distal portion of the needle extending distally beyond the needle hub;
a rigid slidable shield comprising a distal opening, a proximal opening, and an uninterrupted sidewall between the distal opening and the proximal opening configured to protect the sterility of the needle and operatively coupled to the needle hub and having a fixed axial dimension, the slidable shield configured for axial movement along the needle hub between the input port and the distal stop surface and configured such that the needle is completely circumscribed by the shield and the tubular body of the needle hub when the shield is in a first, distal position with respect to the needle hub, and the distal portion of the needle extends distally beyond the shield when the shield is in a second, proximal position with respect to the needle hub,
a patient contact surface, the patient contact surface comprising a perimeter and located at a distal end of the slidable shield; and
a lever attached to the needle hub, the lever configured to prevent axial movement of the slidable shield and to maintain the shield in the first, distal position with respect to the needle hub by a locking shoulder at a distal end of the lever contacting a proximal end wall of the slidable shield thereby preventing proximal movement of the shield away from the first, distal position.

2. The needle injector of claim 1, further comprising a flange extending from an outer surface at or near the proximal end of the slidable shield.

3. The needle injector of claim 2, wherein the flange is raised from about 1 mm to about 1.5 mm over the outer surface of the slidable shield.

4. The needle injector of claim 1, wherein the flange comprises a circular shape.

5. The needle assembly of claim 1, wherein the patient contact surface comprises a measuring component, the measuring component comprising three or more radially extending members, each of the radially extending members comprising substantially the same shape and length and configured to measure a precise distance between the distal end of the conduit and an anatomical landmark of a patient's surface tissue.

6. A system for delivering a pharmaceutical formulation into a target location of a patient comprising:
the injector attachment of claim 1;
a housing; and
a drug reservoir disposed within the housing.

7. The system of claim 6, wherein the housing comprises a syringe.

8. The system of claim 6, wherein the housing has a proximal end, a distal end, and a side wall, and comprises an actuation mechanism for delivering an active agent into an eye, wherein the actuation mechanism comprises a plunger.

9. The system of claim 8, further comprising an active agent contained within the drug reservoir.

* * * * *

UNITED STATES PATENT AND TRADEMARK OFFICE
CERTIFICATE OF CORRECTION

PATENT NO.        : 9,895,259 B2
APPLICATION NO.   : 15/442054
DATED             : February 20, 2018
INVENTOR(S)       : Leonid E. Lerner Page 1 of 1

It is certified that error appears in the above-identified patent and that said Letters Patent is hereby corrected as shown below:

In the Claims

In Column 66 at Line 63, Change "assembly" to --injector--.

Signed and Sealed this
Twenty-first Day of August, 2018

Andrei Iancu
*Director of the United States Patent and Trademark Office*